United States Patent
Bassan et al.

(10) Patent No.: US 12,390,456 B2
(45) Date of Patent: *Aug. 19, 2025

(54) PRIDOPIDINE FOR TREATING HUNTINGTON'S DISEASE

(71) Applicant: PRILENIA NEUROTHERAPEUTICS LTD., Herzliya (IL)

(72) Inventors: Merav Bassan, Netanya (IL); Esther Lukasiewicz Hagai, Tel Aviv (IL); Eli Eyal, Petah-Tikva (IL); Anna Kristina Sveinsdotter Teige Wickenberg, Lund (SE)

(73) Assignee: Prilenia Neurotherapeutics Ltd., Yakum (IL)

(*) Notice: Subject to any disclaimer, the term of this patent is extended or adjusted under 35 U.S.C. 154(b) by 307 days.

This patent is subject to a terminal disclaimer.

(21) Appl. No.: 17/352,305

(22) Filed: Jun. 20, 2021

(65) Prior Publication Data

US 2021/0308115 A1    Oct. 7, 2021

Related U.S. Application Data

(63) Continuation of application No. 16/438,508, filed on Jun. 12, 2019, now Pat. No. 11,090,297, which is a continuation-in-part of application No. 14/309,111, filed on Jun. 19, 2014, now Pat. No. 10,322,119.

(60) Provisional application No. 61/877,832, filed on Sep. 13, 2013, provisional application No. 61/837,928, filed on Jun. 21, 2013.

(51) Int. Cl.
*A61K 31/451* (2006.01)
*A61K 9/00* (2006.01)
*A61P 25/28* (2006.01)

(52) U.S. Cl.
CPC .......... *A61K 31/451* (2013.01); *A61K 9/0053* (2013.01); *A61P 25/28* (2018.01)

(58) Field of Classification Search
CPC .. A61K 31/451; A61K 9/0053; A61K 9/4825; A61K 9/4866; A61P 25/28
See application file for complete search history.

(56) References Cited

U.S. PATENT DOCUMENTS

| | | |
|---|---|---|
| 6,903,120 B2 | 6/2005 | Sonesson et al. |
| 7,417,043 B2 | 8/2008 | Sonesson et al. |
| 7,923,459 B2 | 4/2011 | Gauthier et al. |
| 8,669,048 B2 | 3/2014 | Reijo Pera et al. |
| 8,703,763 B2 | 4/2014 | Baumann et al. |
| 8,703,764 B2 | 4/2014 | Sheldon |
| 9,006,445 B2 | 4/2015 | Sonesson et al. |
| 9,012,476 B2 | 4/2015 | Zimmermann et al. |
| 9,139,525 B2 | 9/2015 | Wikström |
| 9,187,567 B2 | 11/2015 | Nichols et al. |
| RE46,117 E | 8/2016 | Sonesson et al. |
| 9,602,765 B2 | 3/2017 | Wang et al. |
| 9,744,155 B2 | 8/2017 | Matson |
| 9,796,673 B2 | 10/2017 | Wu et al. |
| 9,814,706 B2 | 11/2017 | Zimmermann et al. |
| 10,047,049 B2 | 8/2018 | Barel et al. |
| 10,130,621 B2 | 11/2018 | Schmidt et al. |
| 2010/0048509 A1 | 2/2010 | Kovacic et al. |
| 2011/0206782 A1 | 8/2011 | Zhang |
| 2013/0150406 A1 | 6/2013 | Anne et al. |
| 2013/0197031 A1 | 8/2013 | Sonesson |
| 2013/0267552 A1 | 10/2013 | Waters et al. |
| 2014/0088140 A1 | 3/2014 | Hayden et al. |
| 2014/0088145 A1 | 3/2014 | Hayden et al. |
| 2014/0378508 A1 | 12/2014 | Bassan et al. |
| 2015/0202302 A1 | 7/2015 | Licht et al. |
| 2015/0209346 A1 | 7/2015 | Hayden |
| 2015/0216850 A1 | 8/2015 | Hayden et al. |
| 2015/0374677 A1* | 12/2015 | Schmidt .................. A61P 25/00 546/217 |
| 2016/0095847 A1 | 4/2016 | Sonesson |
| 2016/0166559 A1 | 6/2016 | Sonesson |
| 2016/0243098 A1 | 8/2016 | Geva et al. |
| 2017/0020854 A1 | 1/2017 | Licht et al. |
| 2017/0022158 A1 | 1/2017 | Barel et al. |
| 2017/0266170 A1 | 9/2017 | Waters et al. |
| 2018/0055832 A1 | 3/2018 | Hayden et al. |
| 2018/0235950 A1 | 8/2018 | Sonesson |
| 2019/0015401 A1 | 1/2019 | Sonesson |
| 2019/0030016 A1 | 1/2019 | Schmidt et al. |

(Continued)

FOREIGN PATENT DOCUMENTS

| | | |
|---|---|---|
| WO | WO 2001/046145 | 6/2001 |
| WO | WO 2005/097122 | 10/2005 |

(Continued)

OTHER PUBLICATIONS

Lundin, A., et al. (2010). Efficacy and safety of the dopaminergic stabilizer pridopidine (ACR16) in patients with Huntington's disease. Clinical neuropharmacology, 33(5), 260- 264.

Squitieri, F., et al. (2013). One-year safety and tolerability profile of pridopidine in patients with Huntington disease. Neurology, 80(12), 1086-1094.

Alexander, G. E., DeLong, M. R., & Strick, P. L. (1986). Parallel organization of functionally segregated circuits linking basal ganglia and cortex. Annual review of neuroscience, 9(1), 357-381.

Bechtel, N. et al. (2010)-Tapping linked to function and structure in premanifest and symptomatic Huntington disease—Neurology, 75(24), 2150-2160.

(Continued)

*Primary Examiner* — Sarah Pihonak

(74) *Attorney, Agent, or Firm* — Mark S. Cohen; PEARL COHEN ZEDEK LATZER BARATZ LLP

(57) ABSTRACT

A method of treating a human patient afflicted with Huntington's disease, comprising periodically orally administering to the patient a pharmaceutical composition comprising pridopidine, its analog or a pharmaceutically acceptable salt thereof.

9 Claims, 2 Drawing Sheets

(56) References Cited

U.S. PATENT DOCUMENTS

| | | | |
|---|---|---|---|
| 2019/0046516 | A1 | 2/2019 | Russ et al. |
| 2019/0192496 | A1 | 6/2019 | Hayden et al. |
| 2019/0209542 | A1 | 7/2019 | Licht et al. |
| 2019/0231768 | A1* | 8/2019 | Geva ..................... A61K 45/06 |

FOREIGN PATENT DOCUMENTS

| | | |
|---|---|---|
| WO | WO 2006/040155 | 4/2006 |
| WO | WO 2007/067617 | 6/2007 |
| WO | WO 2008/127188 | 10/2008 |
| WO | WO 2011/107583 | 9/2011 |
| WO | WO 2012/028635 | 3/2012 |
| WO | WO 2013/034622 | 3/2013 |
| WO | WO 2013/086425 | 6/2013 |
| WO | WO 2013/152105 | 10/2013 |
| WO | WO 2015/112601 | 7/2015 |
| WO | WO 2016/003919 | 1/2016 |
| WO | WO 2016/138130 | 9/2016 |
| WO | WO 2016/138135 | 9/2016 |
| WO | WO 2017/015609 | 1/2017 |
| WO | WO 2017/015615 | 1/2017 |
| WO | WO 2017/048457 | 3/2017 |
| WO | WO 2017/147366 | 8/2017 |
| WO | WO 2018/039475 | 3/2018 |
| WO | WO 2018/039477 | 3/2018 |
| WO | WO 2018/053275 | 3/2018 |
| WO | WO 2018/053280 | 3/2018 |
| WO | WO 2018/053287 | 3/2018 |
| WO | WO 2018/136600 | 7/2018 |
| WO | WO 2019/036358 | 2/2019 |
| WO | WO 2019/046568 | 3/2019 |
| WO | WO 2019/050775 | 3/2019 |

OTHER PUBLICATIONS

Bemelmans, Alexis-Pierre, et al. (1999). Brain-derived neurotrophic factor-mediated protection of striatal neurons in an excitotoxic rat model of Huntington's disease, as demonstrated by adenoviral gene transfer. Human gene therapy, 10.18: 2987-2997.
Bezdicek, O., et al. (2013). Validity of the Montreal Cognitive Assessment in the detection of cognitive dysfunction in Huntington's disease. Applied Neuropsychology: Adult, 20(1), 33-40.
Bowie, C. R., & Harvey, P. D. (2006). Administration and interpretation of the Trail Making Test. Nature protocols, 1(5), 2277.
Briefs, B., 2010, NeuroSearch's dopaminergic stabilizer improves movement disorders in Huntington's disease. Nature Reviews Drug Discovery 9, 260.
Brown, M., Sinacore, D. R., Binder, E. F., & Kohrt, W. M. (2000). Physical and performance measures for the identification of mild to moderate frailty. The Journals of Gerontology Series A: Biological Sciences and Medical Sciences, 55(6), M350-M355.
Canals, Josep M., et al. (2004). Brain-derived neurotrophic factor regulates the onset and severity of motor dysfunction associated with enkephalinergic neuronal degeneration in Huntington's disease. Journal of Neuroscience, 24.35: 7727-7739.
Carlsson Research; May 8, 2006; "Carlsson Research Reports Positive Effects of ACR16 in Huntington Disease Phase II Study" Press Release.
Carlsson, A., & Lindqvist, M. (1963). Effect of chlorpromazine or haloperidol on formation of 3-methoxytyramine and normetanephrine in mouse brain. Acta pharmacologica et toxicologica, 20(2), 140-144.
Cepeda, C., Cummings, D. M., André, V. M., Holley, S. M., & Levine, M. S. (2010). Genetic mouse models of Huntington's disease: focus on electrophysiological mechanisms. ASN neuro, 2(2), AN20090058.
Cho, Sung-Rae, et al. (2007) .Induction of neostriatal neurogenesis slows disease progression in a transgenic murine model of Huntington disease. The Journal of clinical investigation, 117.10: 2889-2902.

Ciammola, A., et al. 2007. Low brain-derived neurotrophic factor (BDNF) levels in serum of Huntington's disease patients. American Journal of Medical Genetics Part B: Neuropsychiatric Genetics, 144.4: 574-577.
Clinical Trial EudraCT Number 2004-000394-60, "A randomised phase II multicentre, double blind, parallel group, placebo controlled study of ACR16 50 mg once daily for the symptomatic treatment of Huntington disease" EU Clinical Trials Register, Sponsor: A. Carlsson Research AB, Sponsor Protocol No. ACR16C007 Start Date: Jun. 30, 2004 https://www.clinicaltrialsregister.eu/ctr-search/search?query=ACRI6C007.
Clinical Trial, NCT00665223, "A Study of Treatment With Pridopidine (ACR16) in Patients With Huntington's Disease (MermaiHD)", ClinicalTrials.gov, Sponsor Teva Pharmaceutical Industries, First Posted: Apr. 23, 2008 https://clinicaltrials.gov/ct2/show/NCT00665223?term=Pridopidine&cond=Huntington+Disease&rank=6.
Clinical Trial, NCT00724048, "A Study of Pridopidine (ACR16) for the Treatment of Patients With Huntington's Disease (HART)", ClinicalTrials.gov, Sponsor Teva Pharmaceutical Industries, First Posted: Jul. 29, 2008 https://clinicaltrials.gov/ct2/show/record?term=Pridopidine&cond=Huntington+Disease&rank=5.
Constantinescu et al. (Mar. 2009)—Levels of the light subunit of neurofilament triplet protein in cerebrospinal fluid in Huntington's disease, Parkinsonism & Related Disorders, p. 245-248.
Craufurd, D., Thompson, J. C., & Snowden, J. S. (2001). Behavioral changes in Huntington disease. Cognitive and Behavioral Neurology, 14(4), 219-226.
Dahlen, Patrik; NeuroSearch A/S reports conclusions from the Multiple Ascending Dose study (MAD) with Huntexil®, May 28, 2012.
De Yebenes, J. G., et al. (2011). Pridopidine for the treatment of motor function in patients with Huntington's disease (MermaiHD): a phase 3, randomised, double-blind, placebo-controlled trial. The Lancet Neurology, 10(12), 1049-1057.
Dragatsis, Ioannis; Levine, Michael S.; Zeitlin, Scott. Inactivation of Hdh in the brain and testis results in progressive neurodegeneration and sterility in mice. Nature genetics, 2000, 26.3: 300-306.
Dubinsky, R., et al. (2010). Third Annual Huntington Disease Clinical Research Symposium. Neurotherapeutics, 7(1), 135-147.
Dunlop, B. W., & Nemeroff, C. B. (2007). The role of dopamine in the pathophysiology of depression. Archives of general psychiatry, 64(3), 327-337.
Dyhring, T., et al. (2010). The dopaminergic stabilizers pridopidine (ACR16) and (−)-OSU6162 display dopamine D2 receptor antagonism and fast receptor dissociation properties. European journal of pharmacology, 628(1-3), 19-26.
Exploratory Population Pharmacokinetic Modeling and Simulations With Pridopidine (Report No. CP-13-013), Jul. 10, 2013, Pharsight Consulting Services.
Extended European Search Report for EP Application No. 1481362.1 dated Jan. 11, 2017.
Ferrara, J. M. et al.(2012)-Effect of tetrabenazine on motor function in patients with Huntington disease—Neurology and therapy, 1(1), 5.
Ferrer, I., et al. Brain-derived neurotrophic factor in Huntington disease. Brain research, 2000, 866.1-2: 257-261.
Francardo, Veronica, et al. Pridopidine induces functional neurorestoration via the sigma-1 receptor in a mouse model of parkinson's disease. Neurotherapeutics, 2019, 16.2: 465-479.
Gauthier, Laurent R., et al. Huntingtin controls neurotrophic support and survival of neurons by enhancing BDNF vesicular transport along microtubules. Cell, 2004, 118.1: 127-138.
Geva, M., et al. Pridopidine for the Treatment of Early Huntington's Disease: 250. Movement Disorders, 2020, 35.
Geva, Michal, et al. (2016) Pridopidine activates neuroprotective pathways impaired in Huntington Disease. Human molecular genetics, 25.18: 3975-3987.
Gharami, Kusumika, et al. (2008) Brain-derived neurotrophic factor over-expression in the forebrain ameliorates Huntington's disease phenotypes in mice. Journal of neurochemistry, 105.2: 369-379.
Giralt, A., et al. (2009). Brain-derived neurotrophic factor modulates the severity of cognitive alterations induced by mutant huntingtin:

(56) References Cited

OTHER PUBLICATIONS involvement of phospholipaseCγ activity and glutamate receptor expression. Neuroscience, 158.4: 1234-1250.

Group, T. E. (1990). EuroQol-a new facility for the measurement of health-related quality of life. Health policy, 16(3), 199-208.

Guy, W. E. (1976). ECDEU assessment manual for psychopharmacology-revised (DHEW Publ No. ADM 76-338). Rockville, MD, US Department of Health, Education, and Welfare. Public Health Service, Alcohol, Drug Abuse, and Mental Health Administration, NIMH Psychopharmacology Research Branch, Division of Extramural Research Programs, 1076, 534-7.

Hedlin, M.(2011)—Pridopidine-Huntexil-ACR-16-Hopes-Huntington's Disease Information—XP055707622—Retrieved from the Internet—URL:https://hopes.stanford.edu/pridopidine-huntexil-acr-16/.

Hobart, J. C., Riazi, A., Lamping, D. L., Fitzpatrick, R., & Thompson, A. J. (2003). Measuring the impact of MS on walking ability: the 12-Item MS Walking Scale (MSWS-12). Neurology, 60(1), 31-36.

Hocaoglu, M. B., Gaffan, E. A., & Ho, A. K. (2012). The Huntington's Disease health-related Quality of Life questionnaire (HDQoL): a disease-specific measure of health-related quality of life. Clinical genetics, 81(2), 117-122.

Huang, Y. C., et al. (2011). Increased prothrombin, apolipoprotein A-IV, and haptoglobin in the cerebrospinal fluid of patients with Huntington's disease. PLoS One, 6(1), p. 1-9.

Huntington Study Group HART Investigators. (2013). A randomized, double-blind, placebo-controlled trial of pridopidine in Huntington's disease. Movement Disorders, 28(10), 1407-1415.

Huntington Study Group Trend-HD Investigators. (2008). Randomized controlled trial of ethyl-eicosapentaenoic acid in Huntington disease. Archives of neurology, 65(12), 1582-1589.

Huntington Study Group. (2003). Dosage effects of riluzole in Huntington's disease: a multicenter placebo-controlled study. Neurology, 61(11), 1551-1556.

Huntington Study Group. (2006). Tetrabenazine as antichorea therapy in Huntington disease: a randomized controlled trial. Neurology, 66(3), 366-372.

Huntington, H. S. G. (1996). Unified Huntington's disease rating scale: reliability and consistency. Movement Disorders, 11, 136-142.

Huot, P., Lévesque, M., & Parent, A. (2006). The fate of striatal dopaminergic neurons in Parkinson's disease and Huntington's chorea. Brain, 130(1), 222-232.

International Search Report and Written Opinion for PCT application No. PCT/US2014/043204 dated Oct. 10, 2014.

International Search Report and Written Opinion for PCT application No. PCT/US2017/048461 dated Aug. 24, 2017.

International Search Report for PCT Application No. PCT/IL2020/050654 dated Aug. 4, 2020.

Joffres, C., Graham, J., & Rockwood, K. (2000). Qualitative analysis of the clinician interview-based impression of change (Plus): methodological issues and implications for clinical research. International psychogeriatrics, 12(3), 403-413.

Kalia, L. V., Kalia, S. K., & Salter, M. W. (2008). NMDA receptors in clinicalneurology: excitatory times ahead. The Lancet Neurology, 7(8), 742-755.

Kingma, E. M., van Duijn, E., Timman, R., van der Mast, R. C., & Roos, R. A. (2008). Behavioural problems in Huntington's disease using the Problem Behaviours Assessment. General hospital psychiatry, 30(2), 155-161.

Kung, V. W. S., Hassam, R., Morton, A. J., & Jones, S. (2007). Dopamine-dependent long term potentiation in the dorsal striatum is reduced in the R6/2 mouse model of Huntington's disease. Neuroscience, 146(4), 1571-1580.

Landwehrmeyer, B., Marder, K., Rønn, B., & Haglund, M. (2011). Effects of the Dopaminergic Stabilizer Pridopidine on Motor Symptoms in Huntington's Disease: a Meta-Analysis: 211. Clinical Genetics, 80, 48-49.

Mahant, N., McCusker, E. A., Byth, K., Graham, S., & Huntington Study Group. (2003). Huntington's disease: clinical correlates of disability and progression. Neurology, 61(8), 1085-1092.

Mangiarini, Laura, et al. Exon 1 of the HD gene with an expanded CAG repeat is sufficient to cause a progressive neurological phenotype in transgenic mice. Cell, 1996, 87.3: 493-506.

McGarry, A., et al. (2017). Effect of Pridopidine on Total Functional Capacity (TFC) in Huntington Disease (Hd): A Comparison of Open-HART Subjects with Historical Placebo Controls (p. 2. 011).

Mestre, T., Ferreira, J., Coelho, M. M., Rosa, M., & Sampaio, C. (2009). Therapeutic interventions for disease progression in Huntington's disease. Cochrane database of systematic reviews, (3).

Michl, M., Schnopfhagen, K., & Bonelli, R. M. (2013). Pridopidine in the pharmacological treatment of Huntington's disease. Clinical Investigation, 3(7), 691-699.

Millter, Marsha, 2006, "Swedish Company Announces Results of Phase II study of Dopamine Stabilizing Compound" Huntington's Disease Advocacy Center, http://www.hdac.org/features/article.php?p articleNumber=254.

Myers, R. H., et al. (1991). Factors associated with slow progression in Huntington's disease. Archives of neurology, 48(8), 800-804.

Natesan, S., et al. (2006). The dopamine stabilizers (S)-(−)-(3-methanesulfonyl-phenyl)-1-propyl-piperidine [(−)-OSU6162] and 4-(3-methanesulfonylphenyl)-1-propyl-piperidine (ACR16) show high in vivo D2 receptor occupancy, antipsychotic-like efficacy, and low potential for motor side effects in the rat. Journal of Pharmacology and Experimental Therapeutics, 318(2), 810-818.

NeuroSearch and Fleming Pederson, Feb. 3, 2010, "NeuroSearch announces positive top-line results from Phase III Huntexil® study in Huntington's disease (the MermaiHD study)".

NeuroSearch and Patrik Dahlen, Sep. 27, 2011, "NeuroSearch provides update on the Huntexil® development programme and plans a comprehensive restructuring of the company's operations".

Neurosearch, May 28, 2012, "NeuroSearch A/S reports conclusions from the Multiple Ascending Dose study (MAD) with Huntexil®".

NewsHD, "Sorry folks, the Pride-HD trial did Not show that Pridopidine slows the progression of Huntington's disease," Oct. 1, 2016, http://www.newshd.net/hdbuzz/9617/sorry-folks-the-pride-hd-trial-did-not-show-that-pridopidine-slows-the-progression-of-huntingtons-disease/.

NewsHD, "Teva Announces Results from Exploratory 52-Week Phase 2 Pride-HD Study of Pridopidine in Huntington Disease," Sep. 19, 2016, http://www.newshd.net/important/9571/teva-announces-results-from-exploratory-52-week-phase-2-pride-hd-study-of-pridopidine-huntington-disease/.

Nieoullon, A., & Coquerel, A. (2003). Dopamine: a key regulator to adapt action, emotion, motivation and cognition. Current Opinion in Neurology, 16, S3-S9.

Osterberg, O et al. (2012) "A single-center, randomized, placebo-controlled, doubleblind study to evaluate the safety" Presented at the Sixth Annual Huntington Disease Clinical Research Symposium, Neurotherapeutics, 9(1-17).

Osterberg, O et al. (2013) "A single-center, randomized, placebo-controlled, doubleblind study to evaluate the safety, tolerability, and pharmacokinetics of multiple-ascending doses of pridopidine in healthy volunteers", Abstract of Sixth Annual Huntington Disease Clinical Research Symposium, published in Neurotherapeutics, 10(1).

Paulsen, J. S., Wang et al. (2010)—Challenges assessing clinical endpoints in early Huntington disease. Movement Disorders, 25(15), pp. 2595-2603.

Peng, Qi, et al. The antidepressant sertraline improves the phenotype, promotes neurogenesis and increases BDNF levels in the R6/2 Huntington's disease mouse model. Experimental neurology, 2008, 210.1: 154-163.

PÉrez-Navarro, Esther, et al. Brain-derived neurotrophic factor, neurotrophin-3, and neurotrophin-4/5 prevent the death of striatal projection neurons in a rodent model of Huntington's disease. Journal of neurochemistry, 2000, 75.5: 2190-2199.

Pineda, José R., et al. Brain-derived neurotrophic factor modulates dopaminergic deficits in a transgenic mouse model of Huntington's disease. Journal of neurochemistry, 2005, 93.5: 1057-1068.

(56) References Cited

OTHER PUBLICATIONS

Podsiadlo, D., & Richardson, S. (1991). The timed "Up & Go": a test of basic functional mobility for frail elderly persons. Journal of the American geriatrics Society, 39(2), 142-148.
Ponten, H., et al. (2010). In vivo pharmacology of the dopaminergic stabilizer pridopidine. European journal of pharmacology, 644(1-3), 88-95.
Posner, K., et al. (2011). The Columbia-Suicide Severity Rating Scale: initial validity and internal consistency findings from three multisite studies with adolescents and adults. American journal of psychiatry, 168(12), 1266-1277.
Raffelsbauer, Diane, EHDN News, Article of the Month, Jan. 2012, Issue 15.
Rao, A. K., Muratori, L., Louis, E. D., Moskowitz, C. B., & Marder, K. S. (2009). Clinical measurement of mobility and balance impairments in Huntington's disease: validity and responsiveness. Gait & posture, 29(3), 433-436.
Reuben, D. B., & Siu, A. L. (1990). An objective measure of physical function of elderly outpatients: the Physical Performance Test. Journal of the American Geriatrics Society, 38(10), 1105-1112.
Simmons, Danielle A., et al. Up-regulating BDNF with an ampakine rescues synaptic plasticity and memory in Huntington's disease knockin mice. Proceedings of the National Academy of Sciences, 2009, 106.12: 4906-4911.
Slow, Elizabeth J., et al. Selective striatal neuronal loss in a YAC128 mouse model of Huntington disease. Human molecular genetics, 2003, 12.13: 1555-1567.
Spires, Tara L., et al. Environmental enrichment rescues protein deficits in a mouse model of Huntington's disease, indicating a possible disease mechanism. Journal of Neuroscience, 2004, 24.9: 2270-2276.
Squitieri, F. et al. (2015). Profile of pridopidine and its potential in the treatment of Huntington disease: the evidence to date. Drug design, development and therapy, 9, 5827.
Squitieri, Ferdinando, et al. Pridopidine, a dopamine stabilizer, improves motor performance and shows neuroprotective effects in Huntington disease R6/2 mouse model. Journal of cellular and molecular medicine, 2015, 19.11: 2540-2548.
Strand, Andrew D., et al. Expression profiling of Huntington's disease models suggests that brain-derived neurotrophic factor depletion plays a major role in striatal degeneration. Journal of Neuroscience, 2007, 27.43: 11758-11768.
Stroop, J. R. (1935). Studies of interference in serial verbal reactions. Journal of experimental psychology, 18(6), 643.
Waters, S, et al., (2009), Medical Treatments. Pharmacology of the dopaminergic stabilizer pridopidine (ACR16). Clinical Genetics—76(S1):74. (Abstract D10).
Xie, Yuxiang; Hayden, Michael R.; Xu, Baoji. BDNF overexpression in the forebrain rescues Huntington's disease phenotypes in YAC128 mice. Journal of Neuroscience, 2010, 30.44: 14708-14718.
Yung-Chi, Cheng; Prusoff, William H. Relationship between the inhibition constant (KI) and the concentration of inhibitor which causes 50 per cent inhibition (I50) of an enzymatic reaction. Biochemical pharmacology, 1973, 22.23: 3099-3108.
Zhan, L., et al. (2011). Altered expression and coregulation of dopamine signalling genes in schizophrenia and bipolar disorder. Neuropathology and applied neurobiology, 37(2), 206-219.
Zielonka, D. et al. (2015). Update on Huntington's disease: advances in care and emerging therapeutic options. Parkinsonism & related disorders, 21(3), 169-178.
Zuccato, Chiara, et al. Loss of huntingtin-mediated BDNF gene transcription in Huntington's disease. Science, 2001, 293.5529: 493-498.
Zuccato, Chiara; Cattaneo, Elena. Brain-derived neurotrophic factor in neurodegenerative diseases. Nature Reviews Neurology, 2009, 5.6: 311.
Zuccato, Chiara; Cattaneo, Elena. Role of brain-derived neurotrophic factor in Huntington's disease. Progress in neurobiology, 2007, 81.5-6: 294-330.
Reilmann, R., et al. (2024). Safety and efficacy of laquinimod for Huntington's disease (LEGATO-HD): a multicentre, randomised, double-blind, placebo-controlled, phase 2 study. The Lancet Neurology, 23(3), 243-255.
Naoi, M., et al. (2022). Neuroprotective function of rasagiline and selegiline, inhibitors of type B monoamine oxidase, and role of monoamine oxidases in synucleinopathies. International Journal of Molecular Sciences, 23(19), 11059.
Nayak, L, & Henchcliffe, C. (2008). Rasagiline in treatment of Parkinson's disease. Neuropsychiatric Disease and Treatment, 4(1), 23-32.
Rascol, O., et al. (2005). Rasagiline as an adjunct to levodopa in patients with Parkinson's disease and motor fluctuations (LARGO, Lasting effect in Adjunct therapy with Rasagiline Given Once daily, study): a randomised, double-blind, parallel-group trial. The Lancet, 365(9463), 947-954.

* cited by examiner

PRIDOPIDINE FOR TREATING HUNTINGTON'S DISEASE

CROSS REFERENCE TO RELATED APPLICATIONS

This Application is a Continuation Application from U.S. application Ser. No. 16/438,508 filed Jun. 12, 2019, which is a Continuation in Part of U.S. patent application Ser. No. 14/309,111 filed on Jun. 19, 2014, which claims the benefit of U.S. Provisional Application No. 61/837,928, filed Jun. 21, 2013, and U.S. Provisional Application No. 61/877,832, filed Sep. 13, 2013, which are all incorporated in their entirety herein by reference.

Throughout this application, various publications are referred to by first author and year of publication. Full citations for these publications are presented in a References section immediately before the claims. Disclosures of the publications cited in the References section are hereby incorporated by reference in their entireties into this application in order to more fully describe the state of the art as of the date of the invention described herein.

BACKGROUND OF INVENTION

Huntington's Disease

Huntington's disease (HD) is a fatal neurodegenerative disorder with an autosomal dominant mode of inheritance. The disease is associated with a triad of motor, behavioral, and cognitive symptoms. Motor disturbances are the defining feature of the disease, with chorea the most evident motor symptom. Although useful for diagnosis, chorea is a poor marker of disease severity. Rather, disability and disease severity best correlate with negative motor features such as impairment in fine motor skills, bradykinesia, and gross motor coordination skills, including speech difficulties, gait, and postural dysfunction (Mahant 2003).

Dopamine is widely regarded as an important neurotransmitter modulating several aspects of brain functions including motor function. (Nieoullon 2003) A disrupted dopaminergic signaling has been implicated in a number of neurological and psychiatric conditions, (Zhan 2011, Dunlop 2007) and there is considerable clinical and preclinical evidence suggesting that dopaminergic functions are also compromised in HD. (Kung 2007, Huot 2007)

A number of medications are prescribed to ameliorate the motor and emotional problems associated with HD; however, the scientific evidence for the usefulness of various drugs in HD is poor. (Mestre 2009 CD006455, Mestre 2009 CD006456) Only 1 drug, tetrabenazine, which reduces dopamine availability and transmission, is registered specifically for the treatment of patients with HD for the management of chorea. No registered drugs are available for the management of the multifaceted motor symptoms. As such, there is a significant unmet medical need to develop medications to ameliorate symptoms of HD.

Pridopidine

Pridopidine (4-[3-(methylsulfonyl)phenyl]-1-propyl-piperidine) (formerly known as ACR 16) is a drug under development from a new class of pharmaceutical agents, the dopidines, which are considered to have dopaminergic stabilizing properties. Dopaminergic stabilizers are compounds that can both enhance and counteract dopamine dependent functions in the central nervous system (CNS), depending on the initial level of dopaminergic activity. Dopaminergic stabilizers suppress the hyperactive behavior induced by stimulants such as amphetamine. In contrast, at low levels of dopamine function, the dopamine stabilizers enhance behavioral activity. The primary effect of pridopidine on HD-related motor symptoms is therefore expected to occur via the dopamine transmissions modulating properties of pridopidine. (Ponten 2010)

BRIEF SUMMARY OF THE INVENTION

This invention provides a method of treating a human patient afflicted with Huntington's disease, comprising periodically orally administering to the patient a pharmaceutical composition comprising pridopidine, its analog or a pharmaceutically acceptable salt thereof such that greater than 135 mg of pridopidine is administered to the patient per day This invention further provides a method of treating a human patient afflicted with Huntington's disease, comprising periodically orally administering to the patient a pharmaceutical composition comprising pridopidine hydrochloride such that greater than 90 mg of pridopidine is administered to the patient per day.

This invention is directed to a method of reducing impairment of functional capacity of a human patient afflicted with Huntington's disease, comprising orally administering to the human patient a pharmaceutical composition comprising pridopidine, its analog or a pharmaceutically acceptable salt thereof, thereby reduce impairment of functional capacity of the human patient.

BRIEF DESCRIPTION OF THE SEVERAL VIEWS OF THE DRAWINGS

The present invention is further illustrated by reference to the accompanying drawings.

DETAILED DESCRIPTION OF THE INVENTION

Figure 1:
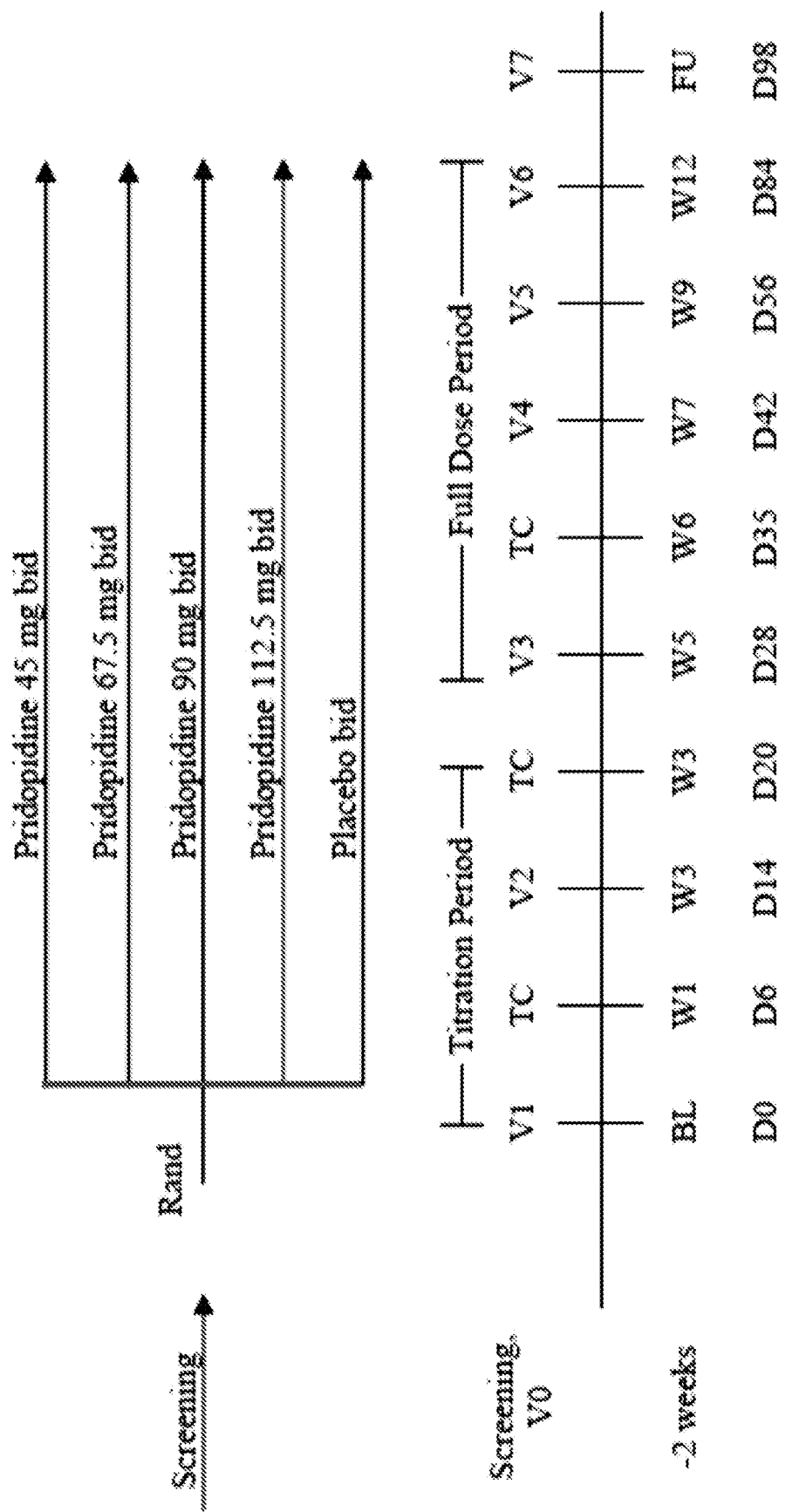
FIG. 1: Overall Study Schema of Example 1.

This invention provides a method of treating a human patient afflicted with Huntington's disease, comprising periodically orally administering to the patient a pharmaceutical composition comprising pridopidine, its analog or a pharmaceutically acceptable salt thereof such that greater than 135 mg of pridopidine is administered to the patient per day.

In an embodiment, 180 mg or 225 mg of pridopidine is administered to the patient per day. In another embodiment, 135 mg, 180 mg or 225 mg of pridopidine is administered to the patient per day.

In an embodiment, a unit dose of the pharmaceutical composition contains 90 mg or 112.5 mg of pridopidine. In another embodiment, a unit dose of the pharmaceutical composition contains 67.5 mg, 90 mg, or 112.5 mg of pridopidine.

This invention further provides a method of treating a human patient afflicted with Huntington's disease, comprising periodically orally administering to the patient a pharmaceutical composition comprising pridopidine hydrochloride such that greater than 90 mg of pridopidine is administered to the patient per day.

In an embodiment of the methods of the invention, the pharmaceutical composition is administered twice per day.

In an embodiment of the methods of the invention, an equal amount of the pharmaceutical composition is administered at each administration.

In an embodiment of the methods of the invention, the pharmaceutical composition is administered for at least 12 weeks. In another embodiment of the methods of the invention, the pharmaceutical composition is administered for at least 26 weeks.

In an embodiment of the methods of the invention, treating comprises reducing one or more symptoms of Huntington's disease. In an embodiment, the one or more symptoms are selected from the group consisting of depression, anxiety, motor function impairment, cognitive impairment, a physical symptom, a mental symptom, an emotional symptom, a behavioral symptom, impairment of the patient's functional capacity and reduced lifespan.

In an embodiment, the one or more symptoms are measured by the Clinician's Interview-based Impression of Change plus Caregiver Input (CIBIC-Plus), Physical Disability Score (PDS), Unified Huntington's Disease Rating Scale (UHDRS) Functional Assessment (FA), Clinical Global Impression of Change (CGI-C), Unified Huntington's Disease Rating Scale (UHDRS) Total Functional Capacity (TFC), Unified Huntington's Disease Rating Scale (UHDRS) Independence Score (IS), HD-Quality of Life scale (HD-QoL), Multiple Sclerosis Walking Scale (MSWS-12), Physical Performance Test (PPT), hand movement score, gait and balance score, Quantitative motor (Q-Motor) assessment, timed up and go (TUG) assessment, cognitive assessment battery (CAB), symbol digit modalities test (SDMT), Stroop word reading test, abbreviated Montreal cognitive assessment (MoCA) scale, Trail Making Test B assessment, or Problem Behaviors Assessment-Short form (PBA-s). In another embodiment, the one or more symptoms are measured by EQ5D-5L, Walk-12, or Modified Physical Performance Test (mPPT).

In an embodiment of the methods of the invention, treating comprises reducing the patient's motor impairment symptoms which are measured by the Unified Huntington's Disease Rating Scale (UHDRS) Total Motor Score (TMS).

In an embodiment of the methods of the invention, treating comprises reducing the patient's motor impairment symptoms which are measured by the Unified Huntington's Disease Rating Scale (UHDRS)-Chorea score.

In an embodiment of the methods of the invention, wherein treating comprises reducing the patient's motor impairment symptoms which are measured by the Unified Huntington's Disease Rating Scale (UHDRS)-Dystonia score.

In an embodiment of the methods of the invention, treating comprises reducing the patient's motor impairment symptoms which are measured by the Unified Huntington's Disease Rating Scale (UHDRS) modified Motor Score (mMS).

In an embodiment of the methods of the invention, the patient is at least 21 years old. In another embodiment of the methods of the invention, the patient is less than 30 years old.

In an embodiment, the methods further comprise a step of determining whether the patient is at least 21 years old, and periodically orally administering the pharmaceutical composition to the patient if the patient is at least 21 years old. In another embodiment, the methods further comprise a step of determining whether the patient is less than 30 years old, and periodically orally administering the pharmaceutical composition to the patient if the patient is less than 30 years old.

In an embodiment, the methods further comprise a step of determining whether the patient is at least 21 years old and less than 30 years old, and periodically orally administering the pharmaceutical composition to the patient if the patient is at least 21 years old and less than 30 years old.

In an embodiment of the methods of the invention, the patient has a UHDRS-TMS score ≥25 before beginning treatment.

In an embodiment of the methods of the invention, the patient has a UHDRS-IS below 90% before beginning treatment.

In an embodiment of the methods of the invention, the patient has ≥36 CAG repeats in the Huntingtin gene.

The invention further provides a pharmaceutical composition comprising 112.5 mg of pridopidine or a pharmaceutically acceptable salt thereof and one or more adjuvants, excipients, carriers and/or diluents.

In an embodiment, the pridopidine or a pharmaceutically acceptable salt thereof is pridopidine hydrochloride. In another embodiment, the pridopidine or a pharmaceutically acceptable salt thereof is pridopidine hydrobromide.

In an embodiment, the pharmaceutical composition comprises silicified microcrystalline cellulose and magnesium stearate as excipients.

The invention further provides a pharmaceutical composition comprising pridopidine or a pharmaceutically acceptable salt thereof for use in treating a human patient afflicted with Huntington's disease, wherein the pharmaceutical composition is to be periodically orally administered to the patient such that greater than 135 mg of pridopidine is administered to the patient per day.

In an embodiment, 180 mg or 225 mg of pridopidine is to be administered to the patient per day.

In an embodiment, a unit dose of the pharmaceutical composition contains 90 mg or 112.5 mg of pridopidine.

The invention further provides a pharmaceutical composition comprising pridopidine hydrochloride for use in treating a human patient afflicted with Huntington's disease, wherein the pharmaceutical composition is to be periodically orally administered to the patient such that greater than 90 mg of pridopidine is administered to the patient per day.

In an embodiment, 135 mg, 180 mg or 225 mg is to be administered to the patient per day.

In an embodiment, a unit dose of the pharmaceutical composition contains 67.5 mg, 90 mg, or 112.5 mg of pridopidine.

In an embodiment, the pharmaceutical composition is to be administered twice per day.

In an embodiment, an equal amount of the pharmaceutical composition is to be administered at each administration.

In an embodiment, the pharmaceutical composition is formally administered for at least 12 weeks. In another embodiment, the pharmaceutical composition is formally administered for at least 26 weeks.

In an embodiment, treating comprises reducing one or more symptoms of Huntington's disease.

In an embodiment, the one or more symptoms are selected from the group consisting of depression, anxiety, motor function impairment, cognitive impairment, a physical symptom, a mental symptom, an emotional symptom, a behavioral symptom, impairment of the patient's functional capacity and reduced lifespan.

In an embodiment, the one or more symptoms are measured by the Clinician's Interview-based Impression of Change plus Caregiver Input (CIBIC-Plus), Physical Disability Score (PDS), Unified Huntington's Disease Rating Scale (UHDRS) Functional Assessment (FA), Clinical Global Impression of Change (CGI-C), Unified Huntington's Disease Rating Scale (UHDRS) Total Functional Capacity (TFC), Unified Huntington's Disease Rating Scale (UHDRS) Independence Score (IS), HD-Quality of Life scale (HD-QoL), Multiple Sclerosis Walking Scale (MSWS- 12), Physical Performance Test (PPT), hand movement score, gait and balance score, Quantitative motor (Q-Motor) assessment, timed up and go (TUG) assessment, cognitive assessment battery (CAB), symbol digit modalities test (SDMT), Stroop word reading test, abbreviated Montreal cognitive assessment (MoCA) scale, Trail Making Test B assessment, or Problem Behaviors Assessment-Short form (PBA-s). In another embodiment, the one or more symptoms are measured by EQSD-5L, Walk-12, or Modified Physical Performance Test (mPPT).

In an embodiment, treating comprises reducing the patient's motor impairment symptoms which are measured by the Unified Huntington's Disease Rating Scale (UHDRS) Total Motor Score (TMS).

In an embodiment, treating comprises reducing the patient's motor impairment symptoms which are measured by the Unified Huntington's Disease Rating Scale (UHDRS) modified Motor Score (mMS).

In an embodiment, treating comprises reducing the patient's motor impairment symptoms which are measured by the Unified Huntington's Disease Rating Scale (UHDRS)-Chorea score.

In an embodiment, treating comprises reducing the patient's motor impairment symptoms which are measured by the Unified Huntington's Disease Rating Scale (UHDRS)-Dystonia score.

In an embodiment, the pharmaceutical composition is to be administered to a patient who is at least 21 years old. In another embodiment, the pharmaceutical composition is to be administered to a patient who is less than 30 years old.

In an embodiment, the pharmaceutical composition is to be administered to a patient who has a UHDRS-TMS score ≥25 before beginning treatment.

In an embodiment, the pharmaceutical composition is to be administered to a patient who has a UHDRS-IS below 90% before beginning treatment.

In an embodiment, the pharmaceutical composition is to be administered to a patient who has ≥36 CAG repeats in the Huntingtin gene.

The invention further provides a use of an amount of pridopidine, its analog or a pharmaceutically acceptable salt thereof in the preparation of a medicament for treating a human patient afflicted with Huntington's disease, wherein the medicament is formulated for periodic oral administration to the patient such that greater than 135 mg of pridopidine is administered to the patient per day.

In an embodiment, the medicament is formulated for periodic oral administration to the patient such that 180 mg or 225 mg of pridopidine is administered to the patient per day.

In an embodiment, the medicament is formulated to contain 90 mg or 112.5 mg of pridopidine.

The invention further provides a use of an amount of pridopidine hydrochloride in the preparation of a medicament for treating a human patient afflicted with Huntington's disease, wherein the medicament is formulated for periodic oral administration to the patient such that greater than 90 mg of pridopidine is administered to the patient per day.

In an embodiment, the medicament is formulated for periodic oral administration to the patient such that 135 mg, 180 mg, or 225 mg of pridopidine is administered to the patient per day.

In an embodiment, the medicament is formulated to contain 67.5 mg, 90 mg, or 112.5 mg of pridopidine.

In an embodiment, the medicament is formulated for twice a day administration.

In an embodiment, treating comprises reducing one or more symptoms of Huntington's disease.

In an embodiment, the one or more symptoms are selected from the group consisting of depression, anxiety, motor function impairment, cognitive impairment, a physical symptom, a mental symptom, an emotional symptom, a behavioral symptom, impairment of the patient's functional capacity and reduced lifespan.

In an embodiment, the one or more symptoms are measured by the Clinician's Interview-based Impression of Change plus Caregiver Input (CIBIC-Plus), Physical Disability Score (PDS), Unified Huntington's Disease Rating Scale (UHDRS) Functional Assessment (FA), Clinical Global Impression of Change (CGI-C), Unified Huntington's Disease Rating Scale (UHDRS) Total Functional Capacity (TFC), Unified Huntington's Disease Rating Scale (UHDRS) Independence Score (IS), HD-Quality of Life scale (HD-QoL), Multiple Sclerosis Walking Scale (MSWS-12), Physical Performance Test (PPT), band movement score, gait and balance score, Quantitative motor (Q-Motor) assessment, timed up and go (TUG) assessment, cognitive assessment battery (CAB), symbol digit modalities test (SDMT), Stroop word reading test, abbreviated Montreal cognitive assessment (MoCA) scale, Trail Making Test B assessment, or Problem Behaviors Assessment-Short form (PBA-s). In another embodiment, the one or more symptoms are measured by EQ5D-SL, Walk-12, or Modified Physical Performance Test (mPPT).

In an embodiment, treating comprises reducing the patient's motor impairment symptoms which are measured by the Unified Huntington's Disease Rating Scale (UHDRS) Total Motor Score (TMS).

In an embodiment, treating comprises reducing the patient's motor impairment symptoms which are measured by the Unified Huntington's Disease Rating Scale (UHDRS) modified Motor Score (mMS)

In an embodiment, treating comprises reducing the patient's motor impairment symptoms which are measured by the Unified Huntington's Disease Rating Scale (UHDRS)-Chorea score.

In an embodiment, treating comprises reducing the patient's motor impairment symptoms which are measured by the Unified Huntington's Disease Rating Scale (UHDRS)-Dystonia score.

In an embodiment, the medicament is formulated for administration to a patient who is at least 21 years old. In another embodiment, the medicament is formulated for administration to a patient who is less than 30 years old.

In an embodiment, the medicament is formulated for administration to a patient who has a UHDRS-TMS score ≥25 before beginning treatment.

In an embodiment, the wherein the medicament is formulated for administration to a patient who has a UHDRS-IS below 90% before beginning treatment.

In an embodiment, the medicament is formulated for administration to a patient who has ≥36 CAG repeats in the Huntingtin gene.

Combinations of the above-described embodiments are also within the scope of the invention.

Pharmaceutically Acceptable Salts

The active compounds for use according to the invention may be provided in any form suitable for the intended administration. Suitable forms include pharmaceutically (i.e. physiologically) acceptable salts, and pre-or prodrug forms of the compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Pridopidine Analogs

In one embodiment, as used herein "pridopidine" refers to pridopidine and combination with one or more analogs thereof. In one embodiment, the analogs of pridopidine are represented by the following structures:

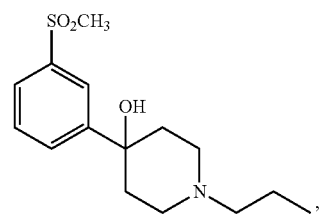
(1)

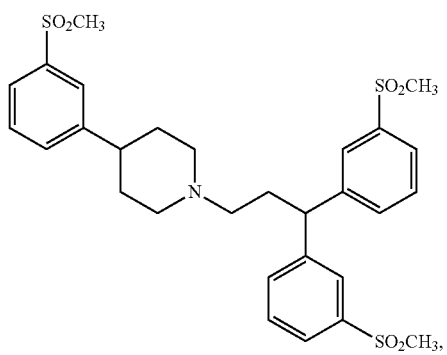
(2)

(3)

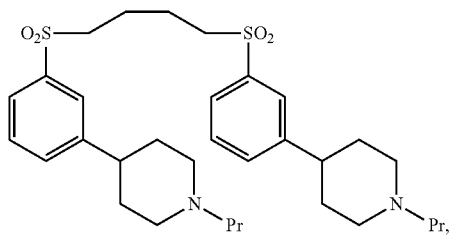

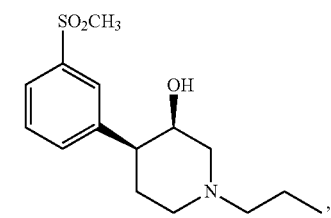
(4)

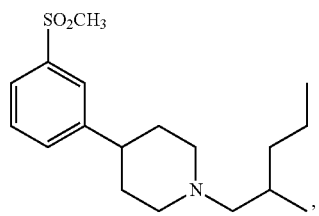(5)

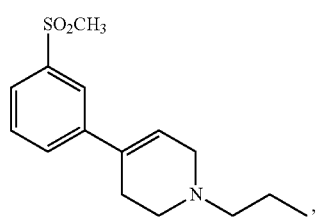(6)

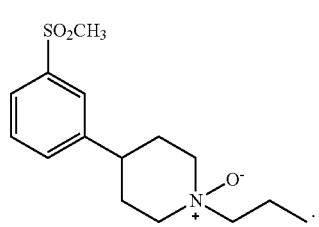(7)

Pharmaceutical Compositions

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries.

In an embodiment, the invention provides pharmaceutical compositions comprising the active compound, its analog or pharmaceutically acceptable salt or derivative thereof, together with one or more pharmaceutically acceptable carriers therefore, and, optionally, other therapeutic and/or prophylactic ingredients know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, PA).

As used herein, "effective" as in an amount effective to achieve an end means the quantity of a component that is sufficient to yield an indicated therapeutic response without undue adverse side effects (such as toxicity, irritation, or allergic response) commensurate with a reasonable benefit/ risk ratio when used in the manner of this disclosure. For example, an amount effective to treat a movement disorder. The specific effective amount varies with such factors as the particular condition being treated, the physical condition of the patient, the type of mammal being treated, the duration of the treatment, the nature of concurrent therapy (if any), and the specific formulations employed and the structure of the compounds or its derivatives.

As used herein, an amount of pridopidine as measured in milligrams refers to the milligrams of pridopidine (4-[3-(methylsulfonyl)phenyl]-1-propyl-piperidine) present in a preparation, regardless of the form of the preparation. For example, a unit dose containing "90 mg pridopidine" means the amount of pridopidine in a preparation is 90 mg, regardless of the form of the preparation. Thus, when in the form of a salt, e.g. pridopidine hydrochloride, the weight of the salt form necessary to provide a dose of 90 mg pridopidine would be greater than 90 mg due to the presence of the salt.

As used herein, to "treat" or "treating" encompasses, e.g., reducing a symptom, inducing inhibition, regression, or stasis of the disorder and/or disease. As used herein, "inhibition" of disease progression or disease complication in a subject means preventing or reducing the disease progression and/or disease complication in the subject.

Listing of Abbreviations and Definitions of Terms

The following abbreviations are used throughout this application:

AE: adverse event; ALT: alanine aminotransferase; AR: Autoregressive; Arc mRNA: activity-regulated cytoskeleton-associated protein messenger ribonucleic acid; ARH: Heterogeneous Autoregressive; AST: aspartate aminotransferase; AUC: area under the concentration-time curve; Bid: twice daily; BL=Baseline; CAB: cognitive assessment battery; CAG: cytosine-adenosine-guanine; CDMS: clinical data management system; CFR: Code of Federal Regulations; CGI-C: Clinical Global Impression of Change; CGI-S: Clinical Global Impression of Severity; CI: confidence interval; CIBIC-Plus: Clinician's Interview-based Impression of Change plus Caregiver Input; CIBIS: Clinician's Interview-based Impression of Severity; CIOMS: Council for International Organizations of Medical Sciences; Cmax: maximum observed plasma drug concentration; CNS: central nervous system; CRF: case report form; CRO: contract research organization; CS: Compound Symmetry; CSH: Heterogeneous Compound Symmetry; C-SSRS: Columbia-Suicide Severity Rating Scale; CYP: cytochrome P450; DSM-IV TR: Diagnostic and Statistical Manual-Fourth Edition Text Revision; ECG: electrocardiogram; EM: extensive metabolizers; EU: European Union; FA: Functional Assessment; FAS: full analysis set; FDA: US Food and Drug Administration; Freq: tapping frequency; GCP: Good Clinical Practice; GFV-C: grip force variability in the static phase; GGT: gamma-glutamyl transpeptidase; HART: Huntington's disease ACR16 Randomized Trial; HCG: human chorionic gonadotropin; HD: Huntington's disease; HD-QoL=Huntington's disease Quality of Life; ICH: International Conference on Harmonisation; IEC: Independent Ethics Committee; IOI: inter onset interval; IPI: inter peak interval; IRB: Institutional Review Board; IRT: interactive response technology; IS: Independence Score; ITI: inter tap interval; ITT: intent-to-treat; LSO: local safety officer; MAD: multiple ascending dose; MedDRA: Medical Dictionary for Regulatory Activities; MermaiHD: Multinational European Multicentre ACR16 study in Huntington's Disease; ML: Maximum-Likelihood; mMS: Modified Motor Score; MoCA: Montreal cognitive assessment; MS: Multiple sclerosis; MSWS-12: Multiple Sclerosis Walking Scale; MTD: maximum tolerated dose; NMDA: N-methyl-D-aspartate; NOAEL: no observed adverse effect level; PBA-s: Problem Behaviors Assessment-Short form; PD: pharmacodynamic(s); PDS: Physical disability scale; PK: pharmacokinetic(s); PM: poor metabolizer; PPT: physical performance test; Qd: once daily; Q-Motor: Quantitative motor; QoL: Quality of life; QTcF: Fridericia-corrected QT interval; RBC: red blood cell; REML: Restricted Maximum-Likelihood; SAE: serious adverse event; SD: standard deviation; SDMT: symbol digit modalities test; SOC: system organ class; SOP: standard operating procedure, SUSAR: suspected unexpected serious adverse reaction; t½: half life; TC=telephone call; TD: tap duration; TF: tapping force; TFC: Total functional capacity; TMS: Total Motor Score; TUG: timed up an go; UHDRS: Unified Huntington's Disease Rating Scale; ULN: upper limit of the normal range; US: United States; WBC: white blood cell; WHO: World Health Organization; WHO: Drug World Health Organization (WHO) drug dictionary: AHR: change from baseline in heart rate; ΔQTcF: change from baseline in QTcF; ΔΔHR: placebo-corrected change from baseline in heart rate; Placebo-Controlled Study-Huntington's Disease; ΔΔQTcF: placebo-corrected change from baseline in QTcF Clinical Studies Sixteen (16) clinical studies have been completed with pridopidine, comprising 8 studies in healthy subjects (of which 1 study also included patients with schizophrenia), 1 study in patients with Parkinson's disease, 2 studies in patients with schizophrenia (including the study mentioned above), and 6 studies in patients with HD (including 1 open-label extension study). In addition, a compassionate use program for pridopidine in patients with HD is ongoing in Europe, and an open-label, long term safety study is ongoing in the United States (US) and Canada. As per May 1, 2013, 853 patients with HD have been enrolled in clinical studies with pridopidine, with 621 patients receiving pridopidine in doses ranging from 20 to 90 mg daily.

Three randomized, double-blind, placebo-controlled, parallel-group clinical studies investigating the efficacy and safety of pridopidine in patients with HD have been conducted. Study ACR16C007 explored the efficacy of 44 mg pridopidine once daily (qd) in 58 patients. Subsequently, the "Huntington's disease ACR16 Randomized Trial" (HART) study (ACR16C009) was designed to explore the dose-response of pridopidine looking at 3 different daily doses (10, 22.5, and 45 mg twice daily [bid]) in 227 patients during 12 weeks of treatment. In parallel, the "Multinational European Multicentre ACR16 study in Huntington's Disease" (MermaiHD) study (ACR16C008) investigated the efficacy and safety of 45 mg given qd and bid over 26 weeks of treatment in 437 patients.

The HART study (ACR16C009) demonstrated dose-dependent efficacy of pridopidine in treating motor symptoms in HD, measured using the Modified Motor Score (mMS) and Total Motor Score (TMS) from the Unified Huntington's Disease Rating Scale (UHDRS). In the HART and MermaiHD (ACR16C008) studies, there was a trend for effect on mMS on the 45 mg bid dose, which did not reach the pre-specified significance criteria. However, statistically significant findings on the TMS were found in both HART and MermaiHD studies. The motor effects seen are congruent with the perceived mode of action of pridopidine. The UHDRS-TMS and its subscales have been used in clinical studies for other compounds investigated in HD. The effect of 2.8 to 3 points on the UHDRS-TMS (from a baseline of 34 to 43 points across treatment groups in the MermaiHD [ACR16C008] and HART [ACR16C009] studies) is comparable to the effect size observed in the pivotal study of tetrabenazine TETRA-HD, which is the only FDA-approved treatment for Huntington's disease-associated symptoms (specifically chorea). In addition, it is comparable to the effect size expected in other major studies of medications aimed at symptomatic relief of motor symptoms associated with HD, namely the RID-HD and TREND-HD studies:

The pivotal study of tetrabenazine (103,004/TETRA-HD), the only Food and Drug Administration (FDA)-approved treatment for HD-associated symptoms (specifically chorea), showed a borderline significant improvement of 3.3 points on the UHDRS-TMS (p=0.075; 45 to 47 points at baseline). The improvement induced by treatment with tetrabenazine was entirely attributable to improvement of chorea and no significant effect was observed on other motor components. The study was powered to detect a 2.7-point improvement in total chorea score (which constitutes the chorea items on the TMS) and a neutral effect on other UHDRS-TMS items. (Huntington Study Group 2006).

The RID-HD study of riluzole was powered to the same effect size (2.8 points on the total chorea score). (Huntington Study Group 2003).

The TREND-HD study of ethyl-eicosapentaenoic acid used as its primary endpoint a modified version of the UHDRS-TMS (TMS-4, encompassing chorea, dystonia and ocular pursuit). The study was powered to detect an effect size of 2.7 to 3.2 (depending on cytosine-adenosine-guanine [CAG] repeat length). (Huntington Study Group 2008).

The most frequently reported adverse events (AEs) in patients with HD in the placebo-controlled studies with pridopidine (ACR16C007, MermaiHD [ACR16C008], and HART [ACR16C009]) were fall, diarrhea, nausea, nasopharyngitis and Huntington's chorea. Pridopidine was generally well tolerated, with an AE profile similar to placebo. Apart from transient increases in pulse rate and prolactin plasma levels, no clinically significant changes or trends were observed for vital signs and/or laboratory parameters. Electrocardiogram (ECG) assessment, including assessment of cardiac repolarization, demonstrated no clinically significant effects of Pridopidine on the ECG in HD patients. Overall the frequencies of AEs and serious adverse events (SAEs) were similar between the placebo group (58.6% and 5.2%) and the combined active group (61.2% and 4.9%). Discontinuation rate was also similar between the placebo group and the active group (8.2% and 9.2%). Four patients had an AE with fatal outcome; 2 patients treated with placebo, and 2 patients treated with pridopidine. The fatal events in the patients treated with pridopidine were assessed as unrelated to study medication.

The long-term safety has been examined in 2 open-label extension studies (completed ACR16C008-OLP and ongoing ACR16C015-open HART). Generally, the safety profiles in the open-label extensions were similar to those seen in the previous randomized placebo-controlled studies with pridopidine. To date (June 2013), 5 cases with fatal outcome have been reported in the open-label extensions of the MermaiHD and the HART studies. The deaths occurring in patients treated with pridopidine were considered unrelated to pridopidine (subarachnoid hemorrhage, urosepsis, completed suicide, aspiration pneumonia, death of unknown cause, and myocardial infarction).

Clinical Pharmacology Studies

Pridopidine has a relatively fast and almost complete absorption after oral administration, with individual maximum concentration (Cmax) values occurring between 0.5 to 4 hours after dosing (median of 1.25 to 2 hours). Food intake has no impact on the extent of absorption of pridopidine After absorption, pridopidine is eliminated partly by urinary excretion and partly by hepatic metabolism (primarily via the cytochrome P450 [CYP] 2D6 pathway), with mean half life (t½) of approximately 10 hours at steady state. In extensive metabolizers (EMs), pridopidine is metabolized by CYP2D6 to 1 main metabolite (TV-45065, previously known as ACR30); the contribution from other enzymatic pathways does not seem to be significant. Conversely, poor metabolizers (PM) depend on renal excretion as their main elimination pathway.

In a dedicated PK study, the Cmax and AUC in PMs compared with EMs is approximately 1.6- and 2.8-fold higher after a single bid dosing day, respectively. At steadystate, however, this difference is reduced to 1.3-fold for both Cmax and AUC. A population PK model confirmed that, due to auto-inhibition of CYP2D6 in Ems, clearance in EMs and PMs approach each other at steady state, but they still differ significantly (9.22 L/h or 6.30 L/h in a typical EM or PM subject weighing 60 kg). Due to this auto-inhibition of CYP2D6, the fraction metabolized decreases with multiple doses, and renal elimination becomes a more important elimination pathway than the polymorphic CYP2D6 metabolism. Renal clearance of pridopidine at steady state ranges from 90 to 116 mL/min which corresponds well to the glomerular filtration rate.

In a dedicated PK study, the Cmax and AUC in PMs compared with EMs is approximately 1.6-fold higher and 2.8-fold higher after a single bid dosing day, respectively. At steady-state, however, this difference is reduced to 1.3-fold for both Cmax and AUC.

A population PK model confirmed that, due to auto-inhibition of CYP2D6 in EMs, clearance in EMs and PMs approach each other at steady state, but they still differ significantly (9.22 L/h or 6.30 L/h in a typical EM or PM subject weighing 60 kg) (Exploratory Population 2012). Due to auto-inhibition of CYP2D6, the fraction metabolized decreases with multiple doses, and renal elimination becomes a more important elimination pathway than the polymorphic CYP2D6 metabolism. Renal clearance of pridopidine at steady state ranges from 90 to 116 mL/min which corresponds well to the glomerular filtration rate.

In a multiple ascending dose (MAD) study (ACR16C018), tolerability and safety of Pridopidine 45 to 90 mg bid for 9 days was investigated in 36 healthy subjects. The safety profile of pridopidine in the 45 and 67.5 mg bid dose groups was similar to that observed in the larger clinical studies. Overall, the most frequently reported AEs were within the system organ classes (SOCs) Nervous system disorders, Gastrointestinal disorders and Psychiatric disorders. Psychiatric symptoms and signs, such as nightmare, aggression, depressive mood, anxiety, and abnormal dreams were reported only at the 90 mg bid dose level and they were all considered related to treatment. Frequency of dizziness was markedly increased with pridopidine dose (50% and 35% of the subjects in the 90 and 67.5 mg bid arms respectively, versus 11% and 14% in the 45 mg bid and placebo arm, respectively). The 90 mg bid dose was considered the maximum tolerated dose (MTD) in the multiple ascending dose (MAD) study.

An effect of pridopidine on the QT interval duration that may be of clinical concern has been observed in healthy subjects. Results of the ACR16C018 study revealed a dose-dependent Fridericia-corrected QT interval (QTcF) prolongation, with a mean placebo-corrected change from baseline in QTcF (ΔΔQTcF) of up to 24.8 msec in the 90 mg bid dose group on Day 9, observed 1 hour after study drug morning dose, corresponding to the time for Cmax.

Following multiple dosing of 45, 67.5 and 90 mg bid in healthy subjects, dose proportionality was apparent for area under the concentration time curve (AUC) and Cmax. No information is available for higher doses, however linear pharmacokinetics (PK) are expected because of the low probability of oral absorption saturation (average 98% absolute bioavailability) and low probability of major elimination route at steady state (passive renal excretion of unchanged drug)

In a study with healthy volunteers with mild to moderate renal impairment, mild renal impairment did not affect the steady state pharmacokinetics of pridopidine; however, subjects with moderate renal impairment had higher AUC and Cmax values than matching healthy subjects at steady state. Studies in patients with hepatic impairment have not been performed, and PMs represent a worst-case scenario for hepatic impairment.

Pridopidine is a CYP2D6 substrate and thus PK interactions can be expected with drugs that inhibit CYP2D6, although not more than what is expected from a PM. Pridopidine is also a strong CYP2D6 inhibitor, and so drug-drug interactions with co-administered CYP2D6 substrates are anticipated.

Drugs and Dosages

Studies MermaiHD (ACR16C008) and HART (ACR16C009) have shown that a Pridopidine 45 mg bid dose is associated with improvement in UHDRS-TMS (of approximately 3 points relative to placebo) and motor domain subscores hereof, with no aggravation in other domains of the disease (cognition, behavior, and functional capacity). However, the magnitude of pridopidine effect on motor symptoms could not be shown to be of clinical significance to the patient as measured by the functional and global measures assessed. Overall, pridopidine was generally safe and tolerable at the explored doses of up to 45 mg bid in HD patients.

It should be noted that, in the MAD study (ACR 16C018), in addition to the QT prolongation that may be of clinical concern, the dose of 90 mg bid, was associated with more frequent AEs, in particular dizziness and psychiatric events. Psychiatric events include nightmare, aggression, depressive mood, anxiety, and abnormal dreams). A dose of 112.5 mg was not administered in the MAD study.

Tolerability and Adverse Events

In the MAD study (ACR16C018), tolerability and safety of pridopidine 45 to 90 mg bid for 9 days was investigated in 36 healthy subjects. The safety profile of pridopidine in the 45 and 67.5 mg bid dose groups was similar to that observed in the larger clinical studies. Overall, the most frequently reported AEs were within the SOCs Nervous system disorders, Gastrointestinal disorders and Psychiatric disorders. The majority of AEs were considered mild. The 90 mg bid dose was considered the MTD in the MAD study.

EXAMPLES

Example 1

A Phase II, Randomized, Parallel-Group, Double-Blind, Placebo-Controlled Study, Evaluating the Safety and Efficacy of Pridopidine 45 mg, 67.5 mg, 90 mg, and 112.5 mg Twice-Daily Versus Placebo for Symptomatic Treatment in Patients with Huntington's Disease Purpose and Objectives of the Study The present study assesses the effects and dose-response of 4 dose levels of pridopidine (45, 67.5, 90, and 112.5 mg bid), compared with placebo, on improvement in motor function in patients with HD after 12 weeks of treatment. The study assesses the efficacy and dose-response of pridopidine 45 to 112.5 mg bid on motor impairment in patients with HD after 12 weeks of treatment using the UHDRS-TMS.

The study also assesses the effect and dose-response of 12 weeks treatment with pridopidine on various functional scales including:
The Clinician's Interview-based Impression of Change plus Caregiver Input (CIBIC-Plus)
The Physical Disability Scale (PDS)
UHDRS Functional assessment (FA)
Other secondary objectives are as follows:
To evaluate the safety and tolerability of a range of pridopidine doses in patients with HD during 12 weeks of treatment
To explore the PK of pridopidine in the study population
To investigate the relationship between exposure to pridopidine and outcome measures (e.g., clinical efficacy and toxicity parameters)

Study Design

General Design and Study Schema

This is a multicenter, multinational, randomized, parallel-group, double-blind, placebo-controlled study to compare the efficacy and safety of pridopidine 45, 67.5, 90, and 112.5 mg bid versus placebo in the treatment of motor impairment in HD.

Patients are equally randomized (1:1:1:1:1) to receive pridopidine 45, 67.5, 90, or 112.5 mg or placebo bid for 12 weeks, including a 4-week progressive titration period.

Patients are screened for a period of up to 2 weeks in order to determine whether they are eligible to participate into the study. The screening period includes a comprehensive medical and psychiatric history, rating of the Columbia-Suicide Severity Rating Scale (C-SSRS), a record of previous medications, a full physical and neurological examination, measurements of vital signs, typical clinical laboratory tests (hematology, biochemistry, urinalysis), serum pregnancy tests (if female of childbearing potential), and a single 12-lead ECG. The diagnostic of HD is established based on clinical features and the presence of ≥36 CAG repeats in the huntingtin gene. UHDRS-TMS and UHDRS-IS are assessed. In addition, in order to pre-expose participants to tests prior to measuring baseline performance (and by this way reduce the practice effects), the Quantitative motor (Q-Motor) and cognitive assessment battery (CAB brief) tests (symbol digit modalities test [SDMT], Stroop word reading test, abbreviated Montreal cognitive assessment [MoCA] scale and Trail Making Test B) are administered at screening. Eligible patients are randomized to receive active drug or placebo and are titrated during the first 4 weeks from pridopidine 22.5 mg bid to the final dose of 45, 67.5, 90, or 112.5 mg bid according to the treatment arm they are randomized to as detailed below During titration (Days 0 to 27), there are 2 on-site visits: at Day 0 (baseline) and at Day 14. There are additional phone calls on Days 6 and 20.

At the baseline visit, before the first dose of study drug, the Clinician's Interview Based Impression of Severity (CIBIS) is rated by an independent rater, while the study investigator assesses the Clinical Global Impression of Severity (CGI-S), the timed up and go (TUG) test, the PDS, the physical performance test (PPT), the UHDRS-TMS, the UHDRS-FA, the UHDRS-IS, the UHDRS Total functional capacity (TFC), the CAB brief, and the Problem Behaviors Assessment-Short form (PBA-s). The patient fills the Multiple Sclerosis Walking Scale (MSWS-12) and the HD-Quality of life scale (HD-QoL), and Q-Motor assessments are performed. CIBIS, UHDRS-TMS, UHDRS-TFC, and PDS should be evaluated prior to the other scales. Triplicate 12-lead ECG recordings and PK sampling for determination of the levels of pridopidine and its main metabolite (TV-45065, previously called ACR30) are performed before first dose and 1 to 2 hours after dose administration. PK samples are collected after ECG measurements.

Phone calls on Days 6 and 20 are performed to inquire about AEs and concomitant medications, and to allow the weekly dose increase on the following day. During the on-site visit at Day 14, before the administration of the study drug, a 12-lead ECG is performed in triplicate and blood samples are taken for PK sampling and electrolyte monitoring; if hypokalemia is observed, dosing is interrupted until normal electrolyte values are confirmed and maintained for 7 days. Vital signs are assessed in addition to the inquiry about AEs and concomitant medications. Additional 12-lead ECGs are performed in triplicate 1 to 2 hours after dose administration, followed by collection of the PK sample.

During the full treatment dose period (Days 28 to 84), there is a total of 4 on-site visits at Days 28, 42, 56, and 84 (or at early termination) and a phone call on Day 35. During the phone call at Day 35, inquiries about AEs and concomitant medication are conducted. At each of the on-site visits, safety variables are assessed, including triplicate ECG evaluation at predose and 1 to 2 hours after dose administration at the site (ECG is optional on Day 56), and clinical laboratory evaluations. In addition, PK sampling for determination of the levels of pridopidine and TV-45065 are done on Days 28, 42 and 84 before first dose, 1 to 2 hours after dose administration at the site, and on Days 42 and 84 also before leaving the site. When concomitant to ECG, PK samples are collected after the ECG recording.

Additional 12-lead ECG evaluations are performed on site, at the investigator's discretion, 1 to 2 hours after the afternoon dose for patients who, after their morning dose, show an increase from baseline in their QTcF value >50 msec. This optional afternoon ECG measurement is included for safety reasons, as the concentration of study drug may be higher in the afternoon than in the morning At Day 28, 56, and 84, in addition to safety assessments, the CIBIC-Plus is rated by an independent rater, while the study investigator assesses the UHDRS-TMS, the PDS, the Clinical Global Impression of Change (CGI-C), the TUG, the PPT, the UHDRS-FA, the UHDRS-TFC, the UHDRS-IS, the CAB brief, and the PBA-s. The patient fills the MSWS-12 and the HD-QoL, scales and Q-Motor assessments are performed.

Patients who complete all scheduled visits have final procedures and assessments performed at the final visit (Day 84) Patients who withdraw from the study before completing the evaluation period has the Day 84 procedures and assessments performed at their final visit.

There is a follow-up visit 2 weeks after last dose of study drug for safety evaluation, including a triplicate ECG evaluation (optional) and PK sample. At this visit, UHDRS-TMS and Q-Motor are also assessed.

The study schema is presented in FIG. 1.

Primary and Secondary Variables and Endpoints

The primary efficacy variable and endpoint for this study is change from baseline in the UHDRS-TMS (defined as the sum of all UHDRS motor domains ratings) at Week 12.

Secondary Functional Efficacy Variables and Endpoints

The secondary functional efficacy variables and endpoints for this study are as follows:
 CIBIC-Plus global score at Week 12 as compared to baseline (rated by an independent investigator)
 Change from baseline in the PDS score at Week 12
 Change from baseline in UHDRS-FA at Week 12

Other Functional Efficacy Variables and Endpoints

Other functional efficacy variables and endpoints for this study are as follows:
 CGI-C at Week 12 as compared to baseline (rated by the study investigator and the patient)
 Change from baseline in UHDRS-TFC at Week 12
 Change from baseline in UHDRS-IS at Week 12

Exploratory/Other Efficacy Variables and Endpoints

The exploratory/other efficacy variables and endpoints for this study are as follows:

Global/Functional Scales:
 Change from baseline in HD-QOL at Week 12
 Change from baseline in MSWS-12 at Week 12
 Change from baseline in the PPT at Week 12

TMS Subscores:
 Change from baseline in hand movement score (defined as the sum of UHDRS domains finger taps, pronate-supinate hands and luria [fist-hand-palm test]) at Week 12
 Change from baseline in Gait and balance score (defined as the sum of UHDRS domains gait, tandem walking and retropulsion pull test) at Week 12
 Change from baseline in UHDRS-mMS (defined as the sum of UHDRS domains dysarthria, tongue protrusion, finger taps, pronate-supinate hands, luria, rigidity, bradykinesia, gait, tandem walking, retropulsion pull test) at Week 12
 Percent of responders defined as patients with TMS change from baseline <0 at Week 12

Other Motor Assessments:
 Change from baseline in Q-Motor measurements at Week 12 including digitomotography (speeded index finger tapping), dysdiadochomotography (pronation/supination hand tapping), manumotography and choreomotography (grip force and chorea analysis) and pedomotography (speeded foot tapping)
 Change from baseline in the TUG test at Week 12

Cognitive/Psychiatric Assessments:
 Change from baseline in CAB brief at Week 12: SDMT, Stroop word reading test, abbreviated MoCA scale and Trail Making Test B
 Change from baseline in PBA-s at Week 12

Study Drugs and Dosage

Study drug (pridopidine and matching placebo) is administered as described below and as summarized in Table 1.

Investigational Product and Dosage

Pridopidine (as pridopidine hydrochloride) is provided as a white hard gelatin capsule, size 2 containing 45 mg pridopidine and a white hard gelatin capsule, size 4 containing 22.5 mg pridopidine.

Weeks 1 to 4: Titration Period

Patients randomized to the pridopidine 45 mg bid treatment arm
 Patients receive 1 capsule of 22.5 mg pridopidine, 1 capsule of 22.5 mg placeboand 1 capsule of 45 mg placebo bid (22.5 mg bid, total daily dose of 45 mg pridopidine)

Patients randomized to the pridopidine 67.5 mg bid treatment arm
 Weeks 1 and 2: Patients receive 1 capsule of 22.5 mg pridopidine, 1 capsule of 22.5 mg placebo and 1 capsule of 45 mg placebo bid (22.5 mg bid, total daily dose of 45 mg pridopidine)
 Weeks 3 and 4: Patients receive 1 capsule of 45 mg pridopidine and 2 capsules of 22.5 mg placebo bid (45 mg bid, total daily dose of 90 mg pridopidine)

TABLE 1

Dose Administration
(Capsules are Administrated Twice Daily to Give the Total Daily Dose)

| Treatment | Titration Period | | | | Full Dose Period |
|---|---|---|---|---|---|
| | Week 1 | Week 2 | Week 3 | Week 4 | Week 5-12 |
| Pridopidine 45 mg bid | 1 × 22.5 mg Pridopidine<br>1 × 22.5 mg Placebo<br>1 × 45 mg Placebo<br>(TDD = 45 mg) | 1 × 22.5 mg Pridopidine<br>1 × 22.5 mg Placebo<br>1 × 45 mg Placebo<br>(TDD = 45 mg) | 1 × 22.5 mg Pridopidine<br>1 × 22.5 mg Placebo<br>1 × 45 mg Placebo<br>(TDD = 45 mg) | 1 × 22.5 mg Pridopidine<br>1 × 22.5 mg Placebo<br>1 × 45 mg Placebo<br>(TDD = 45 mg) | 1 × 45 mg Pridopidine<br>1 × 22.5 mg Placebo<br>1 × 45 mg Placebo<br>(TDD = 90 mg) |
| Pridopidine 67.5 mg bid | 1 × 22.5 mg Pridopidine<br>1 × 22.5 mg Placebo<br>1 × 45 mg Placebo<br>(TDD = 45 mg) | 1 × 22.5 mg Pridopidine<br>1 × 22.5 mg Placebo<br>1 × 45 mg Placebo<br>(TDD = 45 mg) | 1 × 45 mg Pridopidine<br>2 × 22.5 mg Placebo<br>(TDD = 90 mg) | 1 × 45 mg Pridopidine<br>2 × 22.5 mg Placebo<br>(TDD = 90 mg) | 1 × 22.5 mg Pridopidine<br>1 × 45 mg Pridopidine<br>1 × 45 mg Placebo<br>(TDD = 135 mg) |
| Pridopidine 90 mg bid | 1 × 22.5 mg Pridopidine<br>1 × 22.5 mg Placebo<br>1 × 45 mg Placebo<br>(TDD = 45 mg) | 1 × 45 mg Pridopidine<br>2 × 22.5 mg Placebo<br>(TDD = 90 mg) | 1 × 45 mg Pridopidine<br>1 × 22.5 mg Pridopidine<br>1 × 22.5 mg Placebo<br>(TDD = 135 mg) | 1 × 45 mg Pridopidine<br>1 × 22.5 mg Pridopidine<br>1 × 22.5 mg Placebo<br>(TDD = 135 mg) | 2 × 45 mg Pridopidine<br>1 × 22.5 mg Placebo<br>(TDD = 180 mg) |
| Pridopidine 112.5 mg bid | 1 × 22.5 mg Pridopidine<br>1 × 22.5 mg Placebo<br>1 × 45 mg Placebo<br>(TDD = 45 mg) | 1 × 45 mg Pridopidine<br>2 × 22.5 mg Placebo<br>(TDD = 90 mg) | 1 × 45 mg Pridopidine<br>1 × 22.5 mg Pridopidine<br>1 × 22.5 mg Placebo<br>(TDD = 135 mg) | 2 × 45 mg Pridopidine<br>1 × 22.5 mg Pridopidine<br>(TDD = 180 mg) | 1 × 22.5 mg Pridopidine<br>2 × 45 mg Pridopidine<br>(TDD = 225 mg) |
| Placebo | 2 × 22.5 mg Placebo<br>1 × 45 mg Placebo | 2 × 22.5 mg Placebo<br>1 × 45 mg Placebo | 2 × 22.5 mg Placebo<br>1 × 45 mg Placebo | 2 × 22.5 mg Placebo<br>1 × 45 mg Placebo | 2 × 22.5 mg Placebo<br>1 × 45 mg Placebo |

TDD=Total daily dose Patients randomized to the pridopidine 90 mg bid treatment arm
- Week 1. Patients receive 1 capsule of 22 5 mg pridopidine, 1 capsule of 22 5 mg placebo and 1 capsule of 45 mg placebo bid (22.5 mg bid, total daily dose of 45 mg pridopidine)
- Week 2: Patients receive 1 capsule of 45 mg pridopidine and 2 capsules of 22.5 mg placebo bid (45 mg bid, total daily dose of 90 mg pridopidine)
- Weeks 3 and 4: Patients receive 1 capsule of 45 mg pridopidine, 1 capsule of 22.5 mg pridopidine and 1 capsule of 22.5 mg placebo bid (67.5 mg bid, total daily dose of 135 mg pridopidine)

Patients randomized to the pridopidine 112.5 mg bid treatment arm
- Week 1: Patients receive 1 capsule of 22.5 mg pridopidine, 1 capsule of 22.5 mg placebo and 1 capsule of 45 mg placebo bid (22.5 mg bid, total daily dose of 45 mg pridopidine)
- Week 2: Patients receive 1 capsule of 45 mg pridopidine and 2 capsules of 22.5 mg placebo bid (45 mg bid, total daily dose of 90 mg pridopidine)
- Week 3: Patients receive 1 capsule of 45 mg pridopidine, 1 capsule of 22.5 mg pridopidine and 1 capsule of 22.5 mg placebo bid (67.5 mg bid, total daily dose of 135 mg pridopidine)
- Week 4: Patients receive 1 capsule of 45 mg pridopidine and 2 capsules of 22.5 mg pridopidine (90 mg bid, total daily dose of 180 mg pridopidine)

Weeks 5 to 12: Full Dose Period

Patients randomized to the pridopidine 45 mg bid treatment arm receive 1 capsule of 45 mg pridopidine, 1 capsule of 22.5 mg placebo and 1 capsule of 45 mg placebo bid (total daily dose of 90 mg).

Patients randomized to the pridopidine 67.5 mg bid treatment arm receive 1 capsule of 45 mg pridopidine, 1 capsule of 22.5 mg pridopidine and 1 capsule of 45 mg placebo bid (total daily dose of 135 mg).

Patients randomized to the pridopidine 90 mg bid treatment arm receive 2 capsules of 45 mg pridopidine and 1 capsule of 22.5 mg placebo bid (total daily dose of 180 mg).

Patients randomized to the pridopidine 112.5 mg bid treatment arm receive 2 capsules of 45 mg pridopidine and 1 capsule of 22.5 mg pridopidine bid (total daily dose of 225 mg).

Other Study Drugs and Dosage

Placebo is presented as white hard gelatin capsules matching the 22.5 mg or 45 mg pridopidine capsules but containing no active ingredient, only the excipients (silicified microcrystalline cellulose and magnesium stearate).

Patients randomized to placebo receive 3 capsules bid, i.e., 3 capsules in the morning and 3 capsules in the afternoon (7 to 10 hours after the morning dose), during the whole study period. There is not an afternoon dose at the final visit (Day 84/Early Termination).

Weeks 1 to 4: Titration Period
 Patients randomized to placebo arm receive 2 capsules of 22.5 mg placebo and 1 capsule of 45 mg placebo bid.
Weeks 5 to 12: Full Dose Period
 Patients randomized to placebo arm receive 2 capsules of 45 mg placebo and 1 capsule of 22.5 mg placebo bid.
 Study procedures and assessments with their timing are summarized in Table 2.

TABLE 2

Study Procedures and Assessments

| | Titration Period | | | | | | Full Dose Period | | | | |
|---|---|---|---|---|---|---|---|---|---|---|---|
| Visit | V0 | V1 | TC | V2 | TC | V3 | TC | V4 | V5 | V6 | V7 |
| Day | −14 to −1 | 0 | 6 | 14 ± 3 | 20 | 28 ± 4 | 35 ± 3 | 42 ± 5 | 56 ± 5 | 84 ± 7 | 98 ± 7 |
| Procedures and assessments | Screening | BE | W1 | W3 | W3 | W5 | W6 | W7 | W9 | W12/Early Termination | Follow-up | Unsched Visit |

| Procedures and assessments | Screening | BE | W1 | W3 | W5 | W6 | W7 | W9 | W12/Early Termination | Follow-up | Unsched Visit |
|---|---|---|---|---|---|---|---|---|---|---|---|
| On-site visit | X | X | | X | | X | | X | X | X | X | X |
| Telephone call | | | X | | X | | X | | | | | |
| Informed consent | X | | | | | | | | | | | |
| Demography | X | | | | | | | | | | | |
| Medical and psychiatric history | X | | | | | | | | | | | |
| Prior medication history | X | | | | | | | | | | | |
| Inclusion and exclusion criteria[a] | X | X | | | | | | | | | | |
| Randomization | | X | | | | | | | | | | |
| Clinical laboratory tests (hematology and biochemistry) | X | X | | X[b] | | X | | X | X | X | X | X |
| Urinalysis | X | X | | | | X | | X | X | X | X | X |
| Pregnancy test (women of childbearing potential)[c] | X | | | | | X | | X | X | X | X | X |
| Full physical and neurological examination, including weight (height at screening only) | X | | | X | | X | | X | X | X | X | X |
| ECG | X[d] | X[e] | | X[e] | | X[e] | | X[e] | X[f] | X[e] | X[g] | X |
| Vital signs measurement | X | X | | X | | X | | X | X | X | X | X |
| C-SSRS (baseline version) | X | | | | | | | | | | | |
| C-SSRS (since last visit version) | | X | | | | X | | X | X | X | | |
| Blood sample for genetic analyses[h] | X | | | | | | | | | | | |
| UHDRS-TMS | X | X[i] | | | | X[i] | | X[i] | X[i] | | X | |
| UHDRS-FA | | X | | | | X | | X | X | | | |
| UHDRS-TFC | | X[i] | | | | X[i] | | X[i] | X[i] | | | |
| UHDRS-IS | X | X | | | | X | | X | X | | | |
| PBA-s | | X | | | | X | | X | X | | | |
| CIBIS | | X[i] | | | | | | | | | | |
| CIBIC-PIus | | | | | | X | | X | X | | | |
| PDS | | X[i] | | | | X[i] | | X[i] | X[i] | | | |
| PPT | | X | | | | X | | X | X | | | |
| CGI-S | | X | | | | | | | | | | |
| CGI-C | | | | | | X | | X | X | | | |
| HD-QoL | | X | | | | X | | X | X | | | |
| MSWS-12 | | X | | | | X | | X | X | | | |
| Q-Motor assessments[j] | X | X | | | | X | | X | X | | X | |
| TUG test | | X | | | | X | | X | X | | | |
| Cognitive assessment battery[k] | X | X | | | | X | | X | X | | | |

TABLE 2-continued

Study Procedures and Assessments

| | V0 | V1 | TC | V2 | TC | V3 | TC | V4 | V5 | V6 | V7 |
|---|---|---|---|---|---|---|---|---|---|---|---|
| | | | | | Titration Period | | | Full Dose Period Visit | | | |
| Day | −14 to −1 | 0 | 6 | 14 ± 3 | 20 | 28 ± 4 | 35 ± 3 | 42 ± 5 | 56 ± 5 | 84 ± 7 | 98 ± 7 |

Procedures and assessments

| | Screening | BE | W1 | W3 | W3 | W5 | W6 | W7 | W9 | W12/Early Termination | Follow-up | Unsched Visit |
|---|---|---|---|---|---|---|---|---|---|---|---|---|
| Blood samples for drug concentration$^l$ | | X | | X | | X | | X | | X | X | X |
| Adverse event inquiry | X | X | X | X | X | X | X | X | | X | X | X |
| Concomitant medication inquiry | X | X | X | X | X | X | X | X | | X | X | X |
| Review of tolerability to study drug prior to dose escalation (if applicable) | | | W | W | W | | | | | | | |
| Dispense/collect study drug | | W | | W | | W | | | W | W | | |
| Review study compliance | | W | | W | | W | | W | W | W | | |
| Study drug administration$^m$ | | ⟶ | | | | | | | | | | |

Table 2 legend:
$^a$Inclusion/exclusion criteria should be met at screening and reviewed on Day 0 before the patient is randomized
$^b$Electrolytes only
$^c$Serum pregnancy test at screening; urine pregnancy test at subsequent time points
$^d$A single ECG is performed. If there is evidence of a prolonged QTcF interval at screening (defined as a QTcF interval of >450 msec for males or >470 msec for females) then the ECG is repeated twice, and the mean of the 3 screening measurements are used to determine whether or not the patient is suitable for inclusion in the study.
$^e$ECG performed in triplicate prior to dose and 1 to 2 hours after dosing. When concomitant to PK sampling, ECG is recorded before PK sample collection. Additional 12-lead ECG evaluations should be performed on site, at the investigators discretion, 1 to 2 hours after the afternoon dose for patients who, after their morning dose, show an increase from baseline in their QTcF value >50 msec.
$^f$ECG is optional on Day 56, to be performed at the investigator's discretion where there are clinical circumstances that justify an additional ECG, eg, patients with a previous episode of hypokalemia without QT prolongation
$^g$ECG is optional at the follow-up visit, but should be performed for all patients with a previously observed cardiac concern and/or QTc change from baseline
$^h$Including CAG analysis, cytochrome P450 2D6 status, genetic long QT syndrome (assessed only in patients experiencing QT prolongation following study drug administration leading to study discontinuation), or any other genetic analyses related to pridopidine response or Huntington's disease
$^i$Evaluated in priority
$^j$Including digitomotography (speeded index finger tapping), dysdiadochomotography (pronation/supination hand tapping), manumotography and choreomotography (grip force and chorea analysis) and pedomotography (speeded foot tapping)
$^k$Includes symbol digit modalities test, Stroop word reading test, abbreviated Montreal cognitive assessment scale, and Trail Making Test B
$^l$On the baseline visit and on Days 14 and 28, samples for determination of levels of pridopidine and TV-45065 metabolite are collected prior to first dose and 1 to 2 hours after dose administration at the site. On Days 42 and 84, samples are collected prior to first dose, 1 to 2 hours after dose administration at the site, and before leaving the site. When concomitant to ECG, PK samples are collected after the ECG recording. At the follow up visit, 1 PK sample are collected. In case of SAE, an additional PK sampling should be aimed to be collected at the closest time to SAE. Every patient receive 3 capsules twice daily (bid), ie, 3 capsules in the morning and 3 capsules in the afternoon (7 to 10 hours after the morning dose), during the whole study period. Study drug is not administered at Early Termination visit. At on-site visits, the morning dose is taken at the site.

Procedures for Screening and Enrollment (Visit 0)

The screening visit (Visit 0) takes place not more than 2 weeks before the baseline visit. The following procedures are performed at the screening visit:

- obtain written informed consent before any other study-related procedures are performed
- review inclusion/exclusion criteria
- review medical and psychiatric history
- review medication history
- collect demographic information
- clinical laboratory tests (hematology, biochemistry, urinalysis)
- serum pregnancy test for women of child-bearing potential only
- vital signs measurements
- 12-lead ECG (single); if there is evidence of a prolonged QTcF interval at screening (defined as a QTcF interval of >450 msec) then the ECG is repeated twice, and the mean of the 3 screening measurements is used to determine whether or not the patient is suitable for inclusion in the study.
- full physical and neurological examination (including height and weight)
- C-SSRS (baseline version)
- UHDRS-TMS and UHDRS-IS
- Q-Motor assessments
- CAB brief tests (SDMT, Stroop word reading test, abbreviated MoCA scale and Trail Making Test B)
- collect blood sample for potential genetic analyses
- inform patients of study restrictions and compliance requirements Procedures for Baseline Visit (Visit 1)

Patients who meet the inclusion/exclusion criteria at screening (Visit 0) continue to Visit 1, when baseline evaluations are conducted. The following procedures are performed at Baseline before dose on site:

- review inclusion/exclusion criteria
- vital signs measurements
- inquire about AEs
- inquire about concomitant medication
- clinical laboratory tests (hematology, biochemistry including electrolytes, urinalysis);

results for electrolytes must be available before dosing
12-lead ECG in triplicate
C-SSRS (since last visit version)
UHDRS-TMS, UHDRS-FA, UHDRS-TFC, UHDRS-IS
CGI-S
CIBIS, completed by an independent rater
PDS
TUG test
PPT
HD-QOL
MSWS-12
Q-Motor assessments
CAB brief tests (SDMT, Stroop word reading test, abbreviated MoCA scale and Trail Making Test B)
PBA-s
obtain a 4-mL blood sample for plasma drug assay
dispense study drug (first dose taken at the site conditional to potassium level being within normal ranges)
review study compliance The following procedures are performed at Baseline after the first dose is administered on site:
1) 12-lead ECG in triplicate (1 to 2 hours after dose administration);
2) obtain a 4-mL blood sample for plasma drug assay (1 to 2 hours after dose administration); samples are collected as close as possible to, but after the ECG recording.

Procedures During Study Drug Treatment
Titration Period (Weeks 0) to 4)
Telephone Contact at Weeks 1 and 3 (Days 6 and 20)
Patients are contacted by telephone on Days 6 and 20 to evaluate tolerability to the study drug through assessment of AEs and concomitant medication usage, and to allow the weekly dose increase during the titration period (see above) that takes place on the following day (if applicable)

Week 3-Day 14 (Visit 2)
The following procedures/assessments are performed at Week 3 on the Day 14 (±3 days) visit (Visit 2):
Before Dosing:
  AE inquiry
  concomitant medication review
  clinical laboratory tests (electrolytes only); results for electrolytes must be available before dosing
  full physical and neurological examination (including weight)
  triplicate 12-lead ECG
  vital signs measurements
  obtain a 4-mL blood sample for plasma drug assay (as close as possible to, but after the ECG recording)
  collect/dispense study drug
  study compliance review
  morning dose of study drug administration (conditional to potassium level being within normal range)
After Dosing:
  triplicate 12-lead ECG (1 to 2 hours after dose administration)
  obtain a 4-mL blood sample for plasma drug assay 1 to 2 hours after dose administration; PK samples are collected as close as possible to, but after the ECG recording.

Full Dose Period (Weeks 5 to 12)
Weeks 5, 7, and 9-Days 28, 42, and 56 (Visits 3, 4, and 5)
The following procedures/assessments are performed on Days 28 (±4 days), 42 (±5 days), and 56 (±5 days) at Weeks 5, 7, and 9 (Visits 3, 4, and 5):

Before Dosing:
  AE inquiry
  concomitant medication review
  clinical laboratory tests (hematology, biochemistry including electrolytes, urinalysis)
  urine pregnancy test for women of child-bearing potential only (Days 28 and 56 only)
  full physical and neurological examination (including weight)
  triplicate 12-lead ECG (Note: ECG is optional on Day 56, to be performed at the investigator's discretion where there are clinical circumstances that justify an additional ECG, eg, patients with a previous episode of hypokalemia without QT prolongation)
  vital signs measurements
  C-SSRS (since last visit version)
  Days 28 and 42 only: obtain a 4-mL blood sample for plasma drug assay (as close as possible to, but after the ECG recording)
  collect/dispense study drug (Days 28 and 56 only)
  study compliance review
  morning study drug dose administration (conditional to potassium level being within normal range)
After Dosing:
  triplicate 12-lead ECG (1 to 2 hours after dose administration) (Note: ECG is optional on Day 56, to be performed at the investigator's discretion where there are clinical circumstances that justify an additional ECG, eg, patients with a previous episode of hypokalemia without QT prolongation)
  Days 28 and 42 only: obtain a 4-mL blood sample for plasma drug assay 1 to 2 hours after dose administration; PK samples are collected as close as possible to, but after the ECG recording.
  Day 42 only: obtain a 4-mL blood sample for plasma drug assay before leaving the site In addition, the following efficacy procedures/assessments are performed on Days 28 and 56 only (Visits 3 and 5) with UHDRS-TMS, CIBIC-Plus, UHDRS-TFC, and PDS evaluated in priority: CIBIC-Plus, PDS, PPT, UHDRS-TMS, UHDRS-FA, UHDRS-TFC, UHDRS-IS, CGI-C, TUG test, HD-QoL, MSWS-12, Q-Motor assessments, CAB brief tests (SDMT, Stroop word reading test, abbreviated MoCA scale and Trail Making Test B), and PBA-s.

Telephone Contact at Week 6 (Day 35):
Patients are contacted by telephone on Day 35 (±3 days) to evaluate tolerability to the study drug through assessment of AEs and concomitant medication usage.

Week 12-Day 84 (Visit 6) or Early Termination
The following procedures/assessments are performed on Day 84 (±7 days) at Week 12 (Visits 6) or at the Early Termination visit:
Before Dosing:
  AE inquiry
  concomitant medication review
  clinical laboratory tests (hematology, biochemistry including electrolytes, urinalysis)
  urine pregnancy test for women of child-bearing potential only
  full physical and neurological examination (including weight)
  triplicate 12-lead ECG
  vital signs measurements
  C-SSRS (since last visit version)
  obtain a 4-mL blood sample for plasma drug assay (as close as possible to, but after the ECG recording)
  study compliance review morning study drug dose administration (conditional to potassium level being within normal range) (Note: study drug is not administered if Early Termination visit)

After Dosing:

triplicate 12-lead ECG (1 to 2 hours after dose administration)

obtain a 4-mL blood sample for plasma drug assay (1 to 2 hours after dose administration at the site, and before leaving the site [as close as possible to, but after the ECG recording])

collect study drug

The following efficacy procedures/assessments are performed on Day 84 (Visit 6) with UHDRS-TMS, CIBIC-Plus, UHDRS-TFC, and PDS evaluated in priority: CIBIC-Plus, PDS, PPT, UHDRS-TMS, UHDRS-FA, UHDRS-TFC, UHDRS-IS, CGI-C, TUG test, HD-QOL, MSWS-12, Q-Motor assessments, CAB brief tests (SDMT, Stroop word reading test, abbreviated MoCA scale and Trail Making Test B), and PBAs. There is no afternoon dose on Day 84/Early Termination Follow-up Visit There is a follow-up visit 2 weeks after the last dose of study drug (Day 98, ±7 days). The following procedures/assessments are performed: AE inquiry, concomitant medication review, clinical laboratory tests (hematology, biochemistry, urinalysis), urine pregnancy test for women of child-bearing potential only, full physical and neurological examination (including weight), optional triplicate 12-lead ECG, should be performed for all patients with a previously observed cardiac concern and/or QTc change from baseline, vital signs measurements, UHDRS-TMS, Q-Motor assessments, and obtain a 4-mL blood sample for plasma drug assay after ECG collect Procedures After Study Drug Treatment Discontinuation Patients who participate in the study in compliance with the protocol for at least 12 weeks of double-blind treatment are considered to have completed the study.

For patients who complete the study or withdraw prematurely, final evaluations are performed at the Week 12/Early Termination visit (Visit 6). For patients who do not have a final visit within 7 days after their last dose of study drug, efficacy evaluations are not performed.

Unscheduled Visits

An unscheduled visit are performed at any time during the study at the patient's request or as deemed necessary by the investigator. The date and reason for the unscheduled visit are recorded on the CRF as well as any other data obtained (eg, AEs, concomitant medications and treatments, and results from procedures or tests). In case of an SAE, an additional PK sample is collected at the closest time to SAE.

Population Studied

The study population consists of male or female patients aged ≥21 years and with body weight ≥50 kg, with HD diagnoses obtained with the identification of HD clinical features and confirmed by the presence of ≥36 CAG repeats in the huntingtin gene. HD should have been diagnosed when the patient was aged ≥18 years. In addition, patients have: 1) a sum of ≥25 points on UHDRS-TMS at the screening visit, and 2) a UHDRS Independence Score (IS) <90% at the screening visit. Patients are ambulatory and have the capacity to travel to the clinic visits.

Patient Inclusion Criteria:

Patients are included in the study only if they meet all of the following criteria:

a. Diagnosis of HD based on clinical features and the presence of ≥36 CAG repeats in the huntingtin gene b. Male or female age ≥21 years, with an onset of HD after 18 years' old.

c. Females of child bearing potential have to be compliant in using adequate birth control throughout the duration of the study, including the follow-up period. Adequate birth control is defined as consistent practice of an effective and accepted method of contraception (hormone-based, intrauterine device, or double barrier contraception, ie, condom and diaphragm, diaphragm and spermicidal gel or foam). Abstinence is an acceptable method of contraception. Males have to be compliant in using adequate birth control with their partners (as defined above) throughout the duration of the study.

d. Body weight ≥50 kg e. A sum of ≥25 points on the UHDRS-TMS at the screening visit f. UHDRS-IS score below 90% at the screening visit.

g. Able and willing to provide written informed consent prior to any study related procedure being performed at the screening visit.

h. Willing to provide a blood sample for genetic analyses (including CAG analysis, CYP2D6 status, genetic long QT syndrome in patients who had QT prolongation following study drug administration or any other genetic analyses related to pridopidine response or HD) at the screening visit.

i. Willing and able to take oral medication and able to comply with the study specific procedures.

j Ambulatory, being able to travel to the study centre, and judged by the investigator as likely to be able to continue to travel for the duration of the study k. Availability and willingness of a caregiver, informant or family member to accompany the patient to the clinic at study visits assessing CIBIC-Plus and HD-QOL l. For patients taking allowed antipsychotic, antidepressant or other psychotropic medication, the dosing of medication must have been kept constant for at least 6 weeks before screening and must be kept constant during the study.

Patient Exclusion Criteria

Patients are excluded from participating in this study if they meet any of the following criteria:

a. A prolonged QTcF interval (defined as a QTcF interval of >450 msec for males or >470 msec for females) at the screening or baseline visit. If there is evidence of a prolonged QTcF interval at screening from the initial (single) measurement, then the ECG is repeated twice, and the mean of the 3 screening measurements is used to determine whether or not the patient is suitable for inclusion in the study.

b. Patients with clinically significant heart disease at the screening visit.

c. Patients with a history of Long QT Syndrome or a first degree relative with this condition d. Patients with a history of epilepsy or of seizures within the last 5 years e. Have other serious medical illnesses (including but not limited to uncontrolled hypertension, respiratory disease including severe form of asthma, hepatic disease, renal disease, AIDS, unstable psychiatric or other neurologic disorder) which in the opinion of the investigator may put the patient at risk when participating in the study or may influence the results of the study or affect the patient's ability to take part in the study f. Patients with serum potassium, magnesium and/or calcium levels outside of the central laboratory's reference range at the screening visit g. Patients receiving medications (within the last 6 weeks prior to screening) that have been proven to prolong QT interval or who may require such medications during the course of the study such as but not limited to non allowed anti psychotic medications, tricyclic antidepressants and/or Class I antiarrhythmics
h. Patients receiving medications (within the last 6 weeks prior to screening) that are metabolized by CYP2D6 and have the potential of reducing seizure threshold
i. Creatinine clearance <60 mL/min at screening, calculated using the Cockcroft-Gault equation
j. Any clinically significant, abnormal, screening laboratory result which in the opinion of the investigator, affects the patients' suitability for the study or puts the patient at risk if he/she enters the study
k. Ongoing alcohol and/or drug abuse (within the 6 months prior to screening) as defined by Diagnostic and Statistical Manual-Fourth Edition Text Revision (DSM-IV TR) criteria for substance abuse
l. Patients with active suicidal ideation as measured by a most severe suicide ideation score of 4 (Active Suicidal Ideation with Some Intent to Act, without Specific Plan) or 5 (Active Suicidal Ideation with Specific Plan and Intent) on the C-SSRS
m. Patients with known intracranial risk or history of stroke or hemorrhage
n. Females who are pregnant or lactating
o. Known allergy to any ingredients of the study medication or placebo (pridopidine, silicified microcrystalline cellulose, magnesium stearate)
p. Previous exposure with pridopidine
q. Treatment with tetrabenazine within 6 weeks of study screening
r. Treatment with any investigational product within 6 weeks of screening or patients planning to participate in another clinical study assessing any investigational product during the study.

Withdrawal Criteria and Procedures

Each patient is free to withdraw from the study drug at any time. Each investigator also has the right to withdraw a patient from the study drug in the event of intercurrent illness, AEs, pregnancy, or other reasons concerning the health or well-being of the patient, or in the event of lack of cooperation . . .

If a patient decides to withdraw after administration of study drug(s), or if the investigator decides to withdraw the patient, all efforts are made to complete and report all observations up to the time of withdrawal. A complete final evaluation at the time of the patient's withdrawal is made and an explanation given as to why the patient is withdrawing or being withdrawn from the study.

A patient who is enrolled but does not complete the study is not replaced.

Treatment of Patients
Study Drugs Administered

Following the baseline visit, patients are randomly assigned to 1 of 4 pridopidine treatment arms or to the placebo treatment arm. Six capsules are administered orally (with water) each day; 3 capsules in the morning and 3 capsules in the afternoon (7 to 10 hours after the morning dose). Capsules are taken with or without food. Following titration, patients remain at their randomized dosage for the duration of the study.

Each medication pack contains 3 distinct labeled bottles containing the study drug and are provided for patients to take at home, or at the study center when dosing coincides with a study visit.

Prior and Concomitant Therapy or Medication

Medications that are not prohibited during the study are allowed at the discretion of the investigator. To the extent possible, patients continue on medications already prescribed at enrollment; dose modifications and introduction of new medications is avoided unless deemed necessary for optimal patient care by the investigator.

Disallowed CYP2D6 substrates are administered only 1 week after the discontinuation of pridopidine (ie, 1-week washout), to allow enzyme recovery.

If a patient receives a prohibited treatment during the randomized phase of the study, he/she is encouraged to continue in the study and complete the study visits in accordance with the study visit schedule; however, the patient may need to be withdrawn from study treatment. If the patient refuses to be seen for further visits, the assessments for Week 12 (Day 84)/Early Termination are performed, as far as possible (at least attempts to capture information on AEs and concomitant medication).

At each clinic visit after the screening visit, the investigator asks patients whether they have taken any medications (other than study drug), including over-the-counter medications, vitamins, or herbal or nutritional supplements, since the previous visit.

Permitted Medication

For patients taking allowed antipsychotic, antidepressant, antiarrhythmic, or other medication, the dosing of medication must have been kept constant for at least 6 weeks before screening and must be kept constant during the study.

Allowed antipsychotic medications are olanzapine, quetiapine, thiothixene, acetophenazine, triflupromazine, loxapine, tiapride, chlorprothixene, and bromperidol. Aripiprazole, risperidone, and perphenazine are permitted, subject to dose reductions.

Allowed antidepressant medications are venlafaxine, paroxetine, duloxetine, sertraline, omipramol (opipramol), butriptyline, mianserin, moclobemide, tranylcypromine, buspiron, bupropion, reboxetine, and dibenzepin. Fluvoxamine, trimipramine, and mirtazapine are permitted, subject to dose reduction.

Mexalatine and tocainide are allowed antiarrhythmic medications, subject to dose reduction.

Allowed medications lowering seizure thresholds are baclofen, bupropion, ciprofloxacin, cyclosporine, isoniazid, lindane, methylphenidate, metronidazole, penicillins, theophylline, amantadine, morphine, buprenorphine, diphenoxylate, alfentanil, fentanyl, remifentanil, meptazinol, and pethidine.

Prohibited Medication
Antipsychotic Medication

Ziprasidone, clozapine, haloperidol, mesoridazine, thioridazine, pimozide, zuclopenthixol, chlorpromazine, paliperidone, iloperidone, fluphenazine, prochlorperazine, trifluoperazine/trifluroperazine, flupentixol, benperidol, amisulpride, and sulpiride are not allowed within 6 weeks of screening (Visit 0) and during the study.

Antidepressant Medication:

Lithium, the tricyclic/tetracyclic antidepressants trazodone, amitriptyline, nortriptyline, imipramine, desipramine, maprotiline, doxepin, clomipramine, protriptyline, and amoxapine, and the serotonin-norepinephrine reuptake inhibitors citalopram, escitalopram, and fluoxetine are not allowed within 6 weeks of screening (Visit 0) and during the study.

Antiarrhythmic Medication:

Disopyramide, procainamide, quinidine, flecainide, propafenone, amiodarone, dofetilide, ibutilide, and sotalol are not allowed within 6 weeks of screening (Visit 0) and during the study.

Medications Lowering Seizure Thresholds:

Maprotiline, dipipanone, dihydrocodeine, methadone, oxycodone, papaveretum, pentazocine, and tramadol are not allowed within 6 weeks of screening (Visit 0) and during the study.

Other Prohibited Medications:

Due to either QT prolongation effects or metabolism by CYP2D6 into active metabolites, the following medications are not allowed within 6 weeks of screening (Visit 0) and during the study: astemizole, terfenadine, azithromycin, erythromycin, moxifloxacin, pentamidine, sparfloxacin, clarithromycin, chloroquine, halofantrine, bepridil, cisapride, domperidone, droperidol, levomethadyl, methadone, codeine, tramadol, sevoflurane, and tamoxifene.

Total Blood Volume Tested

The total volume of blood estimated to be collected from each patient is detailed in Table 3.

TABLE 3

Total Blood Volume Collected from Each Patient

| Type of Assessment | Number of Samples Collected | Volume per Sample | Total Volume for Assessment |
|---|---|---|---|
| Pharmacokinetic | 13 | 4 mL | 52 mL |
| Serum Chemistry | 8 | 10.5 mL | 84 mL |
| Hematology | 7 | 3 mL | 21 mL |
| CAG Testing | 1 | 4 mL | 4 mL |
| CYP2D6 Genotyping | 1 | 6 mL | 6 mL |
| Total | | | 167 mL |

CAG = cytosine-adenosine-guanine;
CYP2D6 = cytochrome P450 2D6

Assessment of Efficacy

Except where stated, efficacy assessments detailed in the following sections are performed on Day 0 (Visit 0, baseline), Day 28 (Visit 3), Day 56 (Visit 5), and Day 84 (Visit 6). UHDRS-TMS and Q-Motor assessments are also performed at the follow-up visit.

Primary Efficacy Variable and Endpoint

The primary efficacy variable and endpoint is the change from baseline in the UHDRS-TMS (defined as the sum of all UHDRS motor domain ratings) at Week 12.

The UHDRS comprises a broad assessment of features associated with HD. (Huntington Study Group 1996) It is a research tool which has been developed to provide a uniform assessment of the clinical features and course of HD.

The TMS component of UHDRS comprises 31 assessments from the 15 items of the UHDRS, with each assessment rated on a 5-point scale from 0 (normal) to 4 (maximally abnormal).

Secondary Efficacy Variable and Endpoint
Clinician Interview Based Impression of Change Plus Caregiver Input Global change in HD at Week 12 is measured using the CIBIS scale at baseline (Day 0) and the CIBIC-Plus scale at subsequent time points. The CIBIC-Plus (version ADCS-CGIC) was developed, validated, and is commonly used in studies of anti-dementia drugs in Alzheimer's Disease. (Joffres 2000)

An independent rater whose only role in the study is to conduct these global assessments evaluates the patient's overall disease severity prior to the initiation of study drug. This assessment, known as the CIBIS, rates the patient on a 7-point Likert scale from extremely severe HD to no symptoms of HD. At each subsequent visit in which the evaluation is performed (Weeks 5, 9, and 12), the CIBIC-Plus is administered by the same independent rater, but without knowledge of other endpoint assessments or the AEs experienced by the patient during the study (so as not to confound the rating of CIBIC as an efficacy measure or to unblind the study). The independent rater is not permitted to discuss the medical condition of the patient with the treating physician. Instead, the independent rater exclusively considers observations of the patient's cognitive, functional, and behavioral performance obtained through interviewing the patient and the caregiver. The rater then compares those findings to the baseline assessment. The overall impression of change from baseline (CIBIC-Plus) is rated on a 7-point scale: 1=marked improvement: 2=moderate improvement; 3=minimal improvement; 4=no change; 5=minimal worsening; 6=moderate worsening; 7=marked worsening; all assessments were relative to baseline. A higher score indicates a worsening of global function. In HD, the inclusion of caregiver input is particularly critical for a global assessment as previous studies have demonstrated that patients have limited awareness and recognition of their deficits Physical Disability Scale The PDS is used during the study as a measure of disability. Patients are scored on a scale from 10 ("Fixed posture requiring total care-gastrotomy, catheterization") to 100 ("Normal; no disease evident"). (Myers 1991)

UHDRS Functional Assessments

The FA scale of the UHDRS assesses functionality in 25 tasks of daily living (eg, "Could patient engage in gainful employment in his/her accustomed work?"). Each question is answered with 'yes' or 'no'.

Other Functional Efficacy Variables and Endpoints

Other efficacy variables and endpoints are described below.

Clinical Global Impression of Severity and Change

CGI-S is assessed at baseline (Day 0) and CGI-C is used at all subsequent time points (Days 28, 56, and 84) to assess changes from baseline.

The CGI-S scale was initially designed to assess treatment response in patients with mental disorders (Guy 1976) but is now used widely in a range of illnesses. Illness severity is rated by the investigator on a 7-point scale (1=normal, not at all ill to 7=among the most extremely ill patients). The assessment is based on investigator judgment, supported by a comprehensive, semi-structured, patient/caregiver interview. The CGI-C scale measures the change in the patient's clinical status from a specific point in time, using a 7-point scale, ranging from 1 (very much improved) to 7 (very much worse), with a score of 4 indicating no change.

UHDRS Total Functional Capacity

The TFC scale of the UHDRS assesses 5 functional domains associated with disability (occupation, finances, domestic chores, activities of daily living, and care level).

UHDRS Independence Scale

The independence scale of the UHDRS is a rating scale where the patient's degree of independence is given in percentage, from 10% (tube fed, total bed care) to 100% (no special care needed). Scores must end in 0 or 5 (eg, 10%, 15%, 20% etc). Patients with a UHDRS-IS score >90% at the screening visit are not eligible for the study.

Exploratory/Other Efficacy Variables
Global/Functional Scales
Huntington's Disease Quality of Life The HD-QoL is a standardized instrument for measuring health-related quality of life. (Hocaoglu 2012) It is a validated disease-specific measure designed for HD, and can provide a summary score of overall health-related quality of life, as well as scores on several discrete scales. HD-QoL is for people who are living with HD; this includes people who are at risk for HD, people who have tested positive for the huntingtin gene but do not have symptoms, and also for people at early through to late stages of disease. HD-QoL can be used across the full spectrum of HD.

Multiple Sclerosis Walking Scale

MSWS-12 was originally developed to measure the impact of multiple sclerosis (MS) on walking. However, as other disabling neurological conditions affect a person's ability to walk, it was adapted to become a generic measure of walking and mobility. It contains 12 items describing the impact of MS on walking which were generated from 30 MS patient interviews, expert opinion, and literature review. (Hobart 2003)

Physical Performance Test

The PPT quantifies the patient's performance in physical tasks. (Reuben 1990, Hocaoglu 2012) It is a standardized 9-item test that measures the patient's performance on functional tasks. Patients are given 2 chances to complete each of the 9 items, and assistive devices are permitted for the tasks that require a standing position (items 6 to 9). Both the speed and accuracy at which the patients complete the items are taken into account during scoring. The maximum score of the test is 36, with higher scores indicating better performance.

Total Motor Score Subscores
UHDRS Hand Movement Score

The hand movement score is defined as the sum of UHDRS domains finger taps, pronate-supinate hands and luria (fist-hand-palm test).

UHDRS Gait and Balance Score

The gait and balance score is defined as the sum of UHDRS domains gait, tandem walking and retropulsion pull test.

UHDRS Modified Motor Scale

The UHDRS-mMS is defined as the sum of following domains from UHDRS-TMS: dysarthria, tongue protrusion, finger taps, pronate-supinate hands, luria, rigidity, bradykinesia, gait, tandem walking, and retropulsion pull test.

TMS Proportion of Responders

The percentage of responders, defined as patients with TMS change from baseline ≤0 at Week 12.

Other Motor Assessments
Quantitative Motor Assessments

Q-Motor assessments are performed only in those sites that have access to the devices needed to perform the assessments and, where this is the case, only in those patients who are capable of performing the assessments.

Motor deficits can be objectively assessed using different Q-Motor assessments. All Q-Motor assessments are based on the application of precalibrated and temperature controlled force transducers and 3-dimensional position sensors with very high sensitivity and test-retest reliability across sessions and sites in a multicenter clinical study. Q-Motor measures thus aim to reduce the limited sensitivity of categorical clinical rating scales, the intra- and inter-rater variability, and placebo effects observed in scales such as UHDRS-TMS. In addition, Q-Motor assessments allow for the objective monitoring of unintended motor side-effects in clinical studies.

Tasks detailed in the sections below have been selected for use in the current study. Data transfer is performed using a secure web based platform, allowing continuous centralized data monitoring and quality control. Data analysis is performed blinded and automated as described in the SAP.

Digitomotography (Speeded Index Finger Tapping)

The patient places their hand on a hand rest with their index finger positioned above a force-transducer Recordings start after practice runs. The patient is instructed to finger tap as fast as possible between 2 auditory cues. The beginning of a tap is defined as a rise of the force by 0.05 N above maximal baseline level. The tap ends when it drops to 0.05 N before the maximal baseline level is reached again. The duration and variability of tap durations (TD), inter onset intervals (IOI), inter peak intervals (IPI), and inter tap intervals (ITI) are the exploratory outcome measures for speeded tapping. In addition, variability of peak tapping forces (TF) is calculated as coefficient of variation, and the tapping frequency (Freq), ie, the number of taps between the onsets of the first and the last tap divided by the time in between, is determined. Five trials of 10 seconds duration are performed with each hand.

Dysdiadochomotography (Pronation/Supination Hand Tapping)

This task assesses the regularity of hand taps performed when alternating between the palm and dorsal surface of the hand performing a repetitive pronation/supination movement. The force and duration of the hand taps are recorded similarly to the speeded tapping task. A tone cues the start and end of an assessment. Five trials of 10 seconds duration are performed with each hand.

Manumotography and Choreomotography (Grip Force and Chorea Analysis) This task assesses the coordination of isometric grip forces in the precision grip between the thumb and index finger. Grip forces are assessed during grip initiation, object transport, and in a static holding phase. Patients are instructed to grasp and lift a device equipped with a force transducer and 3-dimensional position sensor in the precision grip between thumb and index finger and hold it stable adjacent to a marker 10-cm high. Grip forces and 3-dimensional position and orientation of the object are recorded. Mean isometric grip forces and grip force variability in the static phase (expressed as coefficient of variation=standard deviation [SD]/mean×100) (GFV-C) are calculated during a 15-second period starting 8 seconds after the first cueing tone. Five trials of 20 seconds duration are performed with each hand. Chorea is assessed calculating a "position-index" and "orientation-index". Start and end of assessment are signaled by a cueing tone.

Pedomotography (Speeded Foot Tapping)

The patient places a foot on the foot device such that the ball of the foot is positioned above a force-transducer. Recordings start after practice runs. The patient is instructed to tap with the foot as fast as possible between 2 auditory cues The beginning of a tap is defined as a rise of the force by 0.05 N above maximal baseline level. The tap ends when it dropped to 0.05 N before the maximal baseline level is reached again. The duration and variability of TD, IOI, IPI, and ITI are the exploratory outcome measures for speeded tapping. In addition, variability of peak TF is calculated as coefficient of variation, and the tapping Freq, ie, the number of taps between the onsets of the first and the last tap divided by the time in between, is determined. Five trials of 10 seconds duration are performed with each foot.

Timed Up and Go Test

The TUG is a simple test used to assess a person's mobility and requires both static and dynamic balance. It uses the time that a person takes to rise from a chair, walk 3 meters, turn around, walk back to the chair, and sit down. During the test, the person is expected to wear their regular footwear and use any mobility aids that they would normally require The TUG is used frequently in the elderly population, as it is easy to administer and can generally be completed by most older adults. The test is quick, requires no special equipment or training, and is easily included as part of the routine medical examination. (Podsiadlo 1991) The use of the TUG test in conjunction with UHDRS has been recommended for clinical studies of HD. (Rao 1991)

Cognitive Assessment Battery

The following sections describe the tests that are part of the CAB brief.

Symbol Digit Modalities Test

The SDMT is a paper/pencil test that requires patients to look at a key that pairs specific symbols to the digits 1 to 9, and then to look at a series of symbols and fill in the corresponding missing numbers.

Stroop Word Reading Test

The Stroop interference test measures the ability of the patient to concentrate and ward off distractions. (Stroop 1935) The test consists of 3 items; naming color rectangles (red, green, or blue), reading color words written in black, and naming the color of the ink of incongruent color words. Each test comprises 100 stimuli presented on a card. The test is scored as the number of correct responses made in 45 seconds.

Montreal Cognitive Assessment Scale (Partial) The MoCA is a freely available paper and pencil test, designed as a screening for mild cognitive impairment. (Bezdicek 2013) It includes assessments of visuospatial and executive function, memory, attention, language, abstraction, delayed recall (optional), and orientation. For this study, an abbreviated version of the MoCA is used, ie, the MoCA partial (including 3 sub-items-memory, language, and fluency—that are assessed)

Trail Making Tests A and B

In the Trail Making Test, part A, the patient sees a scattered display of circled numbers and has to "connect the dots" by tracing a line going through each number in increasing, sequential order. The Trail Making Test, part B is similar except the patient has to alternate between letters and numbers (A-1-B-2-C-3, etc). (Bowie 2006) Trail A is used only as part of the training.

Problem Behaviors Assessment-Short Form

Because of the prominence of psychiatric symptoms in HD, it is recommended that the PBA-s form be used in all HD studies with any need for behavioral assessment as a comprehensive screen for the most common psychiatric symptoms in HD. (Craufurd 2001, Kingma 2008) The PBA-s also includes questions concerning suicidal behavior, a particular concern in HD. The PBA-s is based on the same set of core behavioral symptoms as the UHDRS Behavioral questions, which were used previously as the global psychiatric measure in most HD studies. The PBA-s has more detailed questions and more specific guidance on administration and scoring The PBA-s is a brief semi-structured interview covering the most common behavioral and psychiatric manifestations of HD. The interview is not restricted to a single construct, but rather covers several broad symptom domains relevant to HD, comprising 11 items: low mood, suicidal ideation, anxiety, irritability, anger/aggressive behavior, loss of motivation, perseverative thinking or behavior, obsessive-compulsive behaviors, paranoid thinking, hallucinations, behavior suggestive of disorientation. Each symptom is rated for severity on a 5-point scale according to detailed scoring criteria which roughly correspond to the following: 0= "not at all"; 1=trivial; 2=mild, 3=moderate (disrupting everyday activities) and 4=severe or intolerable. Each symptom is also scored for frequency on a 5-point scale as follows: 0=symptom absent; 1=less than once weekly; 2=at least once a week, 3=most days (up to and including some part of every day); and 4=all day, every day. Severity and frequency scores are multiplied to produce an overall 'PBA score' for each symptom.

Assessment of Safety

Adverse Events

Definition of an Adverse Event

An adverse event (AE) is any untoward medical occurrence in a patient administered a pharmaceutical product, regardless of whether it has a causal relationship with this treatment.

In this study, any AE occurring after the clinical study patient has signed the informed consent form should be recorded and reported as an AE.

An AE can, therefore, be any unfavorable and unintended physical sign, symptom, or laboratory parameter that develops or worsens in severity during the course of the study, or significant worsening of the disease under study or of any concurrent disease, whether or not considered related to the study drug. A new condition or the worsening of a pre-existing condition is considered an AE.

Stable chronic conditions (such as arthritis) that are present before study entry and do not worsen during the study are not considered AEs.

Worsening of the disease under study is measured by UHDRS scales and the CAB and should be recorded as an AE only if the presentation and/or outcome is more severe than would normally be expected from the normal course of the disease in a particular patient.

Accordingly, an AE can include any of the following:
intercurrent illnesses
physical injuries
events possibly related to concomitant medication
significant worsening (change in nature, severity, or frequency) of the symptoms of the disease under study or other pre-existing conditions. (Note: A condition recorded as pre-existing that is intermittently symptomatic [e.g., headache] and which occurs during the study should be recorded as an AE.)
drug interactions
events occurring during diagnostic procedures or during any washout phase of the study
laboratory or diagnostic test abnormalities that result in the withdrawal of the patient from the study, are associated with clinical signs and symptoms or an SAE, or require medical treatment or further diagnostic work-up, or are considered by the investigator to be clinically significant. Note: Abnormal laboratory test results at the screening visit that preclude a patient from entering the study or receiving study treatment are not considered AEs, but is evaluated to monitor data from patients who do not meet screening criteria.
all events of possible drug-induced liver injury with hyperbilirubinemia (defined as aspartate aminotransferase [AST] or alanine aminotransferase [ALT]≥3 times the upper limit of the normal range [ULN], plus either bilirubin ≥2 times the ULN or International Normalized Ratio >1.5) or Hy's Law events require immediate study treatment cessation and reporting as an SAE. Hy's Law events are defined as follows:

The drug causes hepatocellular injury, generally shown by more frequent 3-fold or greater elevations above the ULN of ALT or AST than the (nonhepatotoxic) control agent or placebo.

Among patients showing such aminotransferase elevations, often with aminotransferases much greater than 3×ULN, some patients also show elevation of serum total bilirubin to >2×ULN, without initial findings of cholestasis (serum alkaline phosphatase activity >2×ULN).

No other reason can be found to explain the combination of increased aminotransferase and serum total bilirubin, such as viral hepatitis A, B, or C, preexisting or acute liver disease, or another drug capable of causing the observed injury.

Serious Adverse Events
Definition of a Serious Adverse Event

An SAE is an AE occurring at any dose that results in any of the following outcomes or actions:
1) death,
2) a life-threatening AE (ie, the patient was at immediate risk of death from the event as it occurred); does not include an event that, had it occurred in a more severe form, might have caused death
3) inpatient hospitalization or prolongation of existing hospitalization means that hospital inpatient admission and/or prolongation of hospital stay were required for treatment of an AE, or that they occurred as a consequence of the event. Hospitalizations scheduled for an elective procedure or for treatment of a pre-existing condition that has not worsened during participation in the study are not considered SAEs.
4) persistent or significant disability or incapacity (refers to a substantial disruption of one's ability to conduct normal life functions)
5) a congenital anomaly/birth defect
6) an important medical event that may not result in death, be life-threatening, or require hospitalization, but may jeopardize the patient and may require medical intervention to prevent 1 of the outcomes listed in this definition. Examples of such events are intensive treatment in an emergency room or at home for allergic bronchospasm; blood dyscrasias or convulsions that do not result in hospitalization; or the development of drug dependency or drug abuse. Note: Any suspected transmission of an infectious agent via a medicinal product is considered an important medical event.

An AE that does not meet any of the criteria for seriousness listed above are regarded as a nonserious AE Withdrawal Due to an Adverse Event Any patient who experiences an AE may be withdrawn from the study at any time at the discretion of the investigator. If a patient is withdrawn wholly or in part because of an AE, a blood sample is obtained for the measurement of study drug concentrations.

The patient is monitored at the discretion of the investigator (eg, until the event has resolved or stabilized, until the patient is referred to the care of a health care professional, or until a determination of a cause unrelated to the study drug or study procedure is made). The investigator must inform the Medical Monitor as soon as possible of all patients who are being considered for withdrawal due to AEs. Additional reports must be provided when requested.

Tolerability

Tolerability is evaluated in terms of the number (%) of patients who failed to complete the study and the number (%) of patients who failed to complete the study due to AEs.

Pregnancy

All pregnancies (pregnancies in women participating in the study and in partners of men participating in the study) that occur during the study, or within 14 days of completion of the study, are to be reported as an SAE.

Any patient becoming pregnant during the study is withdrawn. All patients (or partners of patients) who become pregnant is monitored to the completion or termination of the pregnancy. If the pregnancy continues to term, the outcome (health of the infant up to 8 weeks of age), including spontaneous or voluntary termination, details of birth, and presence or absence of any birth defect, congenital abnormalities, or maternal and newborn complications, is reported to the sponsor. Any complication of pregnancy is considered an AE or SAE, as appropriate.

If the pregnancy does not continue to term, 1 of the following actions are taken: For a spontaneous abortion, consider as an SAE; for an elective abortion due to developmental anomalies, consider as an SAE; and/or for an elective abortion not due to developmental anomalies, do not consider as an SAE.

Clinical Laboratory Tests

All clinical laboratory test results outside of the reference range is interpreted by the investigator as belonging to 1 of the following categories:
1) abnormal but not a clinically significant worsening
2) abnormal and a clinically significant worsening A laboratory test result that has significantly worsened (according to medical judgment) from the baseline result is recorded and monitored. An AE includes a laboratory or diagnostic test abnormality (once confirmed by repeat testing) that results in the withdrawal of the patient from the study, the temporary or permanent cessation of treatment with study drug, or medical treatment or further diagnostic work-up.

Clinical laboratory tests (serum chemistry including electrolytes, hematology and urinalysis) are performed at screening (Visit 0), baseline (Visit 1), Day 14 (Visit 2, electrolytes only), Day 28 (Visit 3), Day 42 (Visit 4), Day 56 (Visit 5), Day 84 or Early Termination (Visit 6), and at the follow-up visit.

Specific laboratory tests are performed as listed below.

Serum Chemistry

The following serum chemistry tests are performed:
calcium; phosphorus; sodium, magnesium; potassium; chloride; bicarbonate or carbon dioxide; glucose; blood urea nitrogen; creatinine; cholesterol; uric acid; ALT; AST; lactate dehydrogenase; gamma-glutamyl transpeptidase (GGT), alkaline phosphatase; creatine phosphokinase (in case of elevated creatine phosphokinase, the MB fraction should be measured); total protein, albumin; total bilirubin; direct bilirubin; indirect bilirubin; and prolactin.

Hematology

The following hematology tests are performed:
Hemoglobin; hematocrit; red blood cell (RBC) count; platelet count; white blood cell (WBC) count and differential count; absolute neutrophil count; absolute lymphocyte count; absolute eosinophil count; absolute monocytes count; absolute basophil count; and absolute atypical lymphocyte count.

Urinalysis

Urinalysis includes testing for the following:

Protein; glucose; ketones; blood (hemoglobin); pH; specific gravity; leukocyte esterase; microscopic; bacteria; RBCs; WBCs; casts; and crystals.

Pregnancy Tests

Human chorionic gonadotropin (HCG) serum test is performed for all women of childbearing age at screening. (Visit 0). HCG urine tests are performed for all women of childbearing age at Day 28 (Visit 3), Day 56 (Visit 5), Day 84 or Early Termination (Visit 6), at the follow-up visit, and if clinically indicated at any other time. Any patient who becomes pregnant during the study is withdrawn.

Vital Signs

Vital signs are measured at screening (Visit 0), baseline (Visit 1), Day 14 (Visit 2), Day 28 (Visit 3), Day 42 (Visit 4), Day 56 (Visit 5), Day 84 or Early Termination (Visit 6), and at the follow-up visit. Vital signs include the following: pulse, blood pressure, body temperature.

Before pulse and blood pressure are measured, the patient must be in a position and resting for at least 5 minutes. Where applicable, measurements should be taken prior to blood being drawn for clinical laboratory evaluations. The same arm should be used each time vital signs are measured for a given patient. For any abnormal vital sign finding, the measurement should be repeated as soon as possible. Any vital sign value that is judged by the investigator as a clinically significant change (worsening) from a baseline value is considered an AE and monitored.

Electrocardiography

A single resting 12-lead ECG is conducted at screening (Visit 0). If there is evidence of a prolonged QTcF interval at screening (defined as a QTcF interval of >450 msec for males or >470 msec for females) then the ECG is repeated twice, and the mean of the 3 screening measurements are used to determine whether or not the patient is suitable for inclusion in the study.

ECGs are performed in triplicate prior to dosing on site and 1 to 2 hours after dosing on site at baseline (Visit 1), Day 14 (Visit 2), Day 28 (Visit 3), Day 42 (Visit 4), and Day 84 or Early Termination (Visit 6). At the discretion of the investigator, 12-lead ECG measurements can also be performed on Day 56 (Visit 5) where there are clinical circumstances that justify an additional ECG, e.g., patients with a previous episode of hypokalemia without QT prolongation.

Additional 12-lead ECG evaluations should be performed, at the investigators discretion, 1 to 2 hours after the afternoon dose for patients who, after their morning dose, show an increase from baseline in their QTcF value >50 msec. The machine produced QTcF value from the morning ECG is compared to the central ECG vendor reported Baseline QTcF; if the change is >50 msec then the afternoon ECG evaluations are performed. This optional afternoon ECG measurement is included for safety reasons, as the concentration of study drug may be higher in the afternoon than in the morning.

ECG is also performed in triplicate at the follow-up visit only for patients with a previously observed cardiac concern and/or QTc change from baseline.

Where applicable, ECG measurements should be taken prior to vital sign measurements and blood being drawn for clinical laboratory or PK evaluations.

A qualified physician at the central ECG vendor is responsible for interpreting the ECG. However, every ECG should be reviewed immediately at site in order to detect any QTcF prolongation of potential clinical concern and allow dosing.

Any ECG finding that is judged by the investigator or the physician from the central ECG vendor as a clinically significant change (worsening) compared with a baseline value is considered an AE, recorded on the source documentation and transcribed onto the CRF, and monitored as described.

Physical and Neurological Examinations

Physical and neurological examinations, including weight is performed at screening (Visit 0), baseline (Visit 1), Day 14 (Visit 2), Day 28 (Visit 3), Day 42 (Visit 4), Day 56 (Visit 5), Day 84 or Early Termination (Visit 6), and at the follow-up visit. Any physical or neurological examination finding that is judged by the investigator as a clinically significant change (worsening) compared with a baseline value is considered an AE and monitored.

Height is measured at the screening visit only.

Other Safety Measures and Variables

Concomitant Therapy or Medication

Concomitant therapy or medication usage is monitored throughout the study.

Columbia Suicide Severity Rating Scale

The C-SSRS is used to rate the patient's degree of suicidal ideation on a scale ranging from "no suicidal ideation" to "active suicidal ideation with specific plan and intent". (Posner 2011) The C-SSRS is completed at screening (Visit 0), baseline (Visit 1), Day 28 (Visit 3), Day 42 (Visit 4), Day 56 (Visit 5), and Day 84 or Early Termination (Visit 6) Patients with active suicidal ideation, as measured by a score of 4 or 5 on the C-SSRS at the screening visit, are not eligible for the study.

Assessment of Pharmacokinetics and Pharmacogenomics

Pharmacokinetic Variables

The primary PK measure is determination of plasma concentration of pridopidine. Concentrations are also incorporated into a pridopidine population PK model and individual exposure for the study patients (Cmax and AUC) is calculated.

Blood Sampling and Handling

Blood samples (4 mL each) are collected for the determination of plasma concentrations via venipuncture or indwelling catheter in the morning before study drug administration at the following visits:

Titration Period:
  Day 0 (baseline)-predose and 1 to 2 hours postdose
  Day 14-predose and 1 to 2 hours postdose
Full Treatment Dose Period:
  Day 28-predose and 1 to 2 hours postdose
  Day 42-predose, 1 to 2 hours postdose, and before leaving the site
  Day 84-predose, 1 to 2 hours postdose, and before leaving the site
  Follow-up visit A total of 13 samples are drawn from each patient for PK analysis. In case of an SAE, the aim is to collect an additional PK sample at the closest time possible to the SAE. The date and time of each PK sample and the dates and times of the last drug administration prior to any collected PK sample is recorded on the source documentation and transcribed onto the CRF. When ECG evaluation is scheduled at the same time as blood collection, ECG is performed before blood collection.

Samples are collected in potassium ethylene diamine tetra acetate-containing tubes. Immediately following collection, samples are cooled and centrifuged within 45 minutes at approximately 4° C. at 1500×g for 15 minutes. The plasma is then transferred into 2 polypropylene tubes (first aliquot [Set A] and back-up [Set B]) and stored below −20° C. until bioanalysis.

Analysis of Samples

Samples are analyzed using an appropriate validated method for pridopidine and its main metabolite TV-45065 (previously called ACR30). The lower limits of quantification for pridopidine and TV-45065 in plasma are approximately 1.6 to 1.8 ng/ml and 1.5 to 1.9 ng/mL, respectively. Incurred sample reanalysis may be performed.

Pharmacogenomic Variables

A blood sample (6 mL) is collected at the screening visit for potential genetic analyses. Analyses includes CAG repeats, CYP2D6 status, and genetic long QT syndrome (assessed only in patients experiencing QT prolongation following study drug administration leading to study discontinuation), or any other genetic analyses related to pridopidine response or HD.

Pharmacogenetic samples are sent to the laboratory within 72 hours from collection in ambient. If DNA extraction is not performed at the laboratory within 24 hours, the samples should be stored at −70° C. until DNA extraction is performed. After DNA extraction, the samples are stored either at −20° C. or −70° C.

Statistics

Study Design and Randomization

This is a double-blind, randomized, placebo-controlled, parallel-group study to evaluate the efficacy and safety of pridopidine treatment in patients with HD. Patients are randomly assigned to receive treatment with pridopidine at a dosage of 45, 67.5, 90, or 112.5 mg bid or a matching placebo in a 1:1:1:1:1 ratio.

Sample Size and Power Considerations

Approximately 50 patients per arm enables a power of 80% to detect a beneficial effect of 4.5 points or more in the change from baseline in TMS of an active pridopidine arm compared to placebo, assuming SD of 7.8 (as estimated from the MermaiHD [ACR16C008] study) and type I error of 5%.

Analysis Sets/Populations

Intent-to-Treat Population

The intent-to-treat (ITT) population includes all randomized patients. In this population, treatment is assigned based on the treatment to which patients were randomized, regardless of which treatment they actually received.

Safety Population

The safety population includes all randomized patients who receive at least 1 dose of study drug. In this population, treatment is assigned based upon the treatment patients actually receive, regardless of the treatment to which they were randomized.

Pharmacokinetic Population

The PK population includes all randomized patients who received at least 1 dose of study drug and had sufficient plasma concentration results available to allow the intended PK analysis. Patients are assigned to the treatment actually received regardless of the treatment assignment.

Full Analysis Set (FAS)

The full analysis set (FAS) includes all patients in the ITT population who receive at least 1 dose of study drug and have at least 1 postbaseline efficacy assessment.

Completers Analysis Set

The completers analysis set includes all patients in the ITT population who completed the study.

Data Handling Conventions

For all variables, only the observed data from the patients is used in the statistical analyses. Repeated measures models are used to estimate treatment effects at the end of the double blind treatment.

Study Population

The ITT population is used for all study population summaries unless otherwise noted. Summaries is presented by treatment group and for all patients. The Safety population is used for safety variables. The FAS is used for efficacy variables. The primary efficacy variable is analyzed also in the Completers analysis set.

Patient Disposition

Data from patients screened, patients screened but not treated, patients in the safety population and FAS, patients who complete the study, and patients who withdraw from the study are summarized using descriptive statistics. Data from patients who withdraw from the study is also be summarized by reason for withdrawal using descriptive statistics.

Demographic and Baseline Characteristics

Patient demographic and baseline characteristics are examined to assess the comparability of the treatment groups and are summarized using descriptive statistics. For continuous variables, descriptive statistics (number, mean, SD, standard error, median, minimum, and maximum) are provided. For categorical variables, patient counts and percentages are provided. Categories for missing data are presented if necessary.

Efficacy Analysis

Primary Efficacy Variable

The primary efficacy variable for this study is change from baseline in the UHDRS-TMS at Week 12.

Secondary Functional Efficacy Variables

CIBIC-Plus global score at Week 12 as compared to baseline (rated by an independent investigator)
    Change from baseline in the PDS score at Week 12
    Change from baseline in UHDRS-FA at Week 12

Other Functional Efficacy Variables

CGI-C at Week 12 as compared to baseline (rated by the study investigator and the patient)
    Change from baseline in UHDRS-TFC at Week 12
    Change from baseline in UHDRS-IS at Week 12

Exploratory/Other Variables

Global/Functional Scales:
    Change from baseline in HD-QoL at Week 12
    Change from baseline in MSWS-12 at Week 12
    Change from baseline in the PPT at Week 12

TMS Subscores:

Change from baseline in hand movement score at Week 12
    Change from baseline in Gait and balance score at Week 12
    Change from baseline in UHDRS-mMS at Week 12
    Percent of responders defined as patients with TMS change from baseline ≤0 at Week 12

Other Motor Assessments:

Change from baseline in Q-Motor measurements at Week 12
    Change from baseline in the TUG test at Week 12

Cognitive/Psychiatric Assessments:

Change from baseline in CAB brief at Week 12
    Change from baseline in PBA-s at Week 12

Planned Method of Analysis

The FAS is used for all efficacy analyses. Summaries are presented by treatment group.

Primary Efficacy Analysis

The change from baseline in TMS is analyzed using a Repeated Measures model (SAS® MIXED procedure with REPEATED sub-command). The model includes the following fixed effects: categorical week in trial by treatment interaction, center, neuroleptic use or no use and baseline TMS score. The unstructured covariance matrix for repeated observations within patients is used. In case that the model does not converge, the Maximum-Likelihood (ML) estimation method is used instead of the default Restricted ML (REML). If the model still does not converge then a simpler covariance structures with less parameters is used, according to the following order: Heterogeneous Autoregressive(1) (ARH(1)), Heterogeneous Compound Symmetry (CSH), Autoregressive(1) (AR (1)), and Compound Symmetry (CS). The means at the Week 12 visit of the change from baseline in TMS is compared between the active treatment arms and the placebo arm.

Secondary Functional Efficacy Variables Analyses

The secondary efficacy endpoints are analyzed in the same way as the primary efficacy endpoint except that the efficacy endpoint evaluation at baseline is included in the model instead of baseline TMS. For CIBIC-Plus, the CIBIS score at baseline is included in the model instead of baseline TMS.

Other Functional Efficacy Variables Analyses

The other functional efficacy endpoints are analyzed in the same way as the primary efficacy endpoint except that the efficacy endpoint evaluation at baseline is included in the model instead of baseline TMS. For CGI-C, the CGI-S score at baseline is included in the model instead of baseline TMS.

Exploratory/Other Efficacy Analyses

The exploratory/other efficacy endpoints are analyzed in the same way as the primary efficacy endpoint except that the efficacy endpoint evaluation at baseline is included in the model instead of baseline TMS.

Pharmacokinetic/Pharmacodynamic Analyses

A PK/PD model is developed to describe the relationship between exposure and UHDRS-TMS. The model consists of the following elements: (i) structural function relating UHDRS-TMS, pridopidine exposure (dose, AUC), and time; (ii) variance components characterizing inter-patient variability in model parameters; (iii) variance components characterizing residual variability. Model evaluation and selection are based on standard model diagnostics, goodness of fit criteria and simulation-based assessments (eg, posterior predictive checks). Similar PK/PD models are attempted for the secondary efficacy endpoints.

Pooling of Small Centers

Centers with low number of patients are pooled according to geographical region. The pooled center variable is used in all statistical models that include center as covariate.

Multiple Comparisons and Multiplicity

The Hochberg's Step-Up method for multiple comparisons between treatment arms and multiple secondary endpoints is used to maintain the experiment-wise type I error of 5% level. First, the Hochberg method is applied for the 4 comparisons of the 4 active doses to placebo. Then, any statistically significant dose continues to be tested for the 3 secondary endpoints using the Hochberg method.

Safety Variables and Analysis

Safety Variables

The overall safety and tolerability of pridopidine treatment are assessed throughout the study by evaluating AEs and the following additional safety variables:

clinical laboratory tests
vital signs
12-lead ECG

Safety Analysis

All AEs are coded using the Medical Dictionary for Regulatory Activities (MedDRA). Each patient is counted only once in each preferred term or SOC category for the analyses of safety. Summaries are presented for all AEs (overall and by severity), AEs determined by the investigator to be related to study treatment (ie, reasonable possibility) (defined as related or with missing relationship) (overall and by severity), serious AEs, and AEs causing withdrawal from the study. Summaries are presented by treatment group and for all patients. Patient listings of SAEs and AEs leading to withdrawal are presented.

Changes in laboratory and vital signs measurement data are summarized descriptively. All values are compared with prespecified boundaries to identify potentially clinically significant changes or values, and such values are listed.

The use of concomitant medications are summarized by therapeutic class using descriptive statistics. Concomitant medications includes all medications taken while the patient is treated with study drug.

For continuous variables, descriptive statistics (n, mean, SD, standard error, median, minimum, and maximum) are provided for actual values and changes from baseline to each time point. For categorical variables, patient counts and percentages are provided. Descriptive summaries of SAEs, patient withdrawals due to AEs, and potentially clinically significant abnormal values (clinical laboratory or vital signs) based on predefined criteria are also provided.

Pharmacokinetic Analysis

Plasma concentration data on pridopidine and the main metabolite TV-45065 are presented by descriptive statistics by dose of pridopidine and also by CYP2D6 metabolizer status.

Concentrations are also incorporated into a pridopidine's population PK model and individual exposure for the study patients (Cmax and AUC) are calculated. A correlation between Cmax/AUC and efficacy and safety measures is done. Other exploratory analysis and additional covariate analysis may also be done.

Results

Statistically significant changes from baseline in TMS, after 12 weeks of pridopidine administration at 67.5 mg. 90 mg, and 112.5 mg bid are observed. Alternatively, statistically significant changes are observed in the protocol prespecified motor domain sub scores hereof. These changes indicate that administration of pridopidine at the specified dosages allows for the successful treatment of motor impairment in patients afflicted with HD. Change from baseline is also observed for secondary efficacy variables and endpoints and other functional variables and endpoints described herein, indicating that pridopidine administered at the specified dosages allows for the treatment of motor, mental, functional or cognitive impairment in patients afflicted with HD.

Example 2

A Phase II, Dose-finding, Randomized, Parallel-Group, Double-Blind, Placebo-Controlled Study, Evaluating the Safety and Efficacy of Pridopidine 45 mg, 67.5 mg, 90 mg, and 112.5 mg Twice-Daily versus Placebo for Symptomatic Treatment in Patients with Huntington's Disease The present study assesses the efficacy of pridopidine 67.5 to 112.5 mg twice daily (bid) on motor impairment in patients with HD after 26 weeks of treatment using the Unified Huntington's Disease Rating Scale (UHDRS) Total Motor Score (TMS). The study also assesses the effect of 26 weeks of treatment with pridopidine 67.5 to 112.5 mg bid on the physical performance test (PPT). The study also (i) evaluates the safety and tolerability of a range of pridopidine doses in patients with HD during 26 weeks of treatment, (ii) explores the pharmacokinetics (PK) of pridopidine in the study population and (iii) investigates the relationship between exposure to pridopidine and outcome measures (eg, clinical efficacy and toxicity parameters)

Study Design

General Design and Study Schema

This is a multicenter, multinational, randomized, parallel-group, double blind, placebo controlled study to compare the efficacy and safety of pridopidine 45, 67.5, 90, and 112.5 mg bid versus placebo in the treatment of motor impairment in HD. The 45 mg dose level is not formally included in the efficacy analyses. A total of approximately 300 patients are enrolled (60 patients within each treatment arm).

Patients are equally randomized as in Example 1. Patients are screened as in Example 1.

During titration (Days 0 to 27), there are 2 on site visits: at Day 0 (baseline) and at Day 14. There are additional phone calls on Days 6 and 20. At the baseline visit, the procedure is the same as in Example 1, except that (i) the study investigator assesses the PPT and (ii) UHDRS-TMS and PPT are evaluated prior to the other scales.

Phone calls on Days 6 and 20 are performed to inquire about AEs and concomitant medications, and to allow the weekly dose increase on the following day During the on-site visit at Day 14, before the afternoon dose of the study drug, a blood sample is taken for electrolyte monitoring; if hypokalemia is observed, dosing is interrupted until normal electrolyte values are confirmed and maintained for 7 days. Vital signs are assessed in addition to the inquiry about AEs and concomitant medications. Twelve lead ECGs are performed in triplicate 1 to 2 hours after the afternoon dose of study drug on Day 14, followed by collection of a PK sample.

During the full treatment dose period (Days 28 to 182), there is a total of 7 on-site visits at Days 28, 42, 56, 84, 112, 140, and 182 (or at early termination) and a phone call on Day 35. Visits and procedures during the full dose period are scheduled around the afternoon dose, with the exception of Day 182 where only the morning dose is administered. During the phone call at Day 35, inquiries about AEs and concomitant medication are conducted At each of the on site visits, safety variables are assessed, including triplicate ECG evaluation before and 1 to 2 hours after dose administration at the site (ECG is optional on Day 56), and clinical laboratory evaluations. PK sampling for determination of the levels of pridopidine and TV 45065 are done on Days 28, 42, and 112 (before and 1 to 2 hours after the afternoon dose), on Days 84 and 140 (1 to 2 hours after the afternoon dose), and on Day 182 (before the morning dose). When concomitant to ECG, PK samples are collected after the ECG recording.

At Days 28, 56, 84, 112, 140, and 182, in addition to safety assessments, the CIBIC Plus is rated by an independent rater, while the study investigator assesses the UHDRS-TMS, the PPT, the PDS, the Clinical Global Impression of Change (CGI C), the TUG, the PPT, the UHDRS FA, the UHDRS TFC, the UHDRS IS, the CAB brief, and the PBA s. The patient fills the MSWS 12 and the HD QoL scales and Q-Motor assessments are performed. PPT and UHDRS-TMS and PPT are evaluated prior to the other scales Patients who complete all scheduled visits have final procedures and assessments performed at the final visit (Day 182). Patients who withdraw from the study before completing the evaluation period have the Day 112 procedures and assessments performed at their final visit.

There are a follow up visit 2 weeks after last dose of study drug for safety evaluation, including a triplicate ECG evaluation (optional) and PK sample. At this visit, UHDRS TMS and Q Motor are also assessed. Patients who complete this study may have the opportunity to enter an open label extension study.

Figure 2:
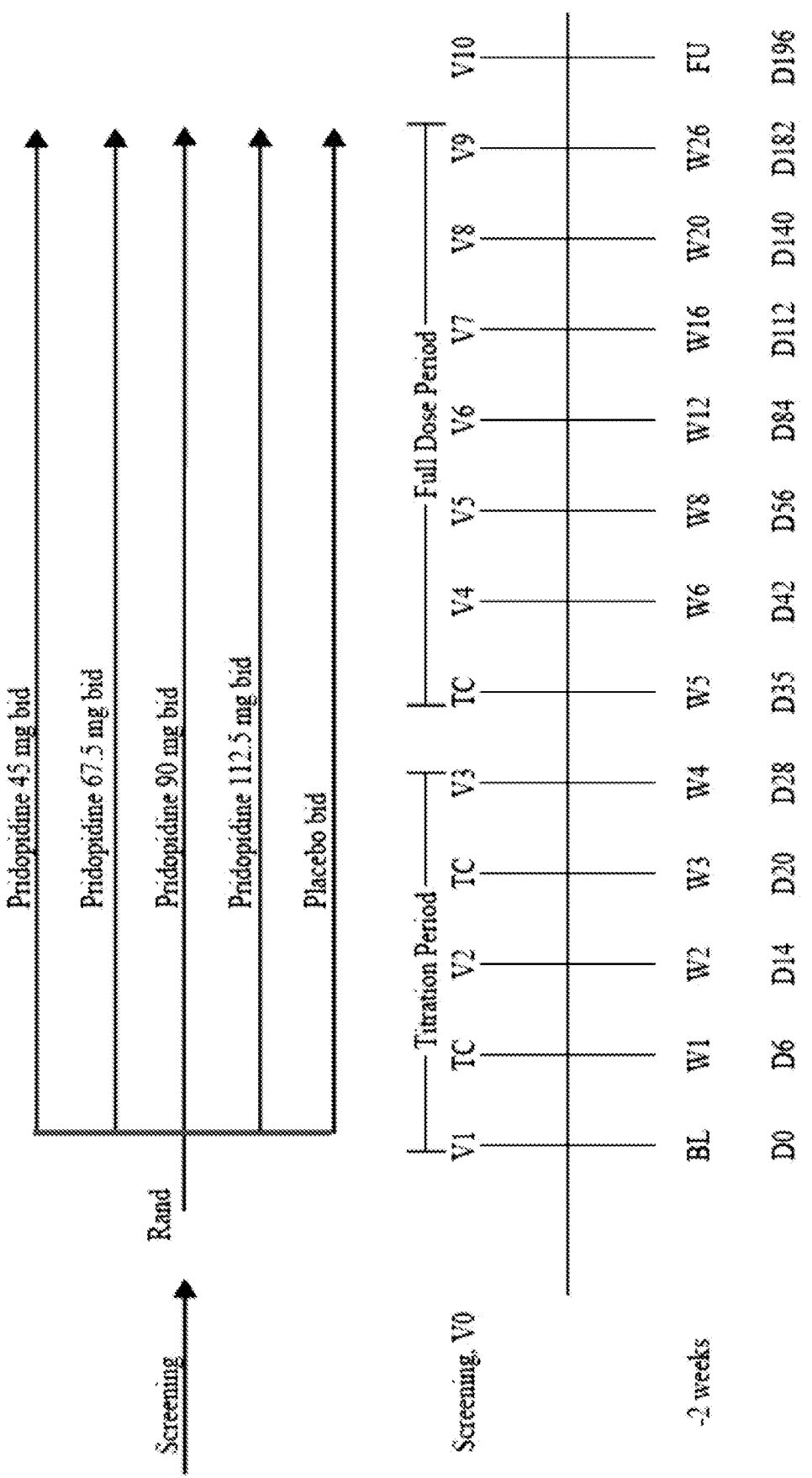
FIG. 2: Overall Study Schema of Example 2.

The study schema for Example 2 is presented in FIG. 2.

Primary and Secondary Variables and Endpoints

The primary efficacy variable and endpoint for this study is change from baseline in the UHDRS TMS (defined as the sum of all UHDRS motor domains ratings) at Week 26. The secondary efficacy variable and endpoint is change from baseline in the PPT at Week 26.

Other Efficacy Variables and Endpoints

Other efficacy variables and endpoints for this study are as follows:

Global Functional Scales:
  CIBIC-Plus global score at Week 26 as compared to baseline (rated by an independent investigator)
  Change from baseline in the PDS score at Week 26
  Change from baseline in UHDRS FA at Week 26
  CGI C at Week 26 as compared to baseline (rated by the study investigator and the patient)
  Change from baseline in UHDRS TFC at Week 26
  Change from baseline in UHDRS IS at Week 26

Global/Functional Scales:
  Change from baseline in HD QoL at Week 26
  Change from baseline in MSWS 12 at Week 26

TMS Subscores:
  Change from baseline in hand movement score (defined as the sum of UHDRS domains finger taps, pronate-supinate hands and luria [fist-hand-palm test]) at Week 26
  Change from baseline in Gait and balance score (defined as the sum of UHDRS domains gait, tandem walking and retropulsion pull test) at Week 26
  Change from baseline in UHDRS mMS (defined as the sum of UHDRS domains dysarthria, tongue protrusion, finger taps, pronate-supinate hands, luria, rigidity, bradykinesia, gait, tandem walking, retropulsion pull test) at Week 26
  Change from baseline in UHDRS Chorea at Week 26
  Change from baseline in UHDRS Dystonia at Week 26
  Responders, defined as patients with UHDRS TMS change from baseline ≤0 at Week 26

Other Motor Assessments:
  Change from baseline in Q Motor measurements at Week 26 including digitomotography (speeded index finger tapping), dysdiadochomotography (pronation/supination hand tapping), manumotography and choreomotography (grip force and chorea analysis) and pedomotography (speeded foot tapping)
  Change from baseline in the TUG test at Week 26

Cognitive/Psychiatric Assessments:
  Change from baseline in CAB brief at Week 26: SDMT, Emotion Recognition, Trail Making Test, HVLT-R, Paced Tapping at 3 Hz, OTS
  Change from baseline in PBA-s at Week 26

Safety Variables and Endpoints

Safety variables and endpoints include the following:
  AEs throughout the study
  Changes from baseline in QTcF and other ECG parameters throughout the study
  Clinical safety laboratory (clinical chemistry, hematology, and urinalysis) throughout study Changes from baseline C-SSRS throughout the study
Vital signs throughout the study
Tolerability Variables and Endpoints
Tolerability variables and endpoints include the following:
the number (%) of patients who failed to complete the study
the number (%) of patients who failed to complete the study due to AEs
Pharmacokinetic Variables and Endpoints
The primary PK measure is determination of plasma concentration of pridopidine. Concentrations are also incorporated into a pridopidine population PK model and individual exposure for the study patients (Cmax and AUC) is be calculated.
Randomization and Blinding
Randomization is performed by interactive response technology (IRT) using dynamic randomization to balance the treatment arms within centers and neuroleptics use or no use. Patients are equally assigned to the 5 treatment arms of the study (4 active treatment arms and placebo, allocation ratio of 1:1:1:1:1). Pridopidine capsules sizes differ between the 22.5 and 45 mg dosages, therefore 2 different sizes of placebo capsules are provided, depending on treatment arm, to maintain blinding. Packaging of all treatment packs are identical in appearance in order to maintain blinding throughout each study period. The investigators, the sponsor, and any personnel involved in patients' assessment, monitoring, analysis and data management (excluding the designated Clinical Supplies Chain's personnel), are blinded to the patient assignment until the database is locked for analysis and the treatment assignment revealed.

Study Drugs and Dosage
Study drug (pridopidine and matching placebo) is administered as described below, and as summarized in Table 4.
Investigational Product and Dosage
Pridopidine is provided as in Example 1 and the titration period procedure is the same as Example 1. The full dose period is the same as in Example 1, except that it is from Week 4 (Day 28 Only) to Week 26 instead of from Weeks 5 to 12. The Other Study Drugs and Dosage in Example 2 is the same as Example 1.
Duration of Patient Participation
For each patient, the duration of participation is up to 30 weeks, consisting of a screening period of up to 2 weeks, a 26 week randomized double-blind treatment period (comprised of a 4 week titration and 22 week full dose period), and a 2 week follow-up period following the last dose of study medication. The total duration of the study is approximately 15 months.
Study Procedures
Study procedures and assessments with their timing are summarized in Table 5.

TABLE 4

Dose Administration (Capsules are Administered Twice Daily to Give the Total Daily Dose)

| Treatment | Titration Period | | | | Full Dose Period |
|---|---|---|---|---|---|
| | Week 1 | Week 2 | Week 3 | Week 4[a] | Weeks 4[b] to 26 |
| Pridopidine 45 mg bid | 1 × 22.5 mg Pridopidine<br>1 × 22.5 mg Placebo<br>1 × 45 mg Placebo<br>(TDD = 45 mg) | 1 × 22.5 mg Pridopidine<br>1 × 22.5 mg Placebo<br>1 × 45 mg Placebo<br>(TDD = 45 mg) | 1 × 22.5 mg Pridopidine<br>1 × 22.5 mg Placebo<br>1 × 45 mg Placebo<br>(TDD = 45 mg) | 1 × 22.5 mg Pridopidine<br>1 × 22.5 mg Placebo<br>1 × 45 mg Placebo<br>(TDD = 45 mg) | 1 × 45 mg Pridopidine<br>1 × 22.5 mg Placebo<br>1 × 45 mg Placebo<br>(TDD = 90 mg) |
| Pridopidine 67.5 mg bid | 1 × 22.5 mg Pridopidine<br>1 × 22.5 mg Placebo<br>1 × 45 mg Placebo<br>(TDD = 45 mg) | 1 × 22.5 mg Pridopidine<br>1 × 22.5 mg Placebo<br>1 × 45 mg Placebo<br>(TDD = 45 mg) | 1 × 45 mg Pridopidine<br>2 × 22.5 mg Placebo<br>(TDD = 90 mg) | 1 × 45 mg Pridopidine<br>2 × 22.5 mg Placebo<br>(TDD = 90 mg) | 1 × 22.5 mg Pridopidine<br>1 × 45 mg Pridopidine<br>1 × 45 mg Placebo<br>(TDD = 135 mg) |
| Pridopidine 90 mg bid | 1 × 22 .. 2.5 mg Pridopidine<br>1 × 22.5 mg Placebo<br>1 × 45 mg Placebo<br>(TDD = 45 mg) | 1 × 45 mg Pridopidine<br>2 × 22.5 mg Placebo<br>(TDD = 90 mg) | 1 × 45 mg Pridopidine<br>1 × 22.5 mg Pridopidine<br>1 × 22.5 mg Placebo<br>(TDD = 135 mg) | 1 × 45 mg Pridopidine<br>1 × 22.5 mg Pridopidine<br>1 × 22.5 mg Pridopidine<br>1 × 22.5 mg Placebo<br>(TDD = 135 mg) | 2 × 45 mg Pridopidine<br>1 × 22.5 mg Placebo<br>(TDD = 180 mg) |
| Pridopidine 112.5 mg bid | 1 × 22.5 mg Pridopidine<br>1 × 22.5 mg Placebo<br>1 × 45 mg Placebo<br>(TDD) = 45 mg) | 1 × 45 mg Pridopidine<br>2 × 22.5 mg Placebo<br>(TDD = 90 mg) | 1 × 45 mg Pridopidine<br>1 × 22.5 mg Pridopidine<br>1 × 22.5 mg Placebo<br>(TDD = 135 mg) | 1 × 45 mg Pridopidine<br>2 × 22.5 mg Pridopidine<br>(TDD = 180 mg) | 1 × 22.5 mg Pridopidine<br>2 × 45 mg Pridopidine<br>(TDD = 225 mg) |
| Placebo | 2 × 22.5 mg Placebo<br>1 × 45 mg Placebo | 2 × 22.5 mg Placebo<br>1 × 45 mg Placebo | 2 × 22.5 mg Placebo<br>1 × 45 mg Placebo | 2 × 22.5 mg Placebo<br>1 × 45 mg Placebo | 1 × 22.5 mg Placebo<br>2 × 45 mg Placebo |

TDD = total daily dose;
[a]Excluding Day 28
[b]Day 28 only

TABLE 5

Study Procedures and Assessments

| | Titration Period | | | | | | Full Dose Period | | | | | | | | | |
|---|---|---|---|---|---|---|---|---|---|---|---|---|---|---|---|---|
| Visit | V0 | V1 | TC | V2 | TC | V3 | TC | V4 | V5 | V6 | V7 | V8 | V9 | V10 | | |
| Day | −14 to −1 | 0 | 6 | 14 ± 3 | 20 | 28 ± 4 | 35 ± 3 | 42 ± 5 | 56 ± 5 | 84 ± 7 | 112 ± 7 | 140 ± 7 | 182 ± 7 | 196 ± 7 | | |
| Procedures and assessments | Screening | BL | W1 | W2 | W3 | W4 | W5 | W6 | W8 | W12 | W16 | W120 | W26/ET | FU | Unsc. Visit |
| On-site visit | X | X | | X | | X | | X | X | X | X | X | X | X | X |
| Telephone call | | | X | | X | | X | | | | | | | | |
| Informed consent | X | | | | | | | | | | | | | | |
| Demography | X | | | | | | | | | | | | | | |
| Medical and psychiatric history | X | | | | | | | | | | | | | | |
| Prior medication history | X | | | | | | | | | | | | | | |
| Inclusion and exclusion criteria[a] | X | X | | | | | | | | | | | | | |
| Randomization | | X | | | | | | | | | | | | | |
| Clinical laboratory tests (hematology and biochemistry) | X | X | | X[b] | | X | | X | X | X | X | X | X | X | X |
| Urinalysis | X | X | | | | X | | X | X | X | X | X | X | X | X |
| Pregnancy test (women of childbearing potential)[c] | X | | | | | X | | X | X | X | X | X | X | X | X |
| Full physical and neurological examination, including weight (height at screening only) | X | | | X | | X | | X | X | X | X | X | X | X | X |
| ECG | X[d] | X[e] | | X[f] | | X[f] | | X[f] | X[g] | X[f] | X[f] | X[f] | X[h] | X[i] | X |
| Vital signs measurement | X | X | | X | | X | | X | X | X | X | X | X | X | X |
| C-SSRS (baseline version) | X | | | | | | | | | | | | | | |
| C-SSRS (since last visit version) | | X | | | | X | | X | X | X | X | X | X | | |
| Blood sample for genetic analyses[j] | X | | | | | | | | | | | | | | |
| UHDRS-TMS | X | X[k] | | | | X[k] | | | X[k] | X[k] | X[k] | X[k] | X[k] | X | |
| UHDRS-FA | | X | | | | X | | | X | X | X | X | X | | |
| UHDRS-TFC | | X[k] | | | | X[k] | | | X[k] | X[k] | X[k] | X[k] | X[k] | | |
| UHDRS-IS | X | X | | | | X | | | X | X | X | X | X | | |
| PBA-s | | X | | | | X | | | X | X | X | X | X | | |
| CIBIS | | X[k] | | | | | | | | | | | | | |
| CIBIC-Plus | | | | | | X[k] | | | X[k] | X[k] | X[k] | X[k] | X[k] | | |
| PDS | | X[k] | | | | X[k] | | | X[k] | X[k] | X[k] | X[k] | X[k] | | |
| PPT | | X | | | | X | | | X | X | X | X | X | | |
| CGI-S | | X | | | | | | | | | | | | | |
| CGI-C | | | | | | X | | | X | X | X | X | X | | |
| HD-QoL | | X | | | | X | | | X | X | X | X | X | | |
| MSWS-12 | | X | | | | X | | | X | X | X | X | X | | |
| Q-Motor assessments[l] | X | X | | | | X | | | X | X | X | X | X | X | |
| TUG test | | X | | | | X | | | X | X | X | X | X | | |
| Cognitive assessment battery[m] | X | X | | | | X | | | X | X | X | X | X | | |
| Blood samples for drug concentration | | X[e] | | X[n] | | X[o] | | X[o] | | X[n] | X[o] | X[n] | X[h] | X[p] | X |
| Adverse event inquiry | X | X | X | X | X | X | X | X | X | X | X | X | X | X | X |
| Concomitant medication inquiry | X | X | X | X | X | X | X | X | X | X | X | X | X | X | X |
| Review of tolerability to study drug prior to dose escalation (if applicable) | | | X | X | X | | | | | | | | | | |

TABLE 5-continued

Study Procedures and Assessments

| | | Titration Period | | | | | Full Dose Period | | | | | | |
|---|---|---|---|---|---|---|---|---|---|---|---|---|---|
| | | | | | | | Visit | | | | | | |
| V0 | V1 | TC | V2 | TC | V3 | TC | V4 | V5 | V6 | V7 | V8 | V9 | V10 |
| | | | | | | | Day | | | | | | |
| −14 to −1 | 0 | 6 | 14 ± 3 | 20 | 28 ± 4 | 35 ± 3 | 42 ± 5 | 56 ± 5 | 84 ± 7 | 112 ± 7 | 140 ± 7 | 182 ± 7 | 196 ± 7 |
| | | | | | | | Procedures and assessments | | | | | | |

| | Screening | BL | W1 | W2 | W3 | W4 | W5 | W6 | W8 | W12 | W16 | W120 | W26/ET | FU | Unsc. Visit |
|---|---|---|---|---|---|---|---|---|---|---|---|---|---|---|---|
| Dispense/collect study drug | | X | | X | | X | | | X | X | X | X | X | X[q] | | |
| Review study compliance | | X | | X | | X | | X | X | X | X | X | X | | | |
| Study drug administration[1)] | | →  | | | | | | | | | | | | | | |

V = Visit (on site); TC = telephone call; BL = Baseline; W = Week; ET = early termination; FU = follow up; ECG = electrocardiogram; C SSRS = Columbia Suicide Severity Rating Scale; UHDRS = Unified Huntington's Disease Rating Scale; CIBIS = Clinician's Interview based Impression of Severity; CIBIC Plus = Clinician's Interview based Impression of Change plus Caregiver Input; CGI S = Clinical Global Impression of Severity; CGI C = Clinical Global Impression of Change; TUG = timed up and go; PDS = Physical Disability Scale; PPT = physical performance test; HD QoL = Huntington's disease Quality of Life; MSWS = Multiple Sclerosis Walking Scale; CAG = cytosine adenine guanine; TMS = Total Motor Score; IS = Independence Scale; PBA s = Problem Behaviors Assessment-Short form; TFC = Total Functional Capacity; FA = Functional Assessment; Q Motor = Quantitative motor; SAE = serious adverse event Table 5 Legand

[a] Inclusion/exclusion criteria should be met at screening and reviewed on Day 0 before the patient is randomized

[b] Electrolytes only

[c] Serum pregnancy test at screening (with urine test if required for confirmation); urine pregnancy test at subsequent time points. An indeterminate reading for the serum pregnancy test should be checked twice and the patient referred to a gynecologist if required.

[d] At screening, a single ECG is performed. If there is evidence of a prolonged QTcF interval at screening (defined as a QTcF interval of >450 msec) then the ECG is repeated twice, and the mean of the 3 screening measurements are used to determine whether or not the patient issuitable for inclusion in the study.

[e] At the Baseline visit, the predose QTcF is determined by the average of 3 ECGs (within 10 to 20 minutes of one another), each in triplicate (in total 9 recordings). A postdose ECG is performed in triplicate 1 to 2 hours after first dosing. PK samples are collected prior to and 1 to 2 hours after first dose administration at the site. When concomitant to ECG, PK samples are collected after the ECG recording.

[f] One ECG performed in triplicate prior and 1 to 2 hours post afternoon dose.

[g] ECG is optional on Day 56, to be performed at the investigator's discretion where there are clinical circumstances that justify an additional ECG, eg, patients with a previous episode of hypokalemia without QT prolongation

[h] On Day 182, a triplicate ECG and PK sample are collected before the last study (morning) dose.

[i] ECG is optional at the follow-up visit, but should be performed for all patients with a previously observed cardiac concern and/or QTc change from baseline

[j] Including CAG analysis, cytochrome P450 2D6 status, genetic long QT syndrome (assessed only in patients experiencing QT prolongation following study drug administration leading to study discontinuation), or any other genetic analyses related to pridopidine response or Huntington's disease

[k] Evaluated in priority

[l] Including digitomotography (speeded index finger tapping), dysdiadochomotography (pronation/supination hand tapping), manumotography and choreomotography (grip force and chorea analysis) and pedomotography (speeded foot tapping)

[m] Includes symbol digit modalities test, Stroop word reading test, abbreviated Montreal cognitive assessment scale, and Trail Making Test B

[n] On Days 14, 84, and 140, PK samples are collected 1 to 2 hours post afternoon dose. When concomitant to ECG, PK samples are collected after the ECG recording.

[o] On Days 28, 42, and 112, PK samples are collected prior and 1 to 2 hours post afternoon dose. When concomitant to ECG, PK samples are collected after the ECG recording. pAt the follow up visit, 1 PK sample are collected. In case of SAE, an additional PK sampling should be aimed to be collected at the closest time to SAE. When concomitant to ECG, PK samples are collected after the ECG recording.

[q] Collection only.

[r] Every patient receives 3 capsules twice daily (bid), ie, 3 capsules in the morning and 3 capsules in the afternoon (7 to 10 hours after the morning dose), during the whole study period. Study drug is not administered at Early Termination visit. At on-site visits, the afternoon dose is taken at the site.

The Procedures for Screening and Enrollment (Visit 0) are the same as Example 1 except that instead of the procedure to "collect blood sample for potential genetic analyses," the procedure is "collect blood sample for CAG analysis, CYP2D6 metabolizer status, genetic long QT syndrome (for determination in patients who had QT prolongation following study drug administration), or any other potential genetic analyses related to pridopidine response or HD"

The Procedures for Baseline Visit (Visit 1) are the same as in Example 1, except that the additional procedures are performed before dose on site and UHDRS-TMS and PPT should be evaluated prior to the other scales:

12 lead ECG in triplicate (performed after at least 5 minutes of supine rest); the predose QTcF is determined by the average of 3 ECGs (within 10 to 20 minutes of each other), each in triplicate (in total 9 readings), and CIBIS, UHDRS-TMS, UHDRS TFC, and PDS are evaluated prior to the other scales:

Additionally, a patient who does not meet study entry criteria on the basis of results of baseline assessments and is not enrolled in the study is not be considered for screening again. Patients who were considered acceptable for the study on the basis of their UHDRS TMS and UHDRS-IS results at screening are not excluded from the study based on their UHDRS TMS and UHDRS-IS results at baseline.

The Procedures for Baseline Visit (Visit 1) following administration of the first dose on site are the same as in Example 1, except that the 12 lead ECG in triplicate (1 to 2 hours after dose administration) (performed after at least 5 minutes of supine rest).

Procedures During Study Drug Treatment

Titration Period (Weeks 0 to 4)

Telephone Contact at Weeks 1 and 3 (Days 6 and 20)

Patients are contacted by telephone on Days 6 and 20 to evaluate tolerability to the study drug through assessment of AEs and concomitant medication usage, and to allow the weekly dose increase during the titration period (see above) that takes place on the following day (if applicable).

Week 2-Day 14 (Visit 2)

The following procedures/assessments are performed at Week 2 on Day 14 (±3 days) visit (Visit 2):

Before Afternoon Dosing:
- AE inquiry
- concomitant medication review
- clinical laboratory tests (electrolytes only); results for electrolytes are available before dosing
- full physical and neurological examination (including weight)
- vital signs measurements
- collect/dispense study drug
- study compliance review Following Afternoon Dosing:
- triplicate 12 lead ECG (1 to 2 hours after dose administration) (performed after at least 5 minutes of supine rest)
- obtain a 4 mL blood sample for plasma drug assay 1 to 2 hours after dose administration; PK samples are collected as close as possible to, but after the ECG recording.

Full Dose Period (Weeks 4 to 26)

Weeks 4, 6, 8, 12, 16, and 20-Days 28, 42, 56, 84, 112, and 140 (Visits 3 to 8)

The following procedures/assessments are performed in conjunction with afternoon dosing on Days 28 (±4 days), 42 (±5 days), 56 (±5 days), 84 (±7 days), 112 (±7 days), and 140 (±7 days), at Weeks 4, 6, 8, 12, 16, and 20 (Visits 3 to 8):

Before Afternoon Dosing:
- AE inquiry
- concomitant medication review
- clinical laboratory tests (hematology, biochemistry including electrolytes, urinalysis)
- Days 28, 56, 84, 112, and 140 only: urine pregnancy test for women of child bearing potential only
- full physical and neurological examination (including weight)
- triplicate 12 lead ECG (performed after at least 5 minutes of supine rest) (Note: ECG is optional on Day 56, and is performed at the investigator's discretion where there are clinical circumstances that justify an additional ECG, eg, patients with a previous episode of hypokalemia without QT prolongation)
- vital signs measurements
- C-SSRS (since last visit version)
- Days 28, 42, and 112 only: obtain a 4 mL blood sample for plasma drug assay (as close as possible to, but after the ECG recording)
- Days 28, 56, 84, 112, and 140 only: collect/dispense study drug
- study compliance review Following Afternoon Dosing:
- triplicate 12 lead ECG (1 to 2 hours after dose administration) (performed after at least 5 minutes of supine rest) (Note: ECG is optional on Day 56, and is performed at the investigator's discretion where there are clinical circumstances that justify an additional ECG, eg, patients with a previous episode of hypokalemia without QT prolongation)
- Days 28, 42, 84, 112, and 140 only: obtain a 4 mL blood sample for plasma drug assay 1 to 2 hours after dose administration; PK samples are collected as close as possible to, but after the ECG recording.

In addition, the following efficacy procedures/assessments are performed on Days 28, 56, 84, 112, and 140 only, either before or after the afternoon dose (with the time of the evaluation being recorded in the CRF), with UHDRS-TMS and PPT evaluated in priority: UHDRS-TMS, PPT, CIBIC-Plus, PDS, UHDRS-FA, UHDRS-TFC, UHDRS-IS, CGI-C, TUGtest, HD-QoL, MSWS-12, Q Motor assessments, CAB brief tests (SDMT, Stroop word reading test, abbreviated MoCA scale and Trail Making Test B), PBA-s Telephone Contact at Week 5 (Day 35)

Patients are contacted by telephone on Day 35 (±3 days) to evaluate tolerability to the study drug through assessment of AEs and concomitant medication usage.

Week 26-Day 182 (Visit 9) or Early Termination

The following procedures/assessments are performed on Day 182 (±7 days) at Week 26 (Visit 9) or at the Early Termination visit:

Before Dosing:
- AE inquiry
- concomitant medication review
- clinical laboratory tests (hematology, biochemistry including electrolytes, urinalysis)
- urine pregnancy test for women of child bearing potential only
- full physical and neurological examination (including weight)
- triplicate 12 lead ECG (performed after at least 5 minutes of supine rest)
- vital signs measurements
- C-SSRS (since last visit version)
- obtain a 4 mL blood sample for plasma drug assay (as close as possible to, but after the ECG recording)
- study compliance review
- morning study drug dose administration (conditional to potassium level being within normal range) (Note: study drug is not be administered if Early Termination visit)

After Dosing:
- collect remaining study drug

The following efficacy procedures/assessments are performed on Day 182 (Visit 9), before or after dosing (with the time of the evaluation being recorded in the CRF), with UHDRS-TMS and PPT evaluated in priority: UHDRS-TMS, PPT, CIBIC-Plus, PDS, UHDRS-FA, UHDRS-TFC, UHDRS-IS, CGI-C, TUGtest, HD-QoL, MSWS-12, Q-Motor assessments, CAB brief tests (SDMT, Stroop word reading test, abbreviated MoCA scale and Trail Making Test B), PBA-S There is no afternoon dose on Day 182/Early Termination.

Follow-up Visit

There is a follow up visit 2 weeks after the last dose of study drug (Day 196, ±7 days). The following procedures/assessments are performed:
- AE inquiry
- concomitant medication review
- clinical laboratory tests (hematology, biochemistry, urinalysis)
- urine pregnancy test for women of child bearing potential only
- full physical and neurological examination (including weight)
- optional triplicate 12 lead ECG (performed after at least 5 minutes of supine rest), should be performed for all patients with a previously observed cardiac concern and/or a clinically significant QTe change from baseline
- vital signs measurements
- UHDRS-TMS
- Q-Motor assessments
- obtain a 4 mL blood sample for plasma drug assay after ECG collection Procedures After Study Drug Treatment/Discontinuation Patients who are participating in the study in compliance with the protocol for at least 26 weeks of double blind treatment are considered to have completed the study. For patients who complete the study or withdraw prematurely, final evaluations are performed at the Week 26/Early Termination visit (Visit 9). For patients who do not have a final visit within 7 days after their last dose of study drug, efficacy evaluations are not be performed.

The Sections regarding Unscheduled Visits, Population Studied are the same in Example 2 as in Example 1.

Selection and Withdrawal of Patients

Inclusion/exclusion criteria is documented throughout the screening process and the investigator documents review of inclusion/exclusion criteria prior to randomization. The patients continue to meet inclusion/exclusion criteria at the Baseline visit. If a patient no longer meets inclusion/exclusion criteria at Baseline the subject is not eligible for the study. Baseline laboratory values are not known until after randomization; if there is a finding in the Baseline laboratory values cause the subject to be ineligible for the study, the site reviews this with the Medical Monitor.

The Patient Inclusion Criteria, Patient Exclusion Criteria and Withdrawal Criteria and Procedures in Example 2 is the same as in Example 1.

However, in Example 2 the following is added to the criteria:

"Patients with clinically significant heart disease at the screening visit" is defined as follows: (i) significant cardiac event (eg, myocardial infarction), angina pectoris or episode of congestive heart failure with symptoms >Grade 2 New York Heart Association classification within 12 weeks before randomization, or presence of cardiac disease that in the opinion of the investigator increased the risk of ventricular arrhythmia, (ii) history of arrhythmia (multifocal premature ventricular contractions, bigeminy, trigeminy, ventricular tachycardia) that was symptomatic or required treatment (Common Terminology Criteria for Adverse Events Grade 3), symptomatic or uncontrolled atrial fibrillation despite treatment, or asymptomatic sustained ventricular tachycardia, (iii) presence of left bundle branch block.

Cockcroft Gault equation is defined as (140 age)×mass (kg)×[0.85 if female]/72×serum creatinine (mg/dL)

The Treatment of Patients/Study Drugs Administered section in Example 1 is followed in Example 2.

The sections or procedures regarding (i) Prior and Concomitant Therapy or Medication, (ii) Permitted Medication and (iii) Prohibited Medication in Example 1 are followed in Example 2. However, additionally, if, according to investigator judgment, a change of usage or dosage of antipsychotic medication is required during the study, this is recorded in the CRF and discussed with the medical monitor. Also, Bupropion is an antidepressant drug potentially administered to study patients. Although no PK interactions are expected between bupropion and pridopidine, bupropion is associated with seizures in approximately 0.4% (4/1000) of patients treated at doses up to 450 mg/day. This incidence of seizures may exceed that of other marketed antidepressants by as much as 4-fold (Wellbutrin label). Retrospective analysis of clinical experience gained with bupropion suggests that the risk of seizure may be minimized if the total daily dose of bupropion does not exceed 450 mg, the daily dose is administered 3 times daily (with each single dose not to exceed 150 mg, and the rate of incrementation of dose is very gradual.

Total Blood Volume

The total volume of blood estimated to be collected from each patient is detailed in Table 6

TABLE 6

Total Blood Volume Collected from Each Patient

| Type of Assessment | Number of Samples Collected | Volume per Sample | Total Volume for Assessment |
|---|---|---|---|
| Pharmacokinetic | 13 | 4 mL | 52 mL |
| Serum Chemistry | 11 | 10.5 mL | 115.5 mL |
| Hematology | 9 | 3 mL | 27 mL |
| Pharmacogenetic Analyses | 3 | 10 mL | 10 mL |
| Total | | | 204.5 mL |

CAG = cytosine-adenosine-guanine;
CYP2D6 = cytochrome P450 2D6

Assessment of Efficacy

Except where stated, efficacy assessments detailed in the following sections are performed on Day 0 (Visit 0, baseline), Day 28 (Visit 3), Day 56 (Visit 5), Day 84 (Visit 6), Day 112 (Visit 7), Day 140 (Visit 8), and Day 182 (Visit 9). Except for at Day 0, efficacy assessments can take place before or after the afternoon dose, with the time of the evaluation being recorded in the CRF. UHDRS-TMS and Q-Motor assessments are also performed at the follow-up visit.

The Primary Efficacy Variable and Endpoint in Example 2 is the same as in Example 1.

Secondary Efficacy Variable and Endpoint

Physical Performance Test

The PPT is described in Example 1. The secondary efficacy analysis variable for this study is the change from baseline in the PPT at Week 26

Other Efficacy Variables and Endpoints

Other efficacy variables and endpoints are described in the following sections.

Clinician Interview Based Impression of Change plus Caregiver Input

Global change in HD at Week 26 is measured as described in Example 1.

At each subsequent visit in which the evaluation is performed (Visits 3, 5, 6, 7, 8, and 9), the CIBIC-Plus is administered as described in Example 1. However, for the purposes of this study, a caregiver is recommended to be someone who attends to the patient at least 2 to 3 times per week for at least 3 hours per occasion, and the suitability of the caregiver is judged by the investigator. Where possible, the same person acts as a patient's caregiver throughout the study. If this is not possible, a patient preferably has no more than 2 caregivers throughout the study.

Physical Disability Scale

The PDS is used during the study as described in Example 1.

UHDRS Functional Assessments

The FA scale of the UHDRS assesses functionality as in Example 1.

Clinical Global Impression of Severity and Change

CGI-S is assessed at baseline (Day 0) and CGI-C is used at all subsequent time points (Visits 3, 5, 6, 7, 8, and 9) to assess changes from baseline. The CGI-S and CGI-C are described in Example 1.

UHDRS Total Functional Capacity

The TFC scale of the UHDRS assesses 5 functional domains associated with disability (occupation, finances, domestic chores, activities of daily living, and care level).

UHDRS Independence Scale

The independence scale of the UHDRS is described in Example 1.

Global/Functional Scales

Huntington's Disease Quality of Life

The HD-QoL is described in Example 1.

Multiple Sclerosis Walking Scale

MSWS-12 is described in Example 1.

Total Motor Score Subscores

UHDRS Hand Movement Score

The hand movement score is described in Example 1.

UHDRS Gait and Balance Score

The gait and balance score is described in Example 1.

UHDRS Modified Motor Scale

The UHDRS-mMS is defined as the sum of following domains from UHDRS-TMS: dysarthria, tongue protrusion, finger taps, pronate-supinate hands, luria, rigidity, bradykinesia, gait, tandem walking, and retropulsion pull test.

UHDRS-Chorea

In the UHDRS, maximal chorea is scored from 0 (absent) to 4 (marked/prolonged) on each of the following items: face, mouth, trunk, right upper extremity, left upper extremity, right lower extremity, and left lower extremity. Maximal chorea is the sum of all scores.

UHDRS-Dystonia

In the UHDRS, maximal dystonia is scored from 0 (absent) to 4 (marked/prolonged) on each of the following items: trunk, right upper extremity, left upper extremity, right lower extremity, and left lower extremity. Maximal dystonia is the sum of all scores.

TMS Proportion of Responders

The percentage of responders, defined as patients with UHDRS-TMS change from baseline ≤0 at Week 26.

Other Motor Assessments

Quantitative Motor Assessments

Q-Motor assessments are described in Example 1.

Digitomotography (Speeded Index Finger Tapping)

The Digitomotography (Speeded Index Finger Tapping) assessment is described in Example 1.

Dysdiadochomotography (Pronation/Supination Hand Tapping)

The Digitomotography (Pronation/Supination Hand Tapping) assessment is described in Example 1.

Manumotography and Choreomotography (Grip Force and Chorea Analysis)

This task is described in Example 1.

Pedomotography (Speeded Foot Tapping)

This assessment is described in Example 1.

Timed Up and Go Test

The TUG is described in Example 1.

Cognitive Assessment Battery

The following sections describe the tests that are part of the CAB.

Symbol Digit Modalities Test

The SDMT is a paper-and-pencil test of psychomotor speed and working memory. Participants view a 'key' at the top of the page containing symbols paired with numbers. The remainder of the page displays rows of symbols, and the participant has 90 seconds to write the corresponding number that matches each symbol.

Emotion Recognition

Emotion recognition of facial expressions of emotions is examined using computerized presentations of photographs depicting 6 basic emotions or a neutral expression. Participants are asked to indicate the emotion expressed in each photograph by selecting from the words fear, disgust, happy, sad, surprise, angry, and neutral (10 stimuli per emotion).

Trail Making Tests A and B

In the Trail Making Test, part A, is described in Example 1. Trail A is used only as part of the training.

Hopkins Verbal Learning Test, Revised

The HVLT-R offers a brief assessment of verbal learning and memory (recognition and recall). It is easy to administer and score and is well tolerated even by significantly impaired individuals. Its use has been validated with brain-disordered populations (eg, Alzheimer's disease, HD, amnestic disorders) as a measure of verbal learning and memory. Each form consists of a list of 12 nouns (targets) with 4 words drawn from each of 3 semantic categories. The semantic categories differ across the 6 forms, but the forms are very similar in their psychometric properties. Raw scores are derived for Total Recall, Delayed Recall, Retention (% retained), and a Recognition Discrimination Index. The HVLT-R has high test-retest reliability, and its construct, concurrent, and discriminant validity have been well established.

Paced Tapping Test

Psychomotor function is assessed in a Paced Tapping test. Participants tap on left and right mouse buttons, alternating between thumbs, at 3.0 Hz. They first listen to a tone presented at the desired tapping rate, and then begin tapping to the tone. After 11 taps with the tone, the repetition of the tone is discontinued, and participants attempt to continue tapping at the same rate until the end of the trial (31 taps later).

One Touch Stockings of Cambridge (OTS)

OTS is a spatial planning task which gives a measure of frontal lobe function. OTS is a variant of the Stockings of Cambridge task, and places greater demands on working memory as the participant has to visualize the solution. As with Stockings of Cambridge, the participant is shown 2 displays containing 3 colored balls. The displays are presented in such a way that they can easily be perceived as stacks of colored balls held in stockings or socks suspended from a beam. This arrangement makes the 3 dimensional concepts involved apparent to the participant, and fits with the verbal instructions.

There is a row of numbered boxes along the bottom of the screen. The test administrator first demonstrates to the participant how to use the balls in the lower display to copy the pattern in the upper display, and completes 1 demonstration problem, where the solution requires 1 move. The participant must then complete 3 further problems, 1 each of 2 moves, 3 moves, and 4 moves. Next, the participant is shown further problems, and must work out in their head how many moves the solutions to these problems require, then touch the appropriate box at the bottom of the screen to indicate their response.

Problem Behaviors Assessment-Short Form

Visual attention and task switching are assessed using the Trail Making test, which consists of 25 circles on a standard sheet of paper. For Trails A, participants are required to connect, as quickly as possible, circles containing numbers in ascending numerical order. For Trails B, participants are to connect, as quickly as possible, circles containing numbers and letters, alternating between numbers and letters in ascending order (eg, 1, A, 2, B, 3, C, etc.). Trail A is used only as part of the training.

Assessment of Safety

In this Example (Example 2), safety is assessed by qualified study staff by evaluating the following: reported AEs, clinical laboratory test results, vital signs measurements, ECG findings, physical and neurological examination findings (including body weight), and concomitant medication usage.

During the study, an independent Safety Committee reviews accumulating safety data on 2 occasions:

The first review occurs 6 weeks after 10 patients from each treatment arm (i.e., a total of 50 patients) have been enrolled. The second review occurs 6 weeks after approximately 20 patients from each treatment arm (i.e., a total of 100 patients) have been enrolled.

The Safety Committee is composed of independent physicians with expertise in the relevant therapeutic field (i.e., at least a cardiologist and a neurologist) and other relevant experts, such as a statistician and a PK expert. They have the right to recommend discontinuation of 1 or more treatment arm(s) for safety reasons.

Adverse Events and Withdrawal Due to an Adverse Event

See adverse event section and Withdrawal Due to an Adverse Event Section in Example 1.

Clinical Laboratory Tests

All clinical laboratory tests are conducted as described in the Clinical Laboratory Tests section in Example 1, with the Exception of the timeline below.

Clinical laboratory tests (serum chemistry including electrolytes, hematology and urinalysis) are performed at screening (Visit 0), baseline (Visit 1), Day 14 (Visit 2; electrolytes only), Day 28 (Visit 3), Day 42 (Visit 4), Day 56 (Visit 5), Day 84 (Visit 6), Day 112 (Visit 7), Day 140 (Visit 8), Day 182 (Visit 9) or Early Termination, and at the follow-up visit.

Pregnancy Tests

Human chorionic gonadotropin (HCG) serum test is performed for all women of childbearing age at screening. (Visit 0). HCG urine tests is performed for all women of childbearing age at Day 28 (Visit 3), Day 56 (Visit 5), Day 84 (Visit 6), Day 112 (Visit 7), Day 140 (Visit 8), Day 182 (Visit 9) or Early Termination, at the follow-up visit, and if clinically indicated at any other time. An indeterminate reading for the serum pregnancy test should be checked twice and the patient referred to a gynecologist if required. Any patient who becomes pregnant during the study is withdrawn.

Vital Signs

Vital signs are measured at screening (Visit 0), baseline (Visit 1), Day 14 (Visit 2), Day 28 (Visit 3), Day 42 (Visit 4), Day 56 (Visit 5), Day 84 (Visit 6), Day 112 (Visit 7), Day 140 (Visit 8), Day 182 (Visit 9) or Early Termination, and at the follow-up visit. Vital signs include the following: pulse, blood pressure, body temperature and the procedures described in Example 1 are followed.

Electrocardiography

A single resting 12-lead ECG is conducted after at least 5 minutes of supine rest at screening (Visit 0). If there is evidence of a prolonged QTcF interval at screening (defined as a QTcF interval of >450 msec) then the ECG is repeated twice, and the mean of the 3 screening measurements is used to determine whether or not the patient is suitable for inclusion in the study.

At the Baseline visit, the predose QTcF is determined by the average of 3 ECGs (within 10 to 20 minutes of one another), each in triplicate (in total 9 recordings). A postdose ECG is performed in triplicate 1 to 2 hours after first dosing. ECGs is performed in triplicate prior to dosing on site and 1 to 2 hours after dosing on site at Day 14 (Visit 2), Day 28 (Visit 3), Day 42 (Visit 4), Day 84 (Visit 6), Day 112 (Visit 7), Day 140 (Visit 8). On Day 182 (Visit 9) or Early Termination, a triplicate ECG is performed before the morning dose. At the discretion of the investigator, 12-lead ECG measurements is also performed on Day 56 (Visit 5) where there are clinical circumstances that justify an additional ECG, eg, patients with a previous episode of hypokalemia without QT prolongation.

ECG is also performed in triplicate at the follow-up visit only for patients with a previously observed cardiac concern and/or QTc change from baseline.

The patient is in a supine position and resting for at least 5 minutes prior to each ECG measurement. Where applicable, ECG measurements are taken prior to vital sign measurements and blood being drawn for clinical laboratory or PK evaluations.

A qualified physician at the central ECG vendor is responsible for interpreting the ECG. However, every ECG should be reviewed immediately at site in order to detect any QTcF prolongation of potential clinical concern and allow dosing. Evaluation of the screening ECG(s) for inclusion in the study can be performed locally, i.e., the interpretation from the central ECG vendor is not required for inclusion. Any ECG finding that is judged by the investigator or the physician from the central ECG vendor as a clinically significant change (worsening) compared with a baseline value is considered an AE, recorded on the source documentation and transcribed onto the CRF, and monitored.

Physical and Neurological Examinations

Physical and neurological examinations, including weight are performed at screening (Visit 0), baseline (Visit 1), Day 14 (Visit 2), Day 28 (Visit 3), Day 42 (Visit 4), Day 56 (Visit 5), Day 84 (Visit 6), Day 112 (Visit 7), Day 140 (Visit 8), Day 182 (Visit 9) or Early Termination, and at the follow-up visit. Any physical or neurological examination finding that is judged by the investigator as a clinically significant change (worsening) compared with a baseline value is considered an AE, recorded on the CRF, and monitored.

Height is measured at the screening visit only.

Other Safety Measures and Variables

Concomitant therapy or medication usage is monitored throughout the study.

Columbia Suicide Severity Rating Scale (C-SSRS)

The C-SSRS is used to rate the patient's degree of suicidal ideation on a scale ranging from "no suicidal ideation" to "active suicidal ideation with specific plan and intent" (Posner 2011). The C-SSRS is completed at screening (Visit 0), baseline (Visit 1), Day 28 (Visit 3), Day 42 (Visit 4), Day 56 (Visit 5), Day 84 (Visit 6), Day 112 (Visit 7), Day 140 (Visit 8), and Day 182 (Visit 9) or Early Termination. Patients with active suicidal ideation, as measured by a score of 4 or 5 on the C-SSRS at the screening visit, are not eligible for the study.

Assessment of Pharmacokinetics and Pharmacogenomics

Pharmacokinetic Variables are described in Example 1.

Blood Sampling and Handling

Blood samples (4 mL each) are collected for the determination of plasma concentrations via venipuncture or indwelling catheter in the morning before study drug administration at the following visits:

Titration Period

Day 0 (baseline)-prior and 1 to 2 hours post first dose

Day 14-1 to 2 hours post afternoon dose

Full Treatment Dose Period
  Day 28-pre afternoon dose and 1 to 2 hours post afternoon dose
  Day 42-pre afternoon dose and 1 to 2 hours post afternoon dose
  Day 84-1 to 2 hours post afternoon dose
  Day 112-pre afternoon dose and 1 to 2 hours post afternoon dose
  Day 140-1 to 2 hours post afternoon dose
  Day 182-prior to morning dose
  Follow-up visit
  A total of 13 samples are drawn from each patient for PK analysis.
  In case of an SAE, an additional PK sample is collected at the closest time possible to the SAE.
  The date and time of each PK sample and the dates and times of the last drug administration prior to any collected PK sample are recorded on the source documentation and transcribed onto the CRF. Only major deviations (>5%) from the scheduled blood sampling time points are commented on the respective page of the CRF.
  When ECG evaluation is scheduled at the same time as blood collection, ECG is performed before blood collection.
  Samples are collected in potassium ethylene diamine tetra acetate-containing tubes. Immediately following collection, samples are cooled and centrifuged within 45 minutes at approximately 4° C. at 1500×g for 15 minutes. The plasma is then be transferred into 2 polypropylene tubes (first aliquot [Set A] and back-up [Set B]) and stored below −20° C. until bioanalysis.

Analysis of Samples
  Samples are analyzed as described in Example 1.

Pharmacogenomic Variables
  A blood sample (10 mL) are collected in 2 dipotassium ethylenediaminetetraacetic acid (K2EDTA) plastic tubes at the screening visit for genetic analyses. Analyses include CAG repeats, CYP2D6 status, and genetic long QT syndrome (assessed only in patients experiencing QT prolongation following study drug administration leading to study discontinuation), or any other genetic analyses related to pridopidine response or HD. The analyses of CAG repeats from the screening sample are not be used to assess eligibility for the study: that is assessed using historical data.
  Pharmacogenetic samples are sent to the laboratory within 72 hours from collection in ambient. If DNA extraction is not performed at the laboratory within 24 hours, the samples are stored at −70° C. until DNA extraction is performed. After DNA extraction, the samples are stored either at −20° C. or −70° C.

Efficacy Analysis Summary
Primary Efficacy Variable
  The primary efficacy variable for this study is the change from baseline in the UHDRS-TMS at Week 26.

Secondary Efficacy Variable
  The secondary efficacy analysis variable for this study is the change from baseline in the PPT at Week 26.

Other Efficacy Variables
Global Functional Scales:
  CIBIC-Plus global score at Week 26 as compared to baseline (rated by an independent investigator)
  Change from baseline in the PDS score at Week 26
  Change from baseline in UHDRS-FA at Week 26
  CGI-C at Week 26 as compared to baseline (rated by the study investigator and the patient)
  Change from baseline in UHDRS-TFC at Week 26
  Change from baseline in UHDRS-IS at Week 26

Global/Functional Scales:
  Change from baseline in HD-QoL at Week 26
  Change from baseline in MSWS-12 at Week 26
TMS Subscores:
  Change from baseline in hand movement score at Week 26
  Change from baseline in Gait and balance score at Week 26
  Change from baseline in UHDRS-mMS at Week 26
  Change from baseline in UHDRS-Chorea at Week 26
  Change from baseline in UHDRS-Dystonia at Week 26
  Responders, defined as patients with UHDRS-TMS change from baseline ≤0 at Week 26
Other Motor Assessments:
  Change from baseline in Q-Motor measurements at Week 26
  Change from baseline in the TUG test at Week 26
Cognitive/Psychiatric Assessments:
  Change from baseline in CAB brief at Week 26
  Change from baseline in PBA-s at Week 26

Primary Efficacy Analysis
  The pridopidine dose group of 45 mg bid comparison to placebo is a bridging comparison to the legacy pridopidine studies (ACR16C008 [MermaiHD] and ACR16C009 [HART]), where the pridopidine dose of 45 mg bid was the maximal dose.
  In addition, any treatment group that is discontinued due to safety issues is not formally tested for efficacy and hence not controlled for type I error.
  The change from baseline in UHDRS-TMS is analyzed using a Repeated Measures model (SAS® MIXED procedure with REPEATED sub-command). The model includes the following fixed effects: categorical week in study by treatment interaction, center, neuroleptic use or no use, and baseline UHDRS-TMS score. The unstructured covariance matrix for repeated observations within patients is used. In case that the model does not converge, the Maximum-Likelihood (ML) estimation method is used instead of the default Restricted ML (REML). If the model still does not converge then a simpler covariance structures with less parameters is used, according to the following order: Heterogeneous Autoregressive(1) [ARH(1)], Heterogeneous Compound Symmetry (CSH), Autoregressive(1) [AR (1)], and Compound Symmetry (CS). The estimated means at the Week 26 visit of the change from baseline in UHDRS-TMS is compared between the active treatment arms (the arms from: 67.5, 90, or 112.5 mg bid that are not discontinued due to safety issues) and the placebo arm.

Sensitivity Analysis
  A sensitivity analysis to evaluate if the observed effect in UHDRS-TMS is driven by the Chorea UHDRS-TMS sub-score, the Dystonia UHDRS-TMS sub-score, or the Involuntary Movements (Chorea+Dystonia) UHDRS-TMS sub-score is performed according to the following:
  Three variables are calculated:
    The change from baseline to Week 26 in the sum of the UHDRS-TMS items except the Chorea items
    The change from baseline to Week 26 in the sum of the UHDRS-TMS items except the Dystonia items
    The change from baseline to Week 26 in the sum of the UHDRS-TMS items except the Chorea and Dystonia items
  These variables are analyzed in the same way as the primary efficacy endpoint except that the variable evaluation at baseline are included in the model instead of baseline UHDRS-TMS.

Secondary Efficacy Variable Analyses

Any statistically significant dose that is observed in the primary analysis continues to be tested for the secondary endpoint at an alpha level of 5%.

The change from baseline in PPT is analyzed using a Repeated Measures model (SAS® MIXED procedure with REPEATED sub-command). The model includes the following fixed effects: categorical week in study by treatment interaction, center, neuroleptic use or no use, and baseline PPT score. The unstructured covariance matrix for repeated observations within patients is used. In case that the model does not converge, the ML estimation method is used instead of the default REML. If the model still does not converge then a simpler covariance structures with less parameters is used, according to the following order: ARH(1), CSH, AR (1), and CS. The estimated means at the Week 26 visit of the change from baseline in PPT is compared between the active treatment arms and the placebo arm Other Efficacy Variables Analyses The odds of responders are compared between the active groups and the placebo group using logistic regression analysis (SAS® LOGISTIC procedure) stratified by country using the STRATA sub-command with the following effects: treatment group, neuroleptic use or no use and baseline UHDRS-TMS score.

The other efficacy endpoints are analyzed in the same way as the primary efficacy endpoint except that the efficacy endpoint evaluation at baseline are included in the model instead of baseline UHDRS-TMS.

For CIBIC-Plus, the CIBIS score at baseline is included in the model instead of baseline UHDRS-TMS.

For CGI-C, the CGI-S score at baseline is included in the model instead of baseline UHDRS-TMS Exposure Response Analyses A correlation between $C_{max}$/AUC and efficacy and safety measures is done.

Pooling of Small Centers

Centers with low number of patients are pooled The pooled center variable is used in all statistical models that include center as covariate.

Multiple Comparisons and Multiplicity

The Hochberg's Step-Up method for multiple comparisons between treatment arms in combination with the hierarchical method between the primary efficacy endpoint and the secondary efficacy endpoint, is used to maintain the experiment-wise type I error of 5% level.

The pridopidine dose group of 45 mg bid comparison to placebo is a bridging comparison to the legacy pridopidine studies (ACR16C008 [MermaiHD] and ACR16C009 [HART]), where the pridopidine dose of 45 mg bid was the maximal dose. Hence, only a maximum of 3 multiple dose comparisons to placebo are performed and controlled for type I error in this study: 67.5, 90, and 112.5 mg bid. First, the Hochberg method is be applied for the comparisons of the 3 (or less) active doses (67.5, 90, and 112.5 mg bid) to placebo. Then, using the hierarchical method, any statistically significant dose continues to be tested for the secondary endpoint at an alpha level of 5%.

In addition, any treatment group that is discontinued due to safety issues is not be formally tested for efficacy and hence not controlled for type I error.

Safety Variables and Analysis

Safety Variables

The overall safety and tolerability of pridopidine treatment is assessed throughout the study by evaluating AEs and the following additional safety variables:

clinical laboratory tests
vital signs
12-lead ECG
C-SSRS

Safety Analysis

All AEs are coded using the Medical Dictionary for Regulatory Activities (MedDRA). Each patient is counted only once in each preferred term or SOC category for the analyses of safety. Summaries are presented for all AEs (overall and by severity), AEs determined by the investigator to be related to study treatment (defined as related or with missing relationship) (overall and by severity), serious AEs, and AEs causing withdrawal from the study. Summaries are presented by treatment group and for all patients. Patient listings of SAEs and AEs leading to withdrawal are presented.

Changes in laboratory and vital signs measurement data are summarized descriptively. All values are compared with prespecified boundaries to identify potentially clinically significant changes or values, and such values are listed.

The use of concomitant medications are summarized by therapeutic class using descriptive statistics. Concomitant medications include all medications taken while the patient is treated with study drug.

For continuous variables, descriptive statistics (n, mean, SD, standard error, median, minimum, and maximum) are provided for actual values and changes from baseline to each time point. For categorical variables, patient counts and percentages are provided. Descriptive summaries of SAEs, patient withdrawals due to AEs, and potentially clinically significant abnormal values (clinical laboratory or vital signs) based on predefined criteria are also provided.

If any patient dies during the study, a listing of deaths are provided and all relevant information are discussed in the patient narrative included in the clinical study report.

Pharmacokinetic Analysis

Plasma concentration data on pridopidine and the main metabolite TV-45065 are presented by descriptive statistics by dose of pridopidine and also by CYP2D6 metabolizer status. Concentrations are also incorporated into a pridopidine's population PK model and individual exposure for the study patients (Cmax and AUC) are calculated.

Results

Statistically significant changes from baseline in UHDRS-TMS after 26 weeks of pridopidine administration at 67.5 mg, 90 mg, and 112.5 mg bid are observed. Alternatively, statistically significant changes are observed in the protocol pre-specified motor domain sub scores hereof. These changes indicate that administration of pridopidine at the specified dosages allows for the successful treatment of motor impairment in patients afflicted with HD. Change from baseline is also observed for secondary efficacy variables and endpoints and other functional variables and endpoints described herein, indicating that pridopidine administered at the specified dosages allows for the treatment of motor, mental, functional or cognitive impairment in patients afflicted with HD.

Example 3

A Phase II, Dose-finding, Randomized, Parallel-Group, Double-Blind, Placebo-Controlled Study, Evaluating the Safety and Efficacy of Pridopidine 45 mg, 67.5 mg, 90 mg, and 112.5 mg Twice-Daily versus Placebo for Symptomatic Treatment in Patients with Huntington's Disease Example 3 is identical to Example 2, except as follows. If there is any descrepenacy between the procedures in Example 2 and the procedures listed below, the procedures below are followed for Example 3.

The Modified Physical Performance Test (mPPT) is used instead of the Physical Performance Test (PPT). The Walk-12 scale in used instead of the Multiple Sclerosis Walking Scale (MSWS).

The EQ5D or EQSD-5L assessment is performed (at least): at the baseline visit and Visit 9 (Day 182).

At days 28, 56, 84, 112, 140, and 182, the UHDRS-TMS and the mPPT is assessed.

At Days 28, 84, and 182, in addition to safety assessments and the UHDRS-TMS and mPPT, the CIBIC-Plus are rated and the PDS, the CGI-C, the TUG Test, the UHDRS-FA, the UHDRS-TFC, the UHDRS-IS, and the PBA-s. UHDRS-TMS and mPPT are preferrably evaluated prior to the other scales. The patient completes the Walk-12 and Q-Motor assessments are performed. The UHDRS-FA, the UHDRS-TFC and the UHDRS-IS are also performed on Day 140. The CAB is performed on days 84 and 182 only. The HD-QoL and EQ5D scales are completed on Day 182 only.

Differences in the procedures listed in Table 5 and relevant parts of Example 2 from Example 3 are as follows: The PBA-s, CIBIC-Plus, PDS, CGI-C, MSWSWalk-12 and TUG test are performed on the following visits: baseline (V1); week 4 (V3), week 12 (V6) and week 26/early termination (V9). HD-QOL scale performed at baseline (V1) and week 26/early termination (V9). EQ5D-5L scale is performed at baseline (v1) and week 26/early termination (V9). Q-motor assessments are performed at screening (V0), baseline (V1); week 4 (V3), week 12 (V6) and week 26/early termination (V9) and follow up. Cognitive assessment battery is performed on the following visits: screening (V0); baseline (V1); week 12 (V6), and week 26/early termination (V9).

On Days 28, 56, 84, 112, and 140, the following efficacy procedures/assessments are performed, in priority, either before or after the afternoon dose (with the time of the evaluation recorded): UHDRS-TMS and mPPT. In addition to the UHDRS-TMS and mPPT, the following efficacy procedures/assessments are performed on Days 28 and 84 only, either before or after the afternoon dose (with the time of the evaluation recorded), with UHDRS-TMS and mPPT evaluated in priority: CIBIC-Plus, PDS, UHDRS-FA, UHDRS-TFC, UHDRS-IS (UHDRS-FA, UHDRS-TFC, UHDRS-IS are also performed on Day 140), CGI-C, TUG Test, Walk-12, Q-Motor assessments, and PBA-s. In addition, CAB tests (SDMT, Emotion Recognition, Trail Making, Test, HVLT-R, Paced Tapping at 3 Hz, OTS)—are performed on day 84 only.

Abstinence is an acceptable method of contraception only when this is the preferred and usual lifestyle of the subject. Periodic abstinence (calendar, symptothermal. post-ovulation methods), withdrawal (coitus interruptus), and lactational amenorrhoea method (LAM) are not acceptable methods of contraception.

Primary and secondary efficacy assessments (UHDRS-TMS and mPPT) are performed on Day 0 (Visit 0, baseline), Day 28 (Visit 3), Day 56 (Visit 5), Day 84 (Visit 6), Day 112 (Visit 7), Day 140 (Visit 8), and Day 182 (Visit 9). Exploratory efficacy assessments are performed only at Day 0 (Visit 0, baseline), Day 28 (Visit 3), Day 84 (Visit 6), and Day 182 (Visit 9); apart from the CAB, which are performed only at Day 0 (Visit 0, baseline), Day 84 (Visit 6), and Day 182 (Visit 9); and UHDRS FA, UHDRS TFC, and UHDRS IS which are also performed on Day 140. Except for Day 0, efficacy assessments take place before or after the afternoon dose, with the time of the evaluation recorded. UHDRS-TMS and mPPT are assessed in priority over other exploratory efficacy endpoints. UHDRS-TMS and Q-Motor assessments are also performed at the follow-up visit.

The secondary efficacy analysis variable for this study is the change from baseline in the mPPT at Week 26. (Brown 2000)

The mPPT quantifies the patient's performance in physical tasks (Brown 2000). It is a standardized 9-item test that measures the patient's performance on functional tasks. Assistive devices are permitted for the tasks that require a standing position (items 6 to 9). Both the speed and accuracy at which the patients complete the items are taken into account during scoring. The maximum score of the test is 36, with higher scores indicating better performance.

The Multiple Sclerosis Walking Scale (MSWS-12) was adapted to become a generic measure of walking and mobility and renamed the Walk-12.

The EQ-5D 3 level version (EQ-5D-3L) was introduced in 1990 (EuroQoL Group 1990). It essentially consists of the EQ-5D descriptive system and the EQ visual analogue scale (EQ VAS). The EQ-5D-3L descriptive system comprises the following 5 dimensions: mobility, self-care, usual activities, pain/discomfort and anxiety/depression. In developing the 5L, the 5-dimensional structure of the original EQ-SD-3L was retained but the levels on each dimension were expanded to 5-levels based on qualitative and quantitative studies conducted by the EuroQoL Group. The labels for each of the dimensions are: no problems, slight problems, moderate problems, severe problems, and unable to/extreme problems. The EQ-VAS is still an integral part of the EQ-SD-5L but has been adapted to make it more user-friendly. The respondent is asked to indicate his/her health state by ticking (or placing a cross) in the box against the most appropriate statement in each of the 5 dimensions. The EQ VAS records the respondent's self-rated health on a vertical, visual analogue scale where the endpoints are labeled 'Best imaginable health state' and 'Worst imaginable health state'. This information can be used as a quantitative measure of health outcome as judged by the individual respondents. It should be noted that the numerals 1-3 have no arithmetic properties and should not be used as a cardinal score. The EQSD can be completed by the patients with caregiver/informant assistance if needed.

The CAB assessments may or many not be performed.

Regarding HVLT-R, Raw scores are derived for Learning Trials 1-3 (i.e., Total Recall) and Trial 4 (e.g., Delayed Recall Trial).

New symptoms of HD or deterioration of previously existing symptoms should be recorded as an AE only if the presentation and/or outcome is more severe than would normally be expected from the normal course of the disease in a particular patient.

Additional sensitivity analysis is performed for change from baseline in UHDRS-TMS on the FUAS population, including efficacy observations measured after study drug discontinuation.

The change from baseline in HD-QoL and in EQ5D-SL at week 26/Early Termination is analyzed using an Analysis of Covariance (ANCOVA) Model. The model includes the following fixed effects: treatment, center, neuroleptic use or no use, and baseline HD-QOL or EQ5D-5L score. The last observation carried forward (LOCF) is applied for these endpoints for early terminated subjects.

Results

Statistically significant changes from baseline in UHDRS-TMS after 26 weeks of pridopidine administration at 67.5 mg, 90 mg, and 112.5 mg bid are observed. Alternatively, statistically significant changes are observed in the protocol pre-specified motor domain sub scores hereof. These changes indicate that administration of pridopidine at the specified dosages allows for the successful treatment of motor impairment in patients afflicted with HD. Change from baseline is also observed for secondary efficacy variables and endpoints and other functional variables and endpoints described herein, indicating that pridopidine administered at the specified dosages allows for the treatment of motor, mental, functional or cognitive impairment in patients afflicted with HD.

REFERENCES CITED

Mahant N, McCusker E A, Byth K, Graham S; Huntington Study Group. Huntington's disease: clinical correlates of disability and progression. Neurology. 2003 Oct. 28; 61 (8): 1085-92.

Nieoullon A, Coquerel A. Dopamine: a key regulator to adapt action, emotion, motivation and cognition. Curr Opin Neurol 2003 December; 16 Suppl 2: S3-9.

Zhan L, Kerr J R, Lafuente M J, Maclean A, Chibalina M V, Liu B, Burke B, Bevan S, Nasir J. Altered expression and coregulation of dopamine signalling genes in schizophrenia and bipolar disorder. Neuropathol Appl Neurobiol. 2011 February; 37 (2): 206-19.

Dunlop B W, Nemeroff C B. The role of dopamine in the pathophysiology of depression. Arch Gen Psychiatry. 2007 March; 64 (3): 327-37.

Kung V W, Hassam R, Morton A J, Jones S. Dopamine-dependent long term potentiation in the dorsal striatum is reduced in the R6/2 mouse model of Huntington's disease. Neuroscience. 2007 Jun. 8; 146 (4): 1571-80.

Huot P, Lévesque M, Parent A. The fate of striatal dopaminergic neurons in Parkinson's disease and Huntington's chorea. Brain. 2007 January; 130 (Pt 1): 222-32.

Mestre T, Ferreira J, Coelho M M, Rosa M, Sampaio C. Therapeutic interventions for disease progression in Huntington's disease. Cochrane Database Syst Rev. 2009 Jul. 8; (3): CD006455.

Mestre T, Ferreira J, Coelho M M, Rosa M, Sampaio C. Therapeutic interventions for symptomatic treatment in Huntington's disease. Cochrane Database Syst Rev. 2009 Jul. 8; (3): CD006456.

Ponten H, Kullingsjö J, Lagerkvist S, Martin P, Pettersson F, Sonesson C, Waters S, Waters N. In vivo pharmacology of the dopaminergic stabilizer pridopidine. Eur J Pharmacol. 2010 Oct. 10; 644 (1-3): 88-95

Dyhring T, Nielsen EØ, Sonesson C, Pettersson F, Karlsson J, Svensson P, Christophersen P, Waters N. The dopaminergic stabilizers pridopidine (ACR16) and (−)-OSU6162 display dopamine D(2) receptor antagonism and fast receptor dissociation properties. Eur J Pharmacol. 2010 Feb. 25; 628 (1-3): 19-26.

Natesan S, Svensson K A, Reckless G E, Nobrega J N, Barlow K B, Johansson A M, Kapur S. The dopamine stabilizers (S)-(−)-(3-methanesulfonyl-phenyl)-1-propyl-piperidine [(−)-OSU6162] and 4-(3-methanesulfonylphenyl)-1-propyl-piperidine (ACR16) show high in vivo D2 receptor occupancy, antipsychotic-like efficacy, and low potential for motor side effects in the rat. J Pharmacol Exp Ther. 2006 August; 318 (2): 810-8.

Carlsson A, Lindqvist M. Effect of chlorpromazine or haloperidol on formation of 3-methoxytyramine and normetanephrine in mouse brain. Acta Pharmacol Toxicol (Copenh). 1963; 20:140-4.

Waters S. Pettersson F, Dyhring T, Sonesson C, Tedroff J, Waters N et al. Pharmacology of the dopaminergic stabilizer pridopidine (ACR16). Clin Genet 2009; 76 (S1): 74 (Abstract D10).

Cepeda C, Cummings D M, Andre V M, Holley S M, Levine M S. Genetic mouse models of Huntington's disease: focus on electrophysiological mechanisms. ASN Neuro. 2010 Apr. 7; 2 (2): e00033.

Alexander G E, DeLong M R, Strick P L. Parallel organization of functionally segregated circuits linking basal ganglia and cortex. Annu Rev Neurosci. 1986; 9:357-81.

Huntington Study Group. Tetrabenazine as antichorea therapy in Huntington disease: a randomized controlled trial. Neurology. 2006 Feb. 14; 66 (3): 366-72.

Huntington Study Group. Dosage effects of riluzole in Huntington's disease: a multicenter placebo-controlled study. Neurology. 2003 Dec. 9; 61 (11): 1551-6.

Huntington Study Group TREND-HD Investigators. Randomized controlled trial of ethyleicosapentaenoic acid in Huntington disease: the TREND-HD study. Arch Neurol. 2008 December; 65 (12): 1582-9.

Exploratory Population Pharmacokinetic Modeling and Simulations With Pridopidine (Report Number: CP-13-013). Pharsight Consulting Services, 10 Jul. 2013. Wellbutrin label Huntington Study Group. Unified Huntington's Disease Rating Scale: reliability and consistency. Huntington Study Group. Mov Disord. 1996 March; 11 (2): 136-42.

Reuben D B, Siu A L. An objective measure of physical function of elderly outpatients. The Physical Performance Test. J Am Geriatr Soc. 1990 October; 38 (10): 1105-12.

Joffres C, Graham J, Rockwood K. Qualitative analysis of the clinician interview-based impression of change (Plus): methodological issues and implications for clinical research. Int Psychogeriatr. 2000 September: 12 (3): 403-13.

Myers R H, Sax D S, Koroshetz W J, Mastromauro C, Cupples L A, Kiely D K, Pettengill F K, Bird E D. Factors associated with slow progression in Huntington's disease. Arch Neurol. 1991 Aug48 (8): 800-4.

Guy W. Clinical Global Impression: ECDEU assessment manual for psychopharmacology. Publication ADM-76-338, US Department of Health, Education, and Welfare Washington DC: US Government Printing Office. 1976: 217-22.

Hocaoglu M B, Gaffan E A, Ho A K. The Huntington's Disease health-related Quality of Life questionnaire (HDQOL): a disease-specific measure of health-related quality of life. Clin Genet. 2012 February; 81 (2): 117-22.

Hobart J C, Riazi A, Lamping D L, Fitzpatrick R, Thompson A J. Measuring the impact of MS on walking ability: the 12-Item MS Walking Scale (MSWS-12). Neurology. 2003 Jan. 14; 60 (1): 31-6.

Podsiadlo D, Richardson S. The timed "Up & Go": a test of basic functional mobility for frail elderly persons. J Am Geriatr Soc. 1991 February; 39 (2): 142-8.

Rao A K, Muratori L, Louis E D, Moskowitz C B, Marder K S. Clinical measurement of mobility and balance impairments in Huntington's disease: validity and responsiveness. Gait Posture. 2009 April; 29 (3): 433-6.

Stroop J R. Studies of interference in serial verbal reactions. J Exp Psychol 1935; 18:643-62.

Bezdicek O, Majerova V, Novak M, Nikolai T, Ruzicka E, Roth J. Validity of the Montreal Cognitive Assessment in the detection of cognitive dysfunction in Huntington's disease. Appl Neuropsychol Adult. 2013; 20 (1): 33-40.

Bowie C R, Harvey P D. Administration and interpretation of the Trail Making Test. Nat Protoc. 2006; 1 (5): 2277-81.

Craufurd D, Thompson J C, Snowden J S. Behavioral changes in Huntington Disease. Neuropsychiatry Neuropsychol Behav Neurol. 2001 October-December; 14 (4): 219-26.

Kingma E M, van Duijn E, Timman R, van der Mast R C, Roos R A. Behavioural problems in Huntington's disease using the Problem Behaviours Assessment. Gen Hosp Psychiatry. 2008 March-April; 30 (2): 155-6

Posner K, Brown G K, Stanley B, Brent D A, Yershova K V, Oquendo M A, Currier G W, Melvin G A, Greenhill L, Shen S, Mann J J. The Columbia-Suicide Severity Rating Scale: initial validity and internal consistency findings from three multisite studies with adolescents and adults. Am J Psychiatry. 2011 December; 168 (12): 1266-77.

Brown M, Sinacore D R, Binder E F, Kohrt W M. Physical and performance measures for the identification of mild to moderate frailty. J Gerontol A Biol Sci Med Sci. 2000 June; 55A (6): M350-5.

The EuroQoL Group. EuroQoL-a new facility for the measurement of health-related quality of life. Health Policy 1990; 16:199-208.

What is claimed is:

1. A method of reducing impairment of functional capacity of a human patient afflicted with Huntington's disease, consisting essentially of orally administering to the human patient a pharmaceutical composition comprising only pridopidine or a pharmaceutically acceptable salt thereof as the active ingredient, thereby reducing impairment of functional capacity of the human patient.

2. The method of claim 1, wherein the human patient has ≥36 CAG repeats in the Huntingtin gene.

3. The method of claim 1, wherein the pharmaceutical composition is administered twice per day.

4. The method of claim 3, wherein an equal amount of the pharmaceutical composition is administered at each administration.

5. The method of claim 1, wherein the impairment of the human patient's functional capacity is measured by the Unified Huntingtin's Disease Rating Scale (UHDRS) Total Functional Capacity (TFC).

6. The method of claim 1, wherein the pharmaceutical composition comprising pridopidine or a pharmaceutically acceptable salt thereof is administered at a dose of between 90 mg and 225 mg per day.

7. The method of claim 1, wherein the pharmaceutical composition comprising pridopidine or a pharmaceutically acceptable salt thereof is administered at a dose of between 90 mg and 180 mg per day.

8. The method of claim 7, wherein the pharmaceutical composition comprising pridopidine or a pharmaceutically acceptable salt thereof is administered at a dose of 90 mg b.i.d. per day.

9. The method of claim 7, wherein the pharmaceutical composition comprising pridopidine or a pharmaceutically acceptable salt thereof is administered at a dose of 45 mg b.i.d. per day.

* * * * *